US012576025B2

(12) United States Patent
Giehm et al.

(10) Patent No.: US 12,576,025 B2
(45) Date of Patent: *Mar. 17, 2026

(54) PHARMACEUTICAL PARENTERAL COMPOSITION OF DUAL GLP1/2 AGONIST

(71) Applicant: Zealand Pharma A/S, Søborg (DK)

(72) Inventors: Lise Giehm, Søborg (DK); Alistair Vincent Gordon Edwards, Søborg (DK)

(73) Assignee: Zealand Pharma A/S, Søborg (DK)

( * ) Notice: Subject to any disclaimer, the term of this patent is extended or adjusted under 35 U.S.C. 154(b) by 1067 days.

This patent is subject to a terminal disclaimer.

(21) Appl. No.: 17/617,670

(22) PCT Filed: Jun. 12, 2020

(86) PCT No.: PCT/EP2020/066376
§ 371 (c)(1),
(2) Date: Dec. 9, 2021

(87) PCT Pub. No.: WO2020/249778
PCT Pub. Date: Dec. 17, 2020

(65) Prior Publication Data
US 2023/0212227 A1 Jul. 6, 2023

(30) Foreign Application Priority Data

Jun. 14, 2019 (EP) ..................................... 19180233

(51) Int. Cl.
| | |
|---|---|
| A61K 9/00 | (2006.01) |
| A61K 47/02 | (2006.01) |
| A61K 47/26 | (2006.01) |
| A61K 47/54 | (2017.01) |
| C07K 14/00 | (2006.01) |

(52) U.S. Cl.
CPC ............ *A61K 9/0029* (2013.01); *A61K 47/02* (2013.01); *A61K 47/26* (2013.01); *A61K 47/542* (2017.08); *C07K 14/001* (2013.01)

(58) Field of Classification Search
CPC ...... A61K 47/542; A61K 38/00; A61K 38/26; C07K 14/001
See application file for complete search history.

(56) References Cited

U.S. PATENT DOCUMENTS

| | | | |
|---|---|---|---|
| 10,093,713 B2 | 10/2018 | Shelton et al. | |
| 10,905,745 B2 | 2/2021 | Due Larsen et al. | |
| 11,008,375 B2 | 5/2021 | Shelton et al. | |
| 11,395,847 B2 | 7/2022 | Due Larsen et al. | |
| 2007/0010424 A1 | 1/2007 | Pedersen et al. | |
| 2014/0287998 A1 | 9/2014 | Rylander, Jr. et al. | |
| 2015/0190475 A1 | 7/2015 | Bley et al. | |
| 2018/0155406 A1 | 6/2018 | Bossart et al. | |
| 2019/0142904 A1 | 5/2019 | Due Larsen et al. | |
| 2019/0365865 A1 | 12/2019 | Due Larsen et al. | |

| | | | |
|---|---|---|---|
| 2020/0297818 A1 | 9/2020 | Due Larsen et al. | |
| 2022/0202704 A1* | 6/2022 | Giehm ................... A61K 47/26 | |
| 2023/0000951 A1 | 1/2023 | Due Larsen et al. | |
| 2023/0110689 A1 | 4/2023 | Griffin et al. | |
| 2023/0129788 A1 | 4/2023 | Griffin et al. | |
| 2023/0212227 A1 | 7/2023 | Giehm et al. | |
| 2023/0405087 A9 | 12/2023 | Due Larsen et al. | |
| 2023/0405088 A1 | 12/2023 | Villadsen et al. | |
| 2024/0024425 A1 | 1/2024 | Villadsen et al. | |
| 2024/0299552 A1 | 9/2024 | Villadsen et al. | |
| 2024/0316155 A1 | 9/2024 | Griffin et al. | |

FOREIGN PATENT DOCUMENTS

| | | | |
|---|---|---|---|
| CN | 1571676 A | 1/2005 | |
| CN | 103893744 A | 7/2014 | |
| CN | 107750168 A | 3/2018 | |
| EA | 012440 B1 | 10/2009 | |
| EP | 1687019 A2 | 8/2006 | |
| JP | 2003519195 A | 6/2003 | |
| JP | 2012188424 A | 10/2012 | |
| JP | 2013517325 A | 5/2013 | |
| JP | 2019-514949 A | 6/2019 | |
| JP | 2019536796 A | 12/2019 | |
| JP | 2022-535556 A | 8/2022 | |
| KR | 20200080331 A | 7/2020 | |
| RU | 2182015 C2 | 5/2002 | |
| RU | 2560254 C2 | 8/2015 | |
| RU | 2636043 C2 | 11/2017 | |
| WO | WO-9739031 A1 | 10/1997 | |
| WO | WO-97/48414 A1 | 12/1997 | |
| WO | WO-98/11125 A1 | 3/1998 | |
| WO | WO-9808871 A1 | 3/1998 | |
| WO | WO-200055119 A1 | 9/2000 | |
| WO | WO-200055184 A1 | 9/2000 | |

(Continued)

OTHER PUBLICATIONS

Bell, L.N. (1997), Peptide Stability in Solids and Solutions. Biotechnol Progress, 13: 342-346. https://doi.org/10.1021/bp970057y (Year: 1997).*

Gekko K. Mechanism of polyol-induced protein stabilization: solubility of amino acids and diglycine in aqueous polyol solutions. J Biochem. 1981;90(6):1633-41. doi: 10.1093/oxfordjournals. jbchem.a133638. PMID: 7333999. (Year: 1981).*

Marnix A. Hoitink, Jos H. Beijnen, Marcel U. S. Boschma, Auke Bult, Ed Hop, Jack Nijholt, Cees Versluis, Gerard Wiese, and Willy J. M. Underberg Analytical Chemistry 1997 69 (24), 4972-4978 DOI: 10.1021/ac970634x (Year: 1997).*

Singh, S., Singh, J. Effect of polyols on the conformational stability and biological activity of a model protein lysozyme. AAPS PharmSciTech 4, 42 (2003). https://doi.org/10.1208/pt040342 (Year: 2003).*

(Continued)

*Primary Examiner* — Lianko G Garyu
*Assistant Examiner* — David Paul Bowles
(74) *Attorney, Agent, or Firm* — MARSHALL, GERSTEIN & BORUN LLP

(57) ABSTRACT

The present invention relates to pharmaceutical compositions suitable for parenteral administration in human subjects. In particular, the present invention relates to isotonic pharmaceutical compositions for parenteral administration.

25 Claims, No Drawings

Specification includes a Sequence Listing.

(56) References Cited

FOREIGN PATENT DOCUMENTS

| | | |
|---|---|---|
| WO | WO-01/49314 A2 | 7/2001 |
| WO | WO-2003035099 A1 | 5/2003 |
| WO | WO-2005046716 A1 | 5/2005 |
| WO | WO-2006/118805 A2 | 11/2006 |
| WO | WO-2006117565 A2 | 11/2006 |
| WO | WO-2008/070721 A2 | 6/2008 |
| WO | WO-2008134425 A1 | 11/2008 |
| WO | WO-2009/155257 A1 | 12/2009 |
| WO | WO-2011050174 A1 | 4/2011 |
| WO | WO-2011090306 A2 | 7/2011 |
| WO | WO-2013/164484 A1 | 11/2013 |
| WO | WO-2014/071074 A2 | 5/2014 |
| WO | WO-2015/067715 A2 | 5/2015 |
| WO | WO-2015/095406 A1 | 6/2015 |
| WO | WO-2016/066818 A1 | 5/2016 |
| WO | WO-2016193371 A1 | 12/2016 |
| WO | WO-2017/192449 A1 | 11/2017 |
| WO | WO-2018/104558 A1 | 6/2018 |
| WO | WO-2018/104560 A1 | 6/2018 |
| WO | WO-2018/104561 A1 | 6/2018 |
| WO | WO-2018100134 A1 | 6/2018 |
| WO | WO-2018103868 A1 | 6/2018 |
| WO | WO-2019040399 A1 | 2/2019 |
| WO | WO-2019066586 A1 | 4/2019 |
| WO | WO-2019086559 A1 | 5/2019 |
| WO | WO-2019090209 A1 | 5/2019 |
| WO | WO-2020/249782 | 6/2020 |
| WO | WO-2020/249778 A1 | 12/2020 |
| WO | WO-2020/249782 A1 | 12/2020 |

OTHER PUBLICATIONS

Zapadka KL, Becher FJ, Gomes dos Santos AL, Jackson SE. 2017 Factors affecting the physical stability (aggregation) of peptide therapeutics. Interface Focus 7:20170030. http://dx.doi.org/10.1098/rsfs.2017.0030 (Year: 2017).*

Single Point Mutations Induce a Switch in the Molecular Mechanism of the Aggregation of the Alzheimer's Disease Associated Aβ42 Peptide Benedetta Bolognesi et al. ACS Chemical Biology 2014 9 (2), 378-382 DOI: 10.1021/cb400616y (Year: 2013).*

W H Burgess et al. Possible dissociation of the heparin-binding and mitogenic activities of heparin-binding (acidic fibroblast) growth factor-1 . . . J Cell Biol Nov. 1, 1990; 111 (5): 2129-2138. doi: https://doi.org/10.1083/jcb.111.5.2129 (Year: 1990).*

Stoll, Vincent S., and John S. Blanchard. "[4] Buffers: Principles and practice." Methods in enzymology. vol. 182. Academic press, 1990. 24-38. (Year: 1990).*

Hasim et al., Efficacy and safety of isotonic and hypotonic intravenous maintenance fluids in hospitalised children: a systematic review and meta-analysis of randomised controlled trials, Children, 8:785 (2021).

Izutsu, Stabilization of therapeutic proteins by chemical and physical methods, pp. 287-292 IN Smales et al. (eds), Therapeutic Proteins, Humana Press (2005).

The Byju's chemistry webpage, https://byjus.com/chemistry/mannitol/, downloaded Oct. 2024.

U.S. Appl. No. 18/039,857, filed Jun. 1, 2023, Villadsen et al.

U.S. Appl. No. 18/037,795, filed May 19, 2023, Villadsen et al.

U.S. Appl. No. 18/039,992, filed Jun. 2, 2023, Villadsen et al.

U.S. Appl. No. 18/275,195, filed Jul. 31, 2023, Griffin et al.

Handbook of pharmaceutical excipients, 5th ed, edited by Raymond C Rowe, Pharmaceutical Press and American Pharmacists Association, 2006, pp. 449, 693, 696.

Krasnyuk et al., Pharmaceutical Technology: Technology dosage forms, 2nd edition, 2006, pp. 297-299.

Severin, Biochemistry: Textbook, 2nd edition revised, Geotar-Med, 784, pp. 12-13 (2004).

Krasnyuk et al., Pharmaceutical technology:Technology of dosage forms: textbook for students of higher educational institutions, In: Krasnyuk et al., (eds.), Publishing Center "Academy", pp. 6 and 305 (2006).

Dukhanin, Hydrogen index (pH) of the base of a topical medicinal product: selection of the optimal value and the role of the buffer system, Clinical dermatology and venereology, T.15-N2, pp. 47-52 (2016).

Pramanick et al. Excipient Selection In Parenteral Formulation Development, Pharma Times. 45(3):65-77 (2013).

Rowe et al. (eds.), Handbook of Pharmaceutical Excipients. Sixth edition. Pharmaceutical Press and American Pharmacists Association, p. 424 (2009).

Altschul et al. , Local Alignment Statistics, Methods in Enzymology, 1996, vol. 266, pp. 460-480.

Austin et al., Current and potential therapeutic targets of glucagon-like peptide-2, Curr. Opin. Pharmacol., 31:13-18 (Dec. 2016).

Berlin et al., Villus Growth, Increased Intestinal Epithelial Sodium Selectivity, and Hyperaldosteronism Are Mechanisms of Adaptation in a Murine Model of Short Bowel Syndrome. Dig Dis Sci. May 2019;64(5):1158-1170.

Blaufuss et al., Glucagon-like peptides ameliorate total prenteral nutrition associated gut atrophy, 2015, 798.

Cederholm et al., ESPEN guidelines on definitions and terminology of clinical nutrition, Clinical Nutrition 36 (2017) 49-64.

Chueshov et al. Industrial technology medicines: [Textbook. In 2 volumes. vol. 2 / V.I. Chueshov, M.Yu. Chernov, L.M. Khokhlova, etc.]; Edited by Professor V.I. Chueshov.-Kh.: MTK-Book; NFAU Publishing House, 2002.—716 pp.—p. 55, 3.6. Characteristics of solvents.

Clinical pharmacology and pharmacotherapy: textbook.—3rd ed., additional and revised/ edited by V.G. Kukes, A.K. Starodubtseva.—M.: GEOTAR—Media, 2012.—832 pp.: ill.—pp. 384-385.

European Patent Application No. 20214558.7, Extended European Search Report, dated May 19, 2021.

Hovgaard et al. (eds.), Pharmaceutical Formulation Development of Peptides and Proteins, 2nd ed., CRC Press Taylor & Francis Group (2013). [Table of Contents].

Hvistendahl et al., Effect of Liraglutide Treatment on Jejunostomy Output in Patients with Short Bowel Syndrome: An Open-Label Pilot Study, Journal of Parental and Enteral Nutrition, Jan. 2018, vol. 42 No. 1, pp. 112-121.

Hvistendahl et al., Su1982—Glepaglutide, a Glucogon-like peptide-2 analog, ameliorates accelerated gastrointestinal transit time n patients with short bowl syndrome, Gastroenterology, Annual Meeting of the American Society for gastrointestinal-endoscopy, Digestive Disease Week, May 1, 2018, vol. 154, No. 6, pp. S-655.

Jain et al., Validating hyperbilirubinemia and gut mucosal atrophy with a novel ultramobile ambulatory total parenteral nutrition piglet model, Nutrition research, 2015, vol. 35, No. 2, 169-174.

Jeejeebhoy et al., Management of Short Bowel Syndrome: Avoidance of Total Parenteral Nutrition, Gastroenterology, 130(2):S60-S66 (Feb. 2006).

Jeppesen et al., 757 Teduglutide, a Glucagon-like Peptide-2 (GLP-2) Analog, improves fluid balance in short bowel syndrome (SBS) patients depending on parenteral support (PN), Gastroenterology, Apr. 1, 2008, vol. 134, No. 4, p. A-110.

Jeppesen, Teduglutide for the treatment of short bowel syndrome, Drugs for Today, Jan. 1, 2013, vol. 49, No. 10, p. 599-614.

Jeppesen, Teduglutide, a novel glucagon-like peptide 2 analog, in the treatment of patients with short bowel syndrome, Ther. Adv. Gastroenterol., 5(3): 159-171 (2012).

Jeppesen, The Long Road to the Development of Effective Therapies for the Short Gut Syndrome: A Personal Perspective, Digestive Diseases and Sciences, published online Aug. 13, 2019.

Jeppesen, The non-surgical treatment of adult patients with short bowel syndrome, Expert Opinion on Orphan Drugs, 2013, p. 527.

Just, The novel GLP-1/GLP-2 dual agonist ZP-GG-72 increases intestinal growth and improves insulin sensitivity in DIO mice, Diabetes, 163:A1-A102 (Jan. 2014).

Kharitonov, Analytical chemistry (analytics). in 2 books. Book 1. General theoretical foundations. Qualitative analysis. Textbook for universities.—2nd ed., rev.—M.: Higher. school, 2003.—615 p. ill.

Knudsen et al., Potent Derivatives of Glucagon-like Peptide-1 with Pharmacokinetic Properties Suitable for Once Daily Administration, J. Med Chem., 2000, 43:1664-1669.

(56) References Cited

OTHER PUBLICATIONS

Kunkel et al., Efficacy of the glucagon-like peptide-1 agonist exenatide in the treatment of short bowl syndrome, Neurogastroenterology & Motility, Aug. 10, 2011, vol. 23, No. 8, pp. 739-745.

Madsen et al., Acute effects of continuous infusions of glucagon-like peptide (GLP)-1, GLP-2 and the combination (GLP-1+GLP-2) on intestinal absorption in short bowel syndrome (SBS) patients. A placebo-controlled study, Regulatory Peptides. Jun. 10, 2013; vol. 184:pp. 30-39.

Madsen et al., Structure-Activity and Protection Relationship of Long-Acting Glucagon-like Peptide-1 Derivatives: Importance of Fatty Acid Length, Polarity, and Bulkiness, J. Med. Chem. 50:6126-32 (2007).

Massironi et al., Understanding short bowel syndrome; Current status and future perspectives, Digestive and Liver Disease, Dec. 28, 2019, vol. 52, No. 3, pp. 253-261.

NIH US National Library of Medicine, Phase 1 trial, A Single Ascending Dose Trial Assessing Safety, Tolerability, Pharmacokinetics and Pharmacodynamics of ZP7570, first posted Jun. 21, 2019, last update posted Dec. 2, 2020.

Pearson et al., Comparison of DNA Sequences with Protein Sequences, Genomics, vol. 46, pp. 24-36 (1997).

Reiner et al., Teduglutide increases adaptation in a murine short bowel model by improving epithelial tight junction selectivity, Gastroenterology, vol. 156, supplement S-152, published May 2019, AGA Abstracts p. S-152 abstract 696.

Reiner et al., Teduglutide increases adaptation in a murine short bowel model by improving epithelial tight junction selectivity, Teduglutide in SBS mouse model: Poster from University of Rostock, 2019.

Reiner et al., Teduglutide Increases Adaption in a murine short bowel model by improving epithelial tight junction selectivity, Abstract No. P2B20, CIRTA 2019, 16th International Congress of the Intestinal Rehabilitation & Transplant Association, Paris France (Jul. 3-6, 2019).

Reiner et al., Teduglutide Promotes Epithelial Tight Junction Pore Function in Murine Short Bowel Syndrome to Alleviate Intestinal Insufficiency, Dig. Dis. Sci., 65(12):3521-37 (Dec. 2020).

Revestive: Annex I Summary of Product Characteristics, Jan. 1, 2012, downloaded from the Internet at: URL: https://ec.europa.eu/health/documents/community-register/2012/20120830123903/anx_123903_en.pdf.

Russian Patent Application No. 2021139211, Office Action, dated Feb. 1, 2024.

Shestakova, Incretins in the treatment of type 2 diabetes mellitus. Klin. Pharmacol. Ter., 2012, 21 (2), 59-65.—p. 60, Table 1.

Skarbaliene et al., PT01.2: ZP7570: A Novel GLP-1/GLP-2 Dual Acting Peptide with Potential as the Next Generation Therapy for Short Bowel Syndrome, Aug. 14, 2019, 5614(19)32542-7.

Skarbaliene et al., PT01.2: ZP7570: A Novel GLP-1/GLP-2 Dual Acting Peptide with Potential as the Next Generation Therapy for Short Bowel Syndrome, Clinical Nutrition, vol. 38, Sep. 1, 2019, p. S33.

Skarbaliene et al., PT01.2: ZP7570: A Novel GLP-1/GLP-2 Dual Acting Peptide with Potential as the Next Generation Therapy for Short Bowel Syndrome, Poster at 41st European Society for Clinical Nutrition and Metabolism, Jul. 5, 2019.

Skarbaliene et al., PT01.2: ZP7570: A Novel GLP-1/GLP-2 Dual Acting Peptide with Potential as the Next Generation Therapy for Short Bowel Syndrome, Abstracts of the 41st ESPEN Congress, Krakow, Poland, Aug. 31-Sep. 3, 2019.

Skarbaliene et al., PT01.2: ZP7570: A Novel GLP-1/GLP-2 Dual Acting Peptide with Potential as the Next Generation Therapy for Short Bowel Syndrome, Clinical Nutrition, 38(19):S33-S58 (Sep. 2019).

Slim et al., Novel Long-Acting GLP-2 Analogue, FE 203799 (Apraglutide), Enhances Adaptation and Linear Intestinal Growth in a Neonatal Piglet Model of Short Bowel Syndrome with Total Resection of the Ileum, Journal of Parenteral and Enteral Nutrition, 2018.

Villalona et al., No Gut No Gain! Enteral Bile Acid Treatment Preserves Gut Growth but Not Parenteral Nutrition-Associated Liver Injury in a Novel Extensive Short Bowel Animal Model, Journal of parenteral and enteral nutrition, 42(8):1238-1251 (2018).

Wen, Glucagon-Like Peptides Ameliorate Total Prenteral Nutrition Associated Gut Atrophy, Abstract Su1798, American Association for the Study of Liver Diseases (AASLD) Abstracts (2015).

Wismann et al., Novel GLP-1GLP-2 co-agonists display marked effects on gut volume and improves glycemic control in mice, Physiol. Behav., 192:72-81 (Aug. 2018).

Zealand Pharma and Larix A/S, A Phase 2 Trial Testing ZP1848 in Patients with SBS, downloaded from the Internet at: <https://www.clinicaltrials.gov/ct2/show/NCT02690025>, first posted Feb. 24, 2016.

U.S. Appl. No. 17/617,675, Zealand Pharma As.

International Application No. PCT/EP2020/066376, International Search Report and Written Opinion, mailed Sep. 3, 2020.

International Application No. PCT/EP2020/066376, International Preliminary Report on Patentability, dated Dec. 23, 2021.

Berge et al., Pharmaceutical Salts, Journal Pharmaceutical Sciences, 1977, 66(1), pp. 1-19.

Fields et al., 2002, "Principles and practice of solid-phase peptide synthesis". In: Grant G (ed) Synthetic Peptides, 2nd Edition, chapter 3, pp. 93-219.

Groenning et al., Study on the binding of Thioflavin T to beta-sheet-rich and non-beta-sheet cavities, J. Structural Biology, 2007, vol. 158(3), pp. 358-369.

Groenning, Binding mode of Thioflavin T and other molecular probes in the context of amyloid fibrils-current status, J.Chem. Biol., 2010, 3(1), pp. 1-18.

Jones, Analysis of polypeptides and proteins, Advanced Drug Delivery Review, 1993, vol. 10, pp. 29-90.

LeVine, Thioflavine T interaction with synthetic Alzheimer's disease beta-amyloid peptides: detection of amyloid aggregation in solution, Protein Science, 1993, 2(3), pp. 404-410.

Pearlman et al., Analysis of Protein Drugs, In: Lee et al. (eds.), Peptide and Protein Drug Delivery, Marcel Dekker, Inc., New York, N.Y., Pubs. (1991) pp. 247-301.

U.S. Appl. No. 18/275,195, Griffin et al.

Ahern et al., Stability of Protein Pharmaceuticals, Plenum Press, 328 pages (1992).

Stroppel et al., Antimicrobial Preservatives for Protein and Peptide Formulations: An Overview, Pharmaceutics, 15, 563, pp. 1-53 (2023).

* cited by examiner

PHARMACEUTICAL PARENTERAL COMPOSITION OF DUAL GLP1/2 AGONIST

CROSS-REFERENCE TO RELATED APPLICATIONS

This application is a U.S. national phase of International Application No. PCT/EP2020/066376, filed on Jun. 12, 2020, which claims priority to European Patent Application No. 19180233.9, filed on Jun. 14, 2019.

INCORPORATION BY REFERENCE OF MATERIAL SUBMITTED ELECTRONICALLY

The Sequence Listing, which is a part of the present disclosure, is submitted with the specification as a text file that is named "57200_Seqlisting.txt" and was created on Nov. 17, 2021, and is 2,943 bytes in size. The subject matter of the Sequence Listing is incorporated herein in its entirety by reference.

TECHNICAL FIELD

This application concerns pharmaceutical compositions suitable for parenteral administration in human subjects. Thus, this application concerns isotonic pharmaceutical compositions for parenteral administration. The pharmaceutical compositions according to the invention are particularly stable, and have an advantageous shelf-life.

BACKGROUND OF THE INVENTION

Peptides are an important segment of the pharmaceutical industry. Although there have been tremendous advances in production of the active pharmaceutical ingredient (API), production of peptide-based drug products is still a significant challenge. Challenges in connection with peptide formulation development are often over-looked or neglected.

In general, peptides are defined as polypeptides of less than 50 amino residues and are often lacking organised tertiary or globular structure. Some do adopt secondary structures, although this tends to be limited, for example a single turn of an α-helix. While their smaller size makes them easier to deliver across biological barriers than larger proteins, their formulation can be problematic.

Some of the formulation challenges relating to peptides in particular include: chemical instability; adopting multiple conformers; their tendency to self-associate; and a complex physical instability, such as gel formation, amyloid formation and/or precipitation.

The most common challenge is chemical degradation of peptides and proteins, through degradation mechanisms such as deamidation and oxidation. The amino acid sequence of a given peptide defines to what extent it is affected by deamidation and/or oxidation reactions.

Oxidation rates of specific residues, such as Met residues, correlate with the degree of solvent exposure. As peptides do not possess a globular structure that can sequester reactive groups, the side chains of nearly all of the residues in a peptide are fully solvent exposed, allowing maximal contact with reactive oxygen species. Deamidation involves hydrolysis of the amide sidechain of amino acid residues, such as Asn and Gln. Further, the high degree of peptide chain flexibility leads to high rates of deamidation, compared to more complex proteins. It is however important to note that the nature of the amino acid following the deamidation, e.g. the one following Asn, also impacts deamidation rates. A peptides lack of steric bulk and the ability to hydrogen bond to the Asn side chain may even speed up the reaction further. Typically, Asn-Gly, Asn-Ala, Asn-Ser and Asn-Asp amino acid combinations display reaction rates that scientists have to factor in and test to ensure stable pharmaceutical compositions. The greatest control over hydrolytic reactions, including deamidation, is exerted by stable and reliable pH and buffer systems. Such stable and reliable pH and buffer systems will however be affected by additional excipients added to the composition.

For comfort during administration, many dosage forms must be "isotonic" with body fluids at the site of injection, e.g. parenteral, ophthalmic and nasal solutions. Pain and irritation at the site of administration may occur if the formulation is either hypertonic or hypotonic. Further isotonic compositions prevent osmotic shock at the injection site. Each peptide's own tonicity affects the overall tonicity dependent on the total concentration of peptide in the isotonic parenteral pharmaceutical composition and to what extent the tonicity agents need to be supplied to the composition to achieve tonicity. Tonicity is the 'effective osmolality' and is equal to the sum of the concentrations of the solutes, which have the capacity to exert an osmotic force across the membrane. Biologic systems are compatible with solutions having similar osmotic pressures, i.e., an equivalent number of dissolved species, and this is thus desired for medicinal products, which are administered parenterally. For example, red blood cells, blood plasma and 0.9% sodium chloride solution contain approximately the same number of solute particles per unit volume and are termed iso-osmotic and isotonic. If solutions do not contain the same number of dissolved species, i.e., they contain more (hypertonic) or less (hypotonic), then it may be necessary to alter the composition of the solution to bring them into an acceptable range. There is a range of non-ionic and ionic tonicity agents. The non-ionic ones may be selected from dextrose, propylene glycol, glyceryl, mannitol, such as D-mannitol, and sorbitol. The ionic tonicity agents may include, alkali metals or earth metal halides, such as $CaCl_2$, KBr, KCl, LiCl, NaI, NaBr, NaCl, or $Na_2SO_4$.

Hypotonicity and hypertonicity can be addressed by specific selection of excipients and their amount in the formulation. For example, the formulation scientist may increase or decrease the concentration of some components of the formulation to achieve the best possible chemical or physical stability as well as in-use shelf life and other desired properties of medicinal products.

Excipients are added to parenteral formulations to enhance or maintain active ingredient solubility (solubilisers) and/or stability (buffers, antioxidants, chelating agents, cryo- and lyoprotectants). Excipients are in many instances important in parenteral formulations to assure safety (antimicrobial preservatives), minimise pain and irritation upon injection (tonicity agents), and control or prolong drug delivery (polymers). These are all examples of positive or synergistic interactions between excipients and medicinal products. However, any excipient added to the composition has the potential to produce negative effects such as loss of peptide solubility, activity, and/or chemical/physical stability, increased self-aggregation or fibrillation, which in turn may render the medicinal product unsafe for administration.

Thus, the formulation scientist has to investigate and optimise all components in a pharmaceutical composition, considering all interactions, including synergistic and antagonistic, between excipients and drugs in parenteral formulations. The present invention provides a surprisingly stable pharmaceutical composition comprising selected peptides.

The present invention concerns pharmaceutical compositions for parenteral administration of selected peptides disclosed in WO2018104561 (e.g. compound 18 of WO2018104561), which describes the compounds and their uses in detail. Example 4 of WO2018104561 provides test formulations of the compounds it discloses, however, it does not provide any parenteral pharmaceutical composition (e.g. none comprising a tonicity agent).

WO2016066818 discloses GLP-1 agonists, GLP-2 agonists and combinations thereof, and other GLP-1/GLP-2 dual agonists and formulations comprising PBS buffer containing 3% mannitol and 0.6% L-His, which may be suitable for parenteral administration of the disclosed GLP½-dual agonists.

WO2013164484 discloses GLP-2 analogues, and independently lists a series of tonicity agents (i.e. isotonicity makers) and suitable pH buffering agents as well as pH ranges considered suitable for these compounds.

None of these documents discloses the surprisingly stable pharmaceutical composition suitable for parenteral administration according to the present invention.

SUMMARY OF THE INVENTION

This application provides chemically stable parenteral pharmaceutical compositions comprising one or more GLP-1/GLP-2 dual agonist. The application thus provides isotonic pharmaceutical compositions comprising one or more GLP-1/GLP-2 dual agonist comprising general formula A, suitable for parenteral administration to human subjects.

In some aspects, this invention provides a chemically stable parenteral pharmaceutical composition, comprising one or more GLP-1/GLP-2 dual agonist, comprising at least about 1 mg/mL GLP-1/GLP-2 dual agonist comprising general formula A:

H[Aib]EG-X5-F-X7-SELATILD-[ψ]-QAARDFI-
AWLI-X28-X29-KITD          (A) (SEQ ID NO: 2), wherein X5 is T or S; X7 is T or S; X28 is Q, E, A, H, Y, L, K, R or S; X29 is H, Y or Q and at least one of X5 and X7 is T and wherein [ψ]indicates an L or D lysine residue in which the side chain is conjugated to the GLP-1/GLP-2 dual agonist and wherein said side chain is selected from the list consisting of: K([17-carboxy-heptadecanoyl]-isoGlu), K([17-Carboxy-heptadecanoyl]-isoGlu-KEK-Peg3); K([17-carboxy-heptadecanoyl]-isoGlu-Peg3); K([19-Carboxy-nonadecanoyl]-isoGlu); K([19-Carboxy-nonadecanoyl]-iso-Glu-KEK); K([19-Carboxy-nonadecanoyl]-isoGlu-KEK-Peg3); K([19-carboxy-nonadecanoyl]-isoGlu-KEK-Peg3-Peg3); K([19-carboxy-nonadecanoyl]-isoGlu-Peg3-Peg3); K([19-carboxy-nonadecanoyl]-isoLys-Peg3-Peg3-Peg3); K([Hexadecanoyl]-βAla-; K([Hexadecanoyl]-isoGlu); or K(Octadecanoyl) and wherein said composition further comprises about 20-200 mM buffer component, or about 5 mM to about 50 mM of phosphate buffer component, preferably about 10 mM to about 40 mM, more preferably about 15 mM to about 30 mM, and most preferably about 20 mM of phosphate buffer component; and about 1-360 mM of one or more tonicity agent, preferably about 150-250 mM of one or more tonicity agent, wherein said one or more tonicity agent is an ionic or non-ionic tonicity agent, wherein said ionic tonicity agent is selected from salts, alkali metals or earth metal halides, and said non-ionic tonicity agent is mannitol, such as D-mannitol, and wherein said composition has a pH of about pH 7.0 to about pH 8.2.

In some aspects, particular and specific isotonic parenteral compositions are described in detail in the description of the invention and the numbered non-limiting aspects comprised in said description of the invention.

The chemical stability at time point Y of GLP-1/GLP-2 dual agonist in any of the tested compositions disclosed herein can be expressed as the relative purity $X^Y$ of the GLP-1/GLP-2 dual agonist and is determined by measuring the absolute purity X' of the GLP-1/GLP-2 dual agonist and normalising it to the absolute purity $X^o$ of the GLP-1/GLP-2 dual agonist at day zero (day 0), wherein said absolute purities are determined by HPLC at a given time point Y by identifying the purity of peak corresponding to the GLP-1/GLP-2 dual agonist.

It was surprisingly found, that the chemical stability of the disclosed GLP-1/GLP-2 dual agonists in parenteral pharmaceutical compositions, comprising mannitol as a non-ionic tonicity agent, have a stable and high chemical stability compared to pharmaceutical compositions comprising other tonicity agents, such as sucrose, dextrose, glycerol, propylene glycol, and mannitol when in combination with the buffer L-histidine.

It was surprisingly found, that the chemical stability of the disclosed GLP-1/GLP-2 dual agonists in parenteral pharmaceutical compositions comprising ionic tonicity agents, such as NaCl, have a chemical stability which is at least as good as (i.e. comparable to) pharmaceutical compositions not comprising any tonicity agent(s) and a higher normalised stability than compositions comprising other tonicity agents, such as sucrose, dextrose and glycerol.

DESCRIPTION OF THE INVENTION

In some aspects of this invention, there is provided a chemically stable parenteral composition, comprising one or more GLP-1/GLP-2 dual agonist, comprising at least about 1 mg/mL GLP-1/GLP-2 dual agonist comprising general formula A:

H[Aib]EG-X5-F-X7-SELATILD-[ψ]-QAARDFI-
AWLI-X28-X29-KITD          (A) (SEQ ID NO: 2), wherein X5 is T or S; X7 is T or S; X28 is Q, E, A, H, Y, L, K, R or S; X29 is H, Y or Q and at least one of X5 and X7 is T and wherein [ψ]indicates an L or D lysine residue in which the side chain is conjugated to the GLP-1/GLP-2 dual agonist and wherein said side chain is [K([17-carboxy-heptadecanoyl]-isoGlu)]and wherein said composition further comprises about 20-200 mM buffer component, or about 5 mM to about 50 mM of phosphate buffer component, preferably about 10 mM to about 40 mM, more preferably about 15 mM to about 30 mM, and most preferably about 20 mM of phosphate buffer component; and about 1-360 mM of one or more tonicity agent, preferably about 150-250 mM of one or more tonicity agent, wherein said one or more tonicity agent is a non-ionic tonicity agent, which is mannitol, such as D-mannitol, and wherein said composition has a pH of about pH 7.0 to about pH 8.2.

In a preferred aspect, this invention provides an isotonic parenteral pharmaceutical composition, comprising:

a. at least about 1 mg/mL of one or more GLP-1/GLP-2 dual agonist comprising general formula A:

H[Aib]EG-X5-F-X7-SELATILD-[ψ]-QAARDFI-
AWLI-X28-X29-KITD          (A) (SEQ ID NO: 2), wherein X5 is T or S; X7 is T or S; X28 is Q, E, A, H, Y, L, K, R or S; X29 is H and at least one of X5 and X7 is T, and wherein [ψ]indicates an L or D lysine residue in which an albumin binding moiety is conjugated to the GLP-1/ GLP-2 dual agonist, and wherein said albumin binding moiety is [K([17-carboxy-heptadecanoyl]-isoGlu)]; and b. about 5 mM to about 50 mM of phosphate buffer component, preferably about 10 mM to about 40 mM, more preferably about 15 mM to about 30 mM, and most preferably about 20 mM of phosphate buffer component; and c. about 190 mM to about 240 mM of one or more tonicity agent, wherein said one or more tonicity agent is a non-ionic tonicity agent, and wherein the non-ionic tonicity agent is mannitol, wherein said composition further comprises a solvent, and wherein said composition has a pH of about pH 6.0 to about pH 8.2, preferably a pH of about pH 7.0 to about pH 8.0.

In some aspects, this invention provides a chemically stable parenteral composition, comprising one or more GLP-1/GLP-2 dual agonist, comprising at least about 1 mg/mL GLP-1/GLP-2 dual agonist comprising general formula A:

H[Aib]EG-X5-F-X7-SELATILD-[ψ]-QAARDFI-
    AWLI-X28-X29-KITD      (A) (SEQ ID NO: 2), wherein X5 is T or S; X7 is T or S; X28 is Q, E, A, H, Y, L, K, R or S; X29 is H, Y or Q and at least one of X5 and X7 is T and wherein [ψ]indicates an L or D lysine residue in which the side chain is conjugated to the GLP-1/GLP-2 dual agonist and wherein said side chain is [K([17-carboxy-heptadecanoyl]-isoGlu)]and wherein said composition further comprises about 20-200 mM buffer component and about 1-360 mM of one or more tonicity agent, preferably about 150-250 mM of one or more tonicity agent, wherein said one or more tonicity agent is an ionic tonicity agent, selected from the group consisting of salts, alkali metals or earth metal halides and wherein said composition has a pH of about pH 7.0 to about pH 8.2.

In some aspects, this invention provides a chemically stable parenteral composition, comprising one or more GLP-1/GLP-2 dual agonist, comprising at least about 1 mg/mL GLP-1/GLP-2 dual agonist comprising general formula A:

H[Aib]EG-X5-F-X7-SELATILD-[ψ]-QAARDFI-
    AWLI-X28-X29-KITD      (A) (SEQ ID NO: 2), wherein X5 is T or S; X7 is T or S; X28 is Q, E, A, H, Y, L, K, R or S; X29 is H, Y or Q and at least one of X5 and X7 is T and wherein [ψ]indicates an L or D lysine residue in which the side chain is conjugated to the GLP-1/GLP-2 dual agonist and wherein said side chain is [K([17-carboxy-heptadecanoyl]-isoGlu)]and wherein said composition further comprises about 20-200 mM buffer component and about 1-360 mM of one or more tonicity agent, preferably about 150-250 mM of one or more tonicity agent, wherein said one or more tonicity agent is an ionic tonicity agent, selected from the group consisting of CaCl₂, KBr, KCl, LiCl, NaI, NaBr, NaCl, Na₂SO₄, preferably NaCl or KCl, and wherein said composition has a pH of about pH 7.0 to about pH 8.2

In some aspects, said chemical stability of the one or more GLP-1/GLP-2 dual agonist, comprised in an isotonic parenteral pharmaceutical composition of this invention is expressed as the relative purity of the GLP-1/GLP-2 dual agonist peak (i.e. the main peak), determined by HPLC at a given time point, and normalised to the absolute purity of the GLP-1/GLP-2 dual agonist peak (i.e. main peak) at time zero, which is set to 100%. Thus, at time zero, the chemical stability of a GLP-1/GLP-2 dual agonist in said isotonic parenteral pharmaceutical composition of this invention is 100%.

It was surprisingly found, that the chemical stability of said one or more GLP-1/GLP-2 dual agonists comprised in one or more parenteral pharmaceutical compositions of this invention, wherein said one or more tonicity agent is selected from salts and/or mannitol, such as D-mannitol, as disclosed in aspects of this invention, have a stable and high chemical stability compared to pharmaceutical compositions comprising other tonicity agents, such as sucrose, dextrose, glycerol, propylene glycol, and mannitol when in combination with the buffer L-histidine.

It was surprisingly found, that the chemical stability of said one or more GLP-1/GLP-2 dual agonists comprised in one or more parenteral pharmaceutical compositions of this invention, wherein mannitol, such as D-mannitol is selected as the tonicity agent as disclosed in aspects of this invention, have a stable and higher chemical stability compared to pharmaceutical compositions comprising other tonicity agents, such as sucrose, dextrose, glycerol, propylene glycol, and mannitol when in combination with the buffer L-histidine.

It was surprisingly found, that the chemical stability of said one or more GLP-1/GLP-2 dual agonists comprised in one or more parenteral pharmaceutical compositions of this invention, comprising salt, such as NaCl as the tonicity agent, have a chemical stability which is at least as good as (i.e. comparable to) pharmaceutical compositions not comprising any tonicity agent(s) and a higher normalised stability than compositions comprising other tonicity agents, such as sucrose, dextrose and glycerol.

Compounds

In some aspects, said GLP-1/GLP-2 dual agonist comprising general formula A is of the general formula B:

H[Aib]EG-X5-FT-SELATILD-[ψ]-QAARDFIAWLI-
    X28-HKITD      (B) (SEQ ID NO: 3), wherein X5 is T or S; X28 is Q, E, A, H, Y, L, K, R or S and wherein [ψ]indicates an L or D lysine residue in which the side chain is conjugated to the GLP-1/GLP-2 dual agonist and wherein said side chain is [K([17-carboxy-heptade-canoyl]-isoGlu)].

In some aspects, said one or more GLP-1/GLP-2 dual agonist comprising formula A, comprised in one or more parenteral pharmaceutical compositions of this invention, is: H[Aib]EGSFTSELATILD[ψ]QAARDFIAWLIQHKITD (SEQ ID NO: 1).

In some aspects, said one or more GLP-1/GLP-2 dual agonist comprising formula A, comprised in one or more parenteral pharmaceutical compositions of this invention, is: Hy-H[Aib]EGSFTSELATILD[K([17-carboxy-heptade-canoyl]-isoGlu)]QAARDFIAWLIQHKITD-OH (CPD1OH) (SEQ ID NO: 1), or any pharmaceutical acceptable salt thereof.

In some aspects, said one or more GLP-1/GLP-2 dual agonist comprising formula A, comprised in one or more parenteral pharmaceutical compositions of this invention, is: Hy-H[Aib]EGSFTSELATILD[K([17-carboxy-heptadecanoyl]-isoGlu)]QAARDFIAWLIQHKITD-NH$_2$ (CPD1 NH$_2$) (SEQ ID NO: 1), or any pharmaceutical acceptable salt thereof.

In some aspects, said one or more GLP-1/GLP-2 dual agonist comprising formula A, comprised in one or more parenteral pharmaceutical compositions of this invention, is CPD1 OH or any pharmaceutical acceptable salt thereof. In some aspects, the pharmaceutically acceptable salt of CPD1OH is a chloride salt.

In some aspects said one or more GLP-1/GLP-2 dual agonist comprising formula A, comprised in one or more parenteral pharmaceutical compositions of this invention, is CPD1 NH$_2$ or any pharmaceutical acceptable salt thereof. In some aspects, the pharmaceutically acceptable salt of CPD1 NH$_2$ is a chloride salt.

In a preferred aspect said one or more GLP-1/GLP-2 dual agonist is CPD1OH or any pharmaceutical acceptable salt thereof, preferably a chloride salt thereof.

TABLE 1

Selected GLP-1/GLP-2 dual agonist comprised in one or more parenteral composition of this invention

| SEQ ID | CPD | CPD form | Compound |
|---|---|---|---|
| 1 | 1 | 1OH | Hy-H[Aib]EGSFTSELATILD[K([17-carboxy-heptadecanoyl]-isoGlu)]QAARDFIAWLIQHKITD-OH or any acceptable pharmaceutical salt thereof. |
| 1 | 1 | 1NH$_2$ | Hy-H[Aib]EGSFTSELATILD[K([17-carboxy-heptadecanoyl]-isoGlu)]QAARDFIAWLIQHKITD-NH$_2$ or any acceptable pharmaceutical salt thereof. |

Thus, the abbreviation CPD1 refers to any form of the compound comprising SEQ ID NO: 1, however CPD1OH solely discloses the compound comprising SEQ ID NO: 1, wherein said compound is in its—OH form (free acid). CPD1 NH$_2$ form refers to the compounds —NH$_2$ form (amidated form). Both CPD1 OH and CPD1 NH$_2$ can be converted into a pharmaceutical acceptable salt to provide a drug substance in powder form.

TABLE 2

Amino acid sequence comprised in one or more GLP-1/GLP-2 dual agonist of the present invention

| SEQ ID | Sequence | Variables |
|---|---|---|
| 1 | H[Aib]EGSFTSELATILD[Ψ]QAARDFIAWLIQHKITD | None |
| 2 (Formula A) | H[Aib]EG-X5-F-X7-SELATILD-[Ψ]-QAARDFIAWLI-X28-X29-KITD | X5 is T, S; X7 is T or S; X28 is Q, E, A, H, Y, L, K, R or S; X29 is H, Y or Q |
| 3 (Formula B) | H[Aib]EG-X5-FT-SELATILD-[Ψ]-QAARDFIAWLI-X28-HKITD | X5 is T, S; X28 is Q, E, A, H, Y, L, K, R or S |

Tonicity and Tonicity Agents

In some aspects, said isotonic parenteral pharmaceutical composition of this invention comprising one or more GLP-1/GLP-2 dual agonist comprising formula A or B is isotonic. In some embodiments, the osmolality of the compositions as described herein is about 300±120 mOsmol/kg. In some embodiments, the osmolality of the compositions as described herein is about 290±70 mOsmol/kg. In some embodiments, the osmolality of the compositions as described herein is about 280 mOsmol/kg to about 320 mOsmol/kg. In some embodiments the osmolality of the compositions as described herein is about 290 mOsmol/kg to about 320 mOsmol/kg.

In some aspects, said isotonic parenteral pharmaceutical composition of this invention comprising one or more GLP-1/GLP-2 dual agonist comprising SEQ ID NO: 1 is isotonic.

In some aspects, said one or more tonicity agent, comprised in a parenteral pharmaceutical composition of this invention, is a non-ionic tonicity agent, which is mannitol, such as D-mannitol.

In some aspects, said one or more tonicity agent, comprised in one or more parenteral pharmaceutical compositions of this invention, is an ionic tonicity agent, such as salts, alkali metals or earth metal halides. In some aspects, said ionic tonicity agent is selected from the list consisting of: CaCl$_2$, KBr, KCl, LiCl, NaI, NaBr, NaCl or Na$_2$SO$_4$. In some aspects, said one or more tonicity agent, comprised in one or more parenteral pharmaceutical compositions of this invention, is an ionic tonicity agent, which is a salt, such as NaCl. In some aspects, said one or more tonicity agent, comprised in one or more parenteral pharmaceutical compositions of this invention, is an ionic tonicity agent, which is a salt, such as KCl.

In some aspects, said one or more tonicity agent, comprised in one or more parenteral pharmaceutical compositions of this invention is a mixture of an ionic and non-ionic tonicity agent, such as a mixture of a salt and mannitol, such as D-mannitol.

In a preferred aspect of this invention, the tonicity agent comprises mannitol, preferably D-mannitol.

In a preferred aspect of this invention, the tonicity agent consists of mannitol, preferably D-mannitol.

In a preferred aspect of this invention, the tonicity agent is mannitol, preferably D-mannitol.

In some aspects, said one or more tonicity agent, comprised in one or more parenteral pharmaceutical compositions of this invention, is mannitol, such as D-mannitol, and is present in the isotonic parenteral pharmaceutical composition at a final concentration of about 150 mM to about 360 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 150 mM to about 300 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 150 mM to about 250 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 210 mM to about 240 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 210 mM to about 230 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 360 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 300 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 250 mM. In some aspects, said one or more tonicity agent, comprised in one or more parenteral pharmaceutical compositions of this invention, is mannitol, such as D-mannitol, and is present in the isotonic parenteral pharmaceutical composition at a final concentration of about 230 mM.

In a preferred aspect, mannitol is present in the isotonic parenteral pharmaceutical composition at a final concentration of about 190 mM to about 240 mM, preferably about 230 mM. Preferably, the mannitol is D-mannitol.

In some aspects, said one or more tonicity agent, comprised in one or more parenteral pharmaceutical compositions of this invention, is NaCl or KCl, and is present in the isotonic parenteral pharmaceutical composition at a final concentration of about 50 mM to about 250 mM. In some aspects, said one or more tonicity agent, comprised in one or more parenteral pharmaceutical compositions of this invention, is NaCl or KCl, and is present in the isotonic parenteral pharmaceutical composition at a final concentration of about 150 mM to about 200 mM. In some aspects, said one or more tonicity agent, comprised in one or more parenteral pharmaceutical compositions of this invention, is NaCl or KCl, and is present in the isotonic parenteral pharmaceutical composition at a final concentration of about 200 mM to about 250 mM.

Buffer

In some aspects, the buffer component is selected from the group consisting of phosphate buffer, citrate buffer, histidine buffer or tris buffer, or a combination thereof.

In some aspects, the buffer component is selected from the group consisting of phosphate buffer, citrate buffer, or tris buffer, or a combination thereof.

In some aspects, the buffer component may be selected from the group consisting of phosphate buffer, tris buffer, or a combination thereof.

In some aspects, the buffer component, comprised in one or more parenteral pharmaceutical compositions of this invention, is a phosphate buffer. In some aspects, said buffer component, comprised in one or more parenteral pharmaceutical compositions of this invention, is a sodium phosphate buffer.

In some aspects, the buffer component, comprised in one or more parenteral pharmaceutical compositions of this invention, is a phosphate buffer. In some aspects, said buffer component, comprised in one or more parenteral pharmaceutical compositions of this invention, is a sodium phosphate buffer, such as $Na_2HPO_4$.

In some aspects, the buffer component, comprised in one or more parenteral pharmaceutical compositions of this invention, is a phosphate buffer and wherein said phosphate buffer is present in the isotonic parenteral pharmaceutical composition at a final concentration of about 1 mM to about 200 mM, for example about 15 mM to about 200 mM. or about 15 mM to about 15 to 25 mM. Said final concentration may be about 2 mM to about 190 mM, about 3 mM to about 180 mM, about 4 mM to about 170 mM, about 5 mM to about 160 mM, about 6 mM to about 150 mM, about 7 mM to about 140 mM, about 8 mM to about 140 mM, about 9 mM to about 130 mM, about 10 mM to about 120 mM, about 11 mM to about 100 mM, about 12 mM to about 80 mM, about 13 mM to about 60 mM, about 14 mM to about 40 mM, about 15 mM to about 30 mM, about 16 mM to about 27 mM, about 17 mM to about 25 mM, or about 18 mM to about 23 mM. In some aspects, said buffer component, comprised in one or more parenteral pharmaceutical compositions of this invention, is a phosphate buffer and wherein said phosphate buffer is present in the isotonic parenteral pharmaceutical composition at a final concentration of about 20 mM. In some aspects, said buffer component, comprised in one or more parenteral pharmaceutical compositions of this invention, is a phosphate buffer and wherein said phosphate buffer is present in the isotonic parenteral pharmaceutical composition at a final concentration of about 100 mM.

In a preferred aspect said phosphate buffer is present in the isotonic parenteral pharmaceutical composition at a final concentration of about 15 mM to about 30 mM.

Preferably said phosphate buffer is present in the isotonic parenteral pharmaceutical composition at a final concentration of about 5 mM to about 50 mM, preferably about 10 mM to about 40 mM, more preferably about 15 mM to about 30 mM, and most preferably about 20 mM.

In a preferred aspect said buffer is a phosphate buffer, preferably a sodium phosphate buffer, more preferably disodium phosphate, sodium dihydrogen phosphate, or a combination thereof.

In one aspect disodium phosphate is present in the isotonic parenteral pharmaceutical composition at a final concentration of about 15 mM to about 19 mM, preferably between 18 mM and 19 mM.

In one aspect sodium dihydrogen phosphate is present in the isotonic parenteral pharmaceutical composition at a final concentration of about 1 mM to about 3 mM, preferably between 1 mM and 2 mM.

In one aspect the disodium phosphate and sodium dihydrogen phosphate buffer components together are at a final concentration of about 5 mM to about 50 mM, preferably about 10 mM to about 40 mM, more preferably about 15 mM to about 30 mM.

In a most preferred aspect the disodium phosphate and sodium dihydrogen phosphate buffer components together are at a final concentration of about 20 mM.

In some aspects the buffer is not a histidine buffer and/or does not contain histidine, such as L-histidine.

In some aspects, the pH of an isotonic parenteral pharmaceutical composition of this invention, is between about pH 6.0 and about pH 8.2, preferably between about pH 7.0 to about pH 8.0. In some aspects, said pH of an isotonic parenteral pharmaceutical composition of this invention, is between about pH 7.0 to about pH 8.0. In some aspects, said pH of an isotonic parenteral pharmaceutical composition of this invention, is about pH 7.0. In some aspects, said pH of an isotonic parenteral pharmaceutical composition of this invention, is about pH 8.0. In some aspects, said pH of an isotonic parenteral pharmaceutical composition of this invention, is about pH 8.2. In some aspects, said pH of an isotonic parenteral pharmaceutical composition of this invention, is about pH 6.0. In some aspects, said pH of an isotonic parenteral pharmaceutical composition of this invention, is between about pH 7.0 and about pH 8.2, preferably about pH 7.5 or about pH 8.2. In some aspects, said pH of an isotonic parenteral pharmaceutical composition of this invention, is between about pH 7.0 and about pH 8.2, preferably about pH 7.6 or about 8.0. In some aspects, said pH of an isotonic parenteral pharmaceutical composition of this invention, is between about pH 7.0 and about pH 8.2, preferably about pH 7.6 or about pH 7.7. In some aspects, said pH of an isotonic parenteral pharmaceutical composition of this invention, is between about pH 7.0 and about pH 8.2, preferably about pH 7.6. In some aspects, said pH of an isotonic parenteral pharmaceutical composition of this invention, is between about pH 7.0 and about pH 8.2, preferably about pH 8.0. In some aspects, said pH of an isotonic parenteral pharmaceutical composition of this invention, is between about pH 7.0 and about pH 8.2, preferably about pH 7.0.

In a preferred aspect the pH is about pH 8.0.

In some aspects, in an isotonic parenteral pharmaceutical composition of this invention, said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist comprises an amino acid sequence of formula A, wherein the pH is between about pH 7.0 and about pH 8.0, preferably about pH 8.0. In some aspects, in an isotonic parenteral pharmaceutical composition of this invention, said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist comprises an amino acid sequence of formula B, wherein the pH is between about pH 7.0 and about pH 8.0, preferably about pH 8.0.

In some aspects, in an isotonic parenteral pharmaceutical composition of this invention, said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist comprises an amino acid sequence of SEQ ID NO: 1, wherein the pH is between about pH 7.0 and about pH 8.0, preferably about pH 8.0.

In some aspects, in an isotonic parenteral pharmaceutical composition of this invention, said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist is CPD1 OH, wherein the pH is between about pH 7.0 and about pH 8.0, preferably about pH 8.0.

In some aspects, in an isotonic parenteral pharmaceutical composition of this invention, said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist is a salt of CPD1, wherein the pH is between about pH 7.0 and about pH 8.0, preferably about pH 8.0.

In some aspects, in an isotonic parenteral pharmaceutical composition of this invention, said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist is a chloride salt of CPD1, wherein the pH is between about pH 7.0 and about pH 8.0, preferably about pH 8.0.

In some aspects, in an isotonic parenteral pharmaceutical composition of this invention, said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist is CPD1 $NH_2$, wherein the pH is between about pH 7.0 and about pH 8.0, preferably about pH 8.0. In some aspects, the composition of this invention comprises the below listed ingredients:

| Component | Function |
| --- | --- |
| CPD1 | Drug substance |
| Phosphate buffer | Buffer component |
| $NaH_2PO_4$ | Buffer component |
| Sodium dihydrogen phosphate, anhydrous/ Monobasic sodium phosphate, anhydrous | |
| Mannitol (D-mannitol) | Tonicity agent |
| Hydrochloric acid | pH adjustment |
| Sodium Hydroxide | pH adjustment |
| Water for Injections | Solvent | wherein CPD1 is a pharmaceutically acceptable salt of CPD1.

In some aspects, the composition of this invention comprises the below listed ingredients:

| Component | Function |
| --- | --- |
| CPD1 | Drug substance |
| Disodium phosphate, anhydrous/Dibasic sodium phosphate, anhydrous (such as $Na_2HPO_4$) | Buffer component |
| $NaH_2PO_4$ | Buffer component |
| Sodium dihydrogen phosphate, anhydrous/ Monobasic sodium phosphate, anhydrous | |
| Mannitol (D-mannitol) | Tonicity agent |
| Hydrochloric acid | pH adjustment |
| Sodium Hydroxide | pH adjustment |
| Water for Injections | Solvent | wherein CPD1 is a pharmaceutically acceptable salt of CPD1.

Concentration of Compound

In some aspects, an isotonic parenteral pharmaceutical composition of this invention comprises at least about 1 mg/mL to about 15 mg/mL GLP-1/GLP-2 dual agonist. In some aspects, an isotonic parenteral pharmaceutical composition of this invention comprises at least about 1 mg/mL GLP-1/GLP-2 dual agonist. In some aspects, an isotonic parenteral pharmaceutical composition of this invention comprises at least about 2 mg/mL GLP-1/GLP-2 dual agonist. In some aspects, an isotonic parenteral pharmaceutical composition of this invention comprises about 2 mg/mL GLP-1/GLP-2 dual agonist.

In some aspects, an isotonic parenteral pharmaceutical composition of this invention comprises about 2 mg/mL GLP1/GLP-2 dual agonist and said one or more GLP-1/GLP-2 dual agonist is comprised of formula A. In some aspects, an isotonic parenteral pharmaceutical composition of this invention comprises about 2 mg/mL to about 10 mg/mL GLP-1/GLP-2 dual agonist. In some aspects, an isotonic parenteral pharmaceutical composition of this invention comprises about 2 mg/mL to about 10 mg/mL GLP1/GLP-2 dual agonist and said one or more GLP-1/GLP-2 dual agonist is comprised of formula A. In some aspects, an isotonic parenteral pharmaceutical composition of this invention comprises about 10 mg/mL GLP-1/GLP-2 dual agonist. In some aspects, an isotonic parenteral pharmaceutical composition of this invention comprises about 10 mg/mL GLP1/GLP-2 dual agonist and said one or more GLP-1/GLP-2 dual agonist is comprised of formula A.

In some aspects, an isotonic parenteral pharmaceutical composition of this invention comprises about 2 mg/mL GLP1/GLP-2 dual agonist and said one or more GLP-1/GLP-2 dual agonist is comprised of formula B. In some aspects, an isotonic parenteral pharmaceutical composition of this invention comprises about 2 mg/mL to about 10 mg/mL GLP-1/GLP-2 dual agonist. In some aspects, an isotonic parenteral pharmaceutical composition of this invention comprises about 2 mg/mL to about 10 mg/mL GLP1/GLP-2 dual agonist and said one or more GLP-1/GLP-2 dual agonist is comprised of formula B. In some aspects, an isotonic parenteral pharmaceutical composition of this invention comprises about 10 mg/mL GLP-1/GLP-2 dual agonist. In some aspects, an isotonic parenteral pharmaceutical composition of this invention comprises about 10 mg/mL GLP1/GLP-2 dual agonist and said one or more GLP-1/GLP-2 dual agonist is comprised of formula B.

In some aspects, an isotonic parenteral pharmaceutical composition of this invention comprises about 2 mg/mL GLP1/GLP-2 dual agonist and said one or more GLP-1/GLP-2 dual agonist is CPD1OH. In some aspects, an isotonic parenteral pharmaceutical composition of this invention comprises about 2 mg/mL to about 10 mg/mL GLP-1/GLP-2 dual agonist. In some aspects, an isotonic parenteral pharmaceutical composition of this invention comprises about 2 mg/mL to about 10 mg/mL GLP1/GLP-2 dual agonist and said one or more GLP-1/GLP-2 dual agonist is CPD1OH. In some aspects, an isotonic parenteral pharmaceutical composition of this invention comprises about 10 mg/mL GLP-1/GLP-2 dual agonist. In some aspects, an isotonic parenteral pharmaceutical composition of this invention comprises about 10 mg/mL GLP1/GLP-2 dual agonist and said one or more GLP-1/GLP-2 dual agonist is CPD1OH.

In some aspects, an isotonic parenteral pharmaceutical composition of this invention comprises about 2 mg/mL GLP1/GLP-2 dual agonist and said one or more GLP-1/GLP-2 dual agonist is CPD1 $NH_2$. In some aspects, an isotonic parenteral pharmaceutical composition of this invention comprises about 2 mg/mL to about 10 mg/mL GLP-1/GLP-2 dual agonist. In some aspects, an isotonic parenteral pharmaceutical composition of this invention comprises about 2 mg/mL to about 10 mg/mL GLP1/GLP-2 dual agonist and said one or more GLP-1/GLP-2 dual agonist is CPD1$NH_2$. In some aspects, an isotonic parenteral pharmaceutical composition of this invention comprises about 10 mg/mL GLP-1/GLP-2 dual agonist. In some aspects, an isotonic parenteral pharmaceutical composition of this invention comprises about 10 mg/mL GLP1/GLP-2 dual agonist and said one or more GLP-1/GLP-2 dual agonist is CPD1 $NH_2$.

In a preferred aspect an isotonic parenteral pharmaceutical composition of this invention comprises about 2 mg/mL to about 10 mg/mL GLP-1/GLP-2 dual agonist.

Preservative

In some aspects, an isotonic parenteral pharmaceutical composition does not comprise a preservative.

In some aspects, an isotonic parenteral pharmaceutical composition does comprise a preservative.

Indications

In some aspects, a pharmaceutical composition of this invention is administered to human subjects in the need of prophylaxis or treatment of intestinal damage and dysfunction, regulation of body weight, and prophylaxis or treatment of metabolic dysfunction.

In some aspects, a pharmaceutical composition of this invention is administered to human subjects in the need of prophylaxis or treatment of malabsorption, ulcers (e.g. peptic ulcers, Zollinger-Ellison Syndrome, drug-induced ulcers, and ulcers related to infections or other pathogens), short-bowel syndrome, cul-de-sac syndrome, inflammatory bowel disease (Crohns disease and ulcerative colitis), irritable bowel syndrome (IBS), pouchitis, celiac sprue (for example arising from gluten induced enteropathy or celiac disease), tropical sprue, hypogammaglobulinemic sprue, mucositis induced by chemotherapy or radiation therapy, diarrhoea induced by chemotherapy or radiation therapy, low grade inflammation, metabolic endotoxemia, necrotising entero-colitis, primary biliary cirrhosis, hepatitis, fatty liver disease (including parental nutrition associated gut atrophy, PNALD (Parenteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD).

In some aspects, a pharmaceutical composition of this invention is administered to human subjects in the need of prophylaxis or treatment of obesity, morbid obesity, obesity-linked gallbladder disease, obesity-induced sleep apnoea, inadequate glucose control, glucose tolerance, dyslipidaemia (e.g. elevated LDL levels or reduced HDL/LDL ratio), diabetes (e.g. Type 2 diabetes, gestational diabetes), pre-diabetes, metabolic syndrome or hypertension.

In some aspects, a pharmaceutical composition of this invention is administered to human subjects to facilitate biological effects selected from the group consisting of: increasing intestinal mass, improving intestinal function (especially intestinal barrier function), increasing intestinal blood flow, repairing intestinal damage or dysfunction in a subject in need thereof.

In some aspects, a pharmaceutical composition of this invention is administered to human subjects in the need of prophylaxis or treatment of intestinal dysfunction or damage caused by or associated with GVHD, as well as prophylaxis or treatment of side effects such as diarrhoea caused by or associated with GVHD.

In some aspects, a pharmaceutical composition of this invention is administered to human subjects in the need prophylaxis or treatment of obesity, morbid obesity, obesity-linked gallbladder disease and obesity-induced sleep apnoea.

In some aspects, a pharmaceutical composition of this invention is administered to human subjects in the need of improving glucose tolerance and/or glucose control. In some aspects, a pharmaceutical composition of this invention is administered to human subjects in the need of modulating (e.g. improving) circulating cholesterol levels, being capable of lowering circulating triglyceride or LDL levels, and increasing HDL/LDL ratio.

Administration

In some aspects, a pharmaceutical composition of this invention is an aqueous composition.

In some aspects, a pharmaceutical composition of this invention is suitable for parenteral administration performed by subcutaneous, intramuscular or intravenous injection by means of a syringe, optionally a pen-like syringe. In some aspects, a pharmaceutical composition of this invention is suitable for s.c. or i.v. injection into patients.

In some aspects, the present isotonic pharmaceutical parenteral composition is suitable for a single dose administration. In some aspects, the present isotonic pharmaceutical parenteral composition, comprising preservative, is suitable for a multi dose administration.

Functional properties

All chemical stabilities referred to below in this section may be measured and determined by HPLC, such as RP-HPLC according to ASSAY Ill or other equivalent methods.

In some aspects, the pharmaceutical compositions of this invention lead to a chemical stability of said one or more GLP-1/GLP-2 dual agonist, such as CPD1 or any pharmaceutically acceptable salt thereof, of about 100% at day 3 (D3). In some aspects, the pharmaceutical compositions of this invention lead to a chemical stability of said one or more GLP-1/GLP-2 dual agonist, such as CPD1 or any pharmaceutically acceptable salt thereof, of about 99% or higher at day 3 (D3). In some aspects, the pharmaceutical compositions of this invention lead to a chemical stability of said one or more GLP-1/GLP-2 dual agonist, such as CPD1 or any pharmaceutically acceptable salt thereof, of about 99% at day 3 (D3).

In some aspects, the pharmaceutical compositions of this invention lead to a chemical stability of said one or more GLP-1/GLP-2 dual agonist, such as CPD1 or any pharmaceutically acceptable salt thereof, of about 99% at day 7 (D7). In some aspects, the pharmaceutical compositions of this invention lead to a chemical stability of said one or more GLP-1/GLP-2 dual agonist, such as CPD1 or any pharmaceutically acceptable salt thereof, of about 98% or higher at day 7 (D7). In some aspects, the pharmaceutical compositions of this invention lead to a chemical stability of said one or more GLP-1/GLP-2 dual agonist, such as CPD1 or any pharmaceutically acceptable salt thereof, of about 98% at day 7 (D7).

In some aspects, the pharmaceutical compositions of this invention lead to a chemical stability of said one or more GLP-1/GLP-2 dual agonist, such as CPD1 or any pharmaceutically acceptable salt thereof, of about 97.5% at day 7 (D7).

In some aspects, the pharmaceutical compositions of this invention lead to a chemical stability of said one or more GLP-1/GLP-2 dual agonist, such as CPD1 or any pharmaceutically acceptable salt thereof, of about 98% at day 14 (D14). In some aspects, the pharmaceutical compositions of this invention lead to a chemical stability of said one or more GLP-1/GLP-2 dual agonist, such as CPD1 or any pharmaceutically acceptable salt thereof, of about 97% or higher at day 14 (D14). In some aspects, the pharmaceutical compositions of this invention lead to a chemical stability of said one or more GLP-1/GLP-2 dual agonist, such as CPD1 or any pharmaceutically acceptable salt thereof, of about 96% at day 14 (D14). In some aspects, the pharmaceutical compositions of this invention lead to a chemical stability of said one or more GLP-1/GLP-2 dual agonist, such as CPD1 or any pharmaceutically acceptable salt thereof, of about 96.5% at day 14 (D14).

In some aspects, the pharmaceutical compositions of this invention lead to a chemical stability of said one or more GLP-1/GLP-2 dual agonist, such as CPD1 or any pharmaceutically acceptable salt thereof, of about 97% at day 24 (D24). In some aspects, the pharmaceutical compositions of this invention lead to a chemical stability of said one or more GLP-1/GLP-2 dual agonist, such as CPD1 or any pharmaceutically acceptable salt thereof, of about 96% or higher at day 24 (D24). In some aspects, the pharmaceutical compositions of this invention lead to a chemical stability of said one or more GLP-1/GLP-2 dual agonist, such as CPD1 or any pharmaceutically acceptable salt thereof, of about 96% at day 24 (D24). In some aspects, the pharmaceutical compositions of this invention lead to a chemical stability of said one or more GLP-1/GLP-2 dual agonist, such as CPD1 or any pharmaceutically acceptable salt thereof, of about 95.5% at day 24 (D24).

In no aspect, does the isotonic parenteral pharmaceutical composition of this invention lead to a chemical stability, of said one or more GLP-1/GLP-2 dual agonist, such as CPD1 or any pharmaceutically acceptable salt thereof, of below 94.5% on day 24 (D24). In no aspect, does the isotonic parenteral pharmaceutical composition of this invention lead to a chemical stability of said one or more GLP-1/GLP-2 dual agonist, such as CPD1 or any pharmaceutically acceptable salt thereof, of below 60% on day 24 (D24). In no aspect, does the isotonic parenteral pharmaceutical composition of this invention lead to a chemical stability of said one or more GLP-1/GLP-2 dual agonist, such as CPD1 or any pharmaceutically acceptable salt thereof, of below 50% on day 24 (D24).

In some aspects, the pharmaceutical compositions of this invention lead to a chemical stability of said one or more GLP-1/GLP-2 dual agonist, such as CPD1 or any pharmaceutically acceptable salt thereof, of about 100% at month 1 (M1). In some aspects, the pharmaceutical compositions of this invention lead to a chemical stability of said one or more GLP-1/GLP-2 dual agonist, such as CPD1 or any pharmaceutically acceptable salt thereof, of about 99% or higher at month 1 (M1). In some aspects, the pharmaceutical compositions of this invention lead to a chemical stability of said one or more GLP-1/GLP-2 dual agonist, such as CPD1 or any pharmaceutically acceptable salt thereof, of about 99% at month 1 (M1).

In some aspects, the pharmaceutical compositions of this invention lead to a chemical stability of said one or more GLP-1/GLP-2 dual agonist, such as CPD1 or any pharmaceutically acceptable salt thereof, of about 100% at month 2 (M2). In some aspects, the pharmaceutical compositions of this invention lead to a chemical stability of said one or more GLP-1/GLP-2 dual agonist, such as CPD1 or any pharmaceutically acceptable salt thereof, of about 99% or higher at month 2 (M2). In some aspects, the pharmaceutical compositions of this invention lead to a chemical stability of said one or more GLP-1/GLP-2 dual agonist, such as CPD1 or any pharmaceutically acceptable salt thereof, of about 99% at month 2 (M2).

In some aspects, the pharmaceutical compositions of this invention lead to a chemical stability of said one or more GLP-1/GLP-2 dual agonist, such as CPD1 or any pharmaceutically acceptable salt thereof, of about 100% at month 3 (M3). In some aspects, the pharmaceutical compositions of this invention lead to a chemical stability of said one or more GLP-1/GLP-2 dual agonist, such as CPD1 or any pharmaceutically acceptable salt thereof, of about 98% or 99% or higher at month 3 (M3). In some aspects, the pharmaceutical compositions of this invention lead to a chemical stability of said one or more GLP-1/GLP-2 dual agonist, such as CPD1 or any pharmaceutically acceptable salt thereof, of about 98% or 99% at month 3 (M3).

In some aspects, the pharmaceutical compositions of this invention lead to a chemical stability of said one or more GLP-1/GLP-2 dual agonist, such as CPD1 or any pharmaceutically acceptable salt thereof, of about 100% at month 4 (M4). In some aspects, the pharmaceutical compositions of this invention lead to a chemical stability of said one or more GLP-1/GLP-2 dual agonist of about 99% or higher at month 4 (M4). In some aspects, the pharmaceutical compositions of this invention lead to a chemical stability of said one or more GLP-1/GLP-2 dual agonist of about 99% at month 4 (M4).

In some aspects, the pharmaceutical compositions of this invention lead to a chemical stability of said one or more GLP-1/GLP-2 dual agonist, such as CPD1 or any pharmaceutically acceptable salt thereof, of about 100% at month 6 (M6). In some aspects, the pharmaceutical compositions of this invention lead to a chemical stability of said one or more GLP-1/GLP-2 dual agonist, such as CPD1 or any pharmaceutically acceptable salt thereof, of about 94% or 96% or higher at month 6 (M6). In some aspects, the pharmaceutical compositions of this invention lead to a chemical stability of said one or more GLP-1/GLP-2 dual agonist, such as CPD1 or any pharmaceutically acceptable salt thereof, of about 94% or 96% at month 6(M6).

In some aspects, the pharmaceutical compositions of this invention lead to a chemical stability of said one or more GLP-1/GLP-2 dual agonist, such as CPD1 or any pharmaceutically acceptable salt thereof, of about 100% at month 9 (M9). In some aspects, the pharmaceutical compositions of this invention lead to a chemical stability of said one or more GLP-1/GLP-2 dual agonist, such as CPD1 or any pharmaceutically acceptable salt thereof, of about 94% or higher at month 9 (M9). In some aspects, the pharmaceutical compositions of this invention lead to a chemical stability of said one or more GLP-1/GLP-2 dual agonist, such as CPD1 or any pharmaceutically acceptable salt thereof, of about 94% at month 9 (M9).

In some aspects, the pharmaceutical compositions of this invention lead to a chemical stability of said one or more GLP-1/GLP-2 dual agonist, such as CPD1 or any pharmaceutically acceptable salt thereof, of about 97% or 98% or more at month 12 (M12).

In some aspects, the pharmaceutical compositions of this invention lead to a chemical stability of said one or more GLP-1/GLP-2 dual agonist, such as CPD1 or any pharmaceutically acceptable salt thereof, of about 91% or 94% or higher at month 12 (M12).

In some aspects, the pharmaceutical compositions of this invention lead to a chemical stability of said one or more GLP-1/GLP-2 dual agonist, such as CPD1 or any pharmaceutically acceptable salt thereof, of about 91% or 94% at month 12 (M12).

In some aspects, the pharmaceutical compositions of this invention lead to a chemical stability of said one or more GLP-1/GLP-2 dual agonist, such as CPD1 or any pharmaceutically acceptable salt thereof, of about 98% or 99% or more at month 24 (M24).

In some aspects, the pharmaceutical compositions of this invention lead to a chemical stability of said one or more GLP-1/GLP-2 dual agonist, such as CPD1 or any pharmaceutically acceptable salt thereof, of about 98% or 99% at month 24 (M24).Said chemical stability may be at a storage temperature of about 5° C. or about 25° C., preferably 5° C.

In a preferred aspect said chemical stability is about 91% or higher at month 12. Preferably said chemical stability is about 97% or 98% at month 12 at a storage temperature of about 5° C.

In a preferred aspect said chemical stability is about 91% or higher at month 12. Preferably said chemical stability is about 91% or 94% at month 12 at a storage temperature of about 25° C.

In a preferred aspect said chemical stability is about 98% or higher at month 24. Preferably said chemical stability is about 98% or 99% at month 24 at a storage temperature of about 5° C.

In some embodiments, the isotonic pharmaceutical parenteral composition described herein renders said one or more GLP-1/GLP-2 dual agonist, such as CPD1 or any pharmaceutically acceptable salt thereof, predominantly in its trimer form.

In some embodiments, the isotonic pharmaceutical parenteral composition described herein has good or improved stability. Stability may be improved relative to an equivalent composition which does not comprise mannitol as the tonicity agent.

In some embodiments, the isotonic pharmaceutical parenteral composition described herein has good or improved chemical stability. Chemical stability may be improved relative to an equivalent composition which does not comprise mannitol as the tonicity agent.

In some embodiments, the isotonic pharmaceutical parenteral composition described herein has good or improved relative purity. Relative purity may be improved relative to an equivalent composition which does not comprise mannitol as the tonicity agent.

In some embodiments, the isotonic pharmaceutical parenteral composition described herein has physical stability.

In one aspect, the invention provides a method for improving the stability, chemical stability, relative purity and/or physical stability of a pharmaceutical composition comprising any of the GLP-1/GLP-2 dual agonists described herein, wherein said method comprising adding mannitol, preferably D-mannitol, to said composition as the tonicity agent as described herein. The composition may also comprise any of the buffer components described herein.

The composition may also comprise any of the pH adjusters and/or solvents as described herein.

The invention also provides use of mannitol, preferably D-mannitol, as described herein for improving the stability, chemical stability, relative purity and/or physical stability of a composition comprising any of the GLP-1/GLP-2 dual agonists described herein. The composition may also comprise any of the buffer components described herein. The composition may also comprise any of the pH adjusters and/or solvents as described herein.

Said improvement may be relative to a composition not comprising mannitol, preferably D-mannitol, as tonicity agent.

Biological Activity

In some aspects, peptides comprised in pharmaceutical compositions of this invention are peptides according to formula A and SEQ ID NO: 1 which have previously been described in patent application WO2018104561, which describes the compounds, their preparation and purification and biologic activity (Table 5, WO2018104561). Example 2 in WO2018104561 includes data on in vitro potency on the GLP-1 and GLP-2 receptor, Examples 3 and 4 concern the solubility and stability of the compound.

Synthesis of Dual Agonists

It is preferred to synthesise dual agonists of the invention by means of solid-phase or liquid-phase peptide synthesis methodology. In this context, reference may be made to WO 98/1 1 125 and, among many others, Fields, G.B. et aL., 2002, "Principles and practice of solid-phase peptide synthesis". In: Synthetic Peptides (2nd Edition), and the Examples herein. In accordance with the present invention, a dual agonist of the invention may be synthesised or produced in a number of ways, including for example, a method which comprises:

(a) synthesising the dual agonist by means of solid-phase or liquid-phase peptide synthesis methodology and recovering the synthesised dual agonist thus obtained; or (b) expressing a precursor peptide sequence from a nucleic acid construct that encodes the precursor peptide, recovering the expression product, and modifying the precursor peptide to yield a compound of the invention.

The precursor peptide may be modified by introduction of one or more non-proteinogenic amino acids, e.g. Aib, Orn, Dap, or Dab, introduction of an albumin binding moiety or introduction of the appropriate terminal groups —OH or —NH$_2$, etc.

Expression is typically performed from a nucleic acid encoding the precursor peptide, which may be performed in a cell or a cell-free expression system comprising such a nucleic acid.

Chemical Stability

The isotonic parenteral pharmaceutical compositions of this invention provide good or improved chemical stability.

The chemical stability at time point Y of GLP-1/GLP-2 dual agonist in any of the tested compositions disclosed herein can be expressed as the relative purity $X^Y$ of the GLP-1/GLP-2 dual agonist and is determined by measuring the absolute purity X' of the GLP-1/GLP-2 dual agonist and normalising it to the absolute purity $X^0$ of the GLP-1/GLP-2 dual agonist at day zero (day 0), wherein said absolute purities are determined by HPLC at a given time point Y by identifying the purity of peak corresponding to the GLP-1/GLP-2 dual agonist.

Thus, at day zero (day 0), the absolute purity X is the same as the absolute purity $X^0$ and thus chemical stability of a GLP-1/GLP-2 dual agonist in the tested composition, expressed as the relative purity $X^Y$=100%, wherein Y=day 0.

Relative purity can be calculated the following way:

$$X^Y=(X'/X^0)*100$$

wherein X is the relative purity at a given time point Y, $X^0$ is the absolute purity on day 0 and X is the absolute purity on the given time point Y, wherein the absolute purity $X^0$ or X' of the GLP-1/GLP-2 dual agonist in the tested composition are determined by HPLC, identifying the purity of peak corresponding to the GLP-1/GLP-2 dual agonist.

It was surprisingly found, that the chemical stability of said one or more GLP-1/GLP-2 dual agonists comprised in one or more parenteral pharmaceutical compositions of this invention, wherein said one or more tonicity agent is selected from salts and/or mannitol, have a stable and higher chemical stability compared to pharmaceutical compositions comprising other tonicity agents, such as sucrose, dextrose, glycerol, propylene glycol, and mannitol when in combination with the buffer L-histidine.

It was surprisingly found, that the chemical stability of said one or more GLP-1/GLP-2 dual agonists comprised in one or more parenteral pharmaceutical compositions of this invention, wherein mannitol, such as D-mannitol, is selected as tonicity agent, have a stable and higher chemical stability compared to pharmaceutical compositions comprising other tonicity agents, such as sucrose, dextrose, glycerol, propylene glycol, and mannitol when in combination with the buffer L-histidine. It was further surprisingly found, that the stability of said GLP-1/GLP-2 dual agonist in pharmaceutical compositions comprising mannitol, such as D-mannitol, is so much retained that the shelf-life of such compositions at 5° C. can be expected to be 1 year or more, for example up to 2 years, even without the composition comprising a preservative.

In some aspects, the pharmaceutical compositions of this invention have a shelf-life of at least about 1, 2, 3, 4, 5, 6, 7, 8, 9, 10, 11, 12,13,14, 15, 16, 17, 18, 19, 20, 21, 22, 23 or 24 months or more. Preferably the shelf-life is at least about 12 months or more. More preferably the shelf-life is at least about 24 months or more.

Preferably the shelf-life is at least about 24 months or more at a storage temperature of about 5° C.

It was surprisingly found, that the chemical stability of said one or more GLP-1/GLP-2 dual agonists comprised in one or more parenteral pharmaceutical compositions of this invention, comprising salt, such as NaCl as the tonicity agent, have a chemical stability which is at least as good as (i.e. comparable to) pharmaceutical compositions not comprising any tonicity agent(s) and a higher normalised stability than compositions comprising other tonicity agents, such as sucrose, dextrose and glycerol.

Stability

A peptide "retains its physical stability" or "has a good physical stability" in a pharmaceutical formulation if it shows no sign (or very little sign) of aggregation, precipitation and/or denaturation upon e.g. visual examination of colour and/or clarity, or as measured by UV light scattering, dynamic light scattering (DLS), circular dichroism, or by size exclusion chromatography (SEC) and is considered to still retain its biological activity. SEC measures soluble oligomer formations which may or may not be a precursor for visible aggregates.

Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example.

In the present invention, "stable" formulations include formulations in which at least 80%, more preferably at least 90%, more preferably at least 95%, more preferably at least 96%, more preferably at least 97%, more preferably at least 98%, and most preferably at least 99% of the GLP1-/GLP-2 dual agonist is active in the formulation after it has been stored at 2-8° C. for at least about 2 years.

In some aspects, pharmaceutical compositions of this invention are optimised to improve the GLP-1/GLP-2 dual agonist's chemical stability, expressed as relative purity of the GLP-1/GLP-2 dual agonist to maintain the biological effect of the peptide, even after day 0 over an extended period, such as about 2 weeks, about 3 weeks, about 4 weeks, about one month or more.

LIST OF ABBREVIATIONS

| Abbreviation | Explanation |
|---|---|
| AUC | Analytical ultra centrifugation |
| i.v. | Intravenous |
| s.c. | Subcutaneous |
| HPLC | High-performance liquid chromatography |
| ND | Not determined |
| N.P. | No particulates |
| part/cont | Particles per container |
| RP-HPLC | Reverse Phase High-performance liquid chromatography |
| CPD | Compound |
| SEQ ID NO | Sequence identification number |

Terms & Definitions

Compounds comprised in one or more isotonic pharmaceutical compositions disclosed herein are described either by general formulas, such as general formula A and/or general formula B or by their amino acid sequence, such as SEQ ID NO: 1. Specific forms, such as the —NH$_2$ or —OH form of the Compound (CPD), comprising the same amino acid sequence are herein denominated in the following way (Table 3), exemplified by compounds comprising or consisting of SEQ ID NO: 1.

TABLE 3

| SEQ ID | CPD | CPD form | Compound |
|---|---|---|---|
| 1 | 1 | 1OH | Hy-H[Aib]EGSFTSELATILD[K([17-carboxy-heptadecanoyl]-isoGlu)]QAARDFIAWLIQHKITD-OH |
| 1 | 1 | 1NH$_2$ | Hy-H[Aib]EGSFTSELATILD[K([17-carboxy-heptadecanoyl]-isoGlu)]QAARDFIAWLIQHKITD-NH$_2$ |

Thus, the abbreviation CPD1 refers to any form of the compound comprising or consisting of SEQ ID NO: 1, however CPD1OH refers to a compound comprising SEQ ID NO: 1, wherein said compound is in its—OH form.

The reference CPD1 as used herein and if not specified further refers to either CPD1 OH or CPDNH$_2$ and any pharmaceutically acceptable salt thereof. In some embodiments, this pharmaceutically acceptable salt may be a chloride salt, a salt of CPD1OH may also be described as e.g. Hy-H[Aib]EGSFTSELATILD[K([17-carboxy-heptadecanoyl]-isoGlu)]QAARDFIAWLIQHKITD-OH (SEQ ID NO: 1).[HCl].

When used herein the term "natural amino acid" is an amino acid (with the usual three letter codes and one letter codes in parenthesis) selected from the group consisting of: Glycine (Gly & G), proline (Pro & P), alanine (Ala & A), valine (Val & V), leucine (Leu & L), isoleucine (lie & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If anywhere in this invention reference is made to a GLP-½ GLP-1/GLP-2 dual agonist, agonist, analogue or GLP-1/GLP-2 dual agonists according to this invention comprising or not comprising G, P, A, V, L, I, M, C, F, Y,H, K, R, Q, N, E, D, S or T, without specifying further, amino acids are meant. If not otherwise indicated amino acids indicated with a single letter code in CAPITAL letters indicate the L-isoform, if however, the amino acid is indicated with a lower case letter, this amino acid is used/applied as it's D-form, e.g. K (i.e. L-lysine), k (i.e. D-lysine).

The abbreviation "Hy-" in connection with the compounds disclosed herein refers to hydrogen. The abbreviation in chosen to be indicated as "Hy" to avoid the hydrogen to be confused with the Histidine (H) in the beginning of the sequence.

Throughout the present description and claims, the generally accepted three-letter codes for other "α-amino acids" are used, such as sarcosine (Sar), norleucine (Nle), α-aminoisobutyric acid (Aib), 2,3-diaminopropanoic acid (Dap), 2,4-diaminobutanoic acid (Dab) and 2,5-diaminopentanoic acid (ornithine; Orn). Such other α-amino acids may be shown in square brackets "[ ]" (e.g. "[Aib]") when used in a general formula or sequence in the present specification, especially when the rest of the formula or sequence is shown using the single letter code.

Thus, the terms "dual GLP-½ agonist" or "dual GLP-½ peptide" or "GLP½ agonist" as used herein, refer to a peptide, which has activity on the GLP-1 receptor and the GLP-2 receptor and may be used interchangeably. A dual GLP-1/GLP-2 dual agonist comprising formula A or B may be a peptide of SEQ ID NO:1 or a peptide wherein one or more amino acids have been modified relative to SEQ ID NO: 1. Such agonists and/or peptides may further comprise one or more side chains, which have been covalently attached to the GLP-1/GLP-2 dual agonist. The term "side chain" may also be referred to as a "substituent". A GLP-1/GLP-2 dual agonist comprising such side chains may thus be "derivatised" GLP-1/GLP-2 dual agonist or "derivatised" GLP1/GLP-2 dual peptide or sometimes plainly a "GLP½ derivative". Thus, a GLP½ derivative can be a GLP-1/GLP-2 dual agonist.

In a particular aspect, the side chain is capable of forming non-covalent aggregates with albumin and may thus also be referred to as "albumin binding moiety", thereby promoting the circulation of the derivative with the blood stream, and also having the effect of protracting the time of action of the derivative, due to the fact that the aggregate of the dual GLP-1/GLP-2 dual agonist derivative and albumin is only slowly disintegrated to release the active pharmaceutical ingredient. Thus, the "substituent", or "side chain", is preferably referred to as an "albumin binding moiety".

The dual GLP-1/GLP-2 dual agonist or GLP-½ derivative of the present invention exhibit good physical stability. The term "physical stability" of a dual GLP-½ agonist according to the invention, or a formulation thereof refers to the tendency of the dual GLP-½ agonist to not form biologically inactive and/or insoluble aggregates as a result of exposure to thermo-mechanical stresses and/or interaction with interfaces and surfaces that are destabilising, such as hydrophobic surfaces and interfaces. Physical stability of the dual GLP-1/GLP-2 dual agonist formulations may be evaluated by means of visual inspection of particles and coloration changes of the pharmaceutical composition. Physical stability may also be assessed by evaluation of the content of sub-visual particles in the formulation.

The dual GLP-½ agonist of the present invention exhibits good chemical stability. The term "chemical stability" of a dual GLP-½ agonist according to the invention or of a formulation thereof refers to the low degree of chemical changes in the dual GLP-½ agonist structure hence avoiding the formation of chemical degradation products with potentially less potency and/or potentially increased immunogenic properties compared to the parent (native) dual GLP-½ agonist structure. Various chemical degradation products can be formed depending on the type and nature of the parent dual GLP-½ agonist and the environment to which the dual GLP-½ agonist is exposed. Chemical degradation cannot be completely avoided and increasing amounts of chemical degradation products are often seen during storage and use of peptide formulations as well-known by the person skilled in the art. Most peptides are prone to deamidation, a process in which the side chain amide group in glutaminyl or asparaginyl residues is hydrolysed to form a free carboxylic acid. Other degradation pathways involve the formation of high molecular weight transformation products where two or more peptide molecules are covalently bound to each other through transamidation and/or disulfide interactions leading to formation of covalently bound dimer, oligomer and polymer degradation products (Stability of Protein Pharmaceuticals, Ahern. T.J. & Manning M.C., Plenum Press, New 25 York 1992). Oxidation (of for instance methionine residues) can be mentioned as another variant of chemical degradation. The chemical stability of the GLP1/GLP-2 dual agonist formulation can be evaluated by measuring the relative purity of the peptide at various time-points and thus the peptide's chemical degradation after exposure to different environmental conditions, such as time and temperature (the formation of degradation products can often be accelerated by for instance increasing the temperature from room temperature to 40° C. or by applying physical stressors, such as shaking). The level of purity of the peptide at each individual time point is determined by separation of the peptide peak and degradation products depending on molecule size and/or charge using various chromatography techniques (e.g. SEC-HPLC and/or RP-HPLC). The absolute amount of peptide in the main peak (the peptide peak) at time zero will be set to a relative purity of 100% and the following individual measurements at later time points will be normalised to this absolute amount and expressed as a percentage thereof.

The chemical stability at time point Y of GLP-1/GLP-2 dual agonist in any of the tested compositions disclosed herein can be expressed as the relative purity $X^Y$ of the GLP-1/GLP-2 dual agonist and is determined by measuring the absolute purity X' of the GLP-1/GLP-2 dual agonist and normalising it to the absolute purity $X^0$ of the GLP-1/GLP-2 dual agonist at day zero (day 0), wherein said absolute purities are determined by HPLC at a given time point Y by identifying the purity of peak corresponding to the GLP-1/GLP-2 dual agonist.

Thus, at day zero (day 0), the absolute purity X is the same as the absolute purity $X^0$ and thus chemical stability of a GLP-1/GLP-2 dual agonist in the tested composition, expressed as the relative purity $X^Y$=100%, wherein Y=day 0.

Relative purity can be calculated the following way:

$$X^Y=(X'/X^0)*100$$

wherein X is the relative purity at a given time point Y, $X^0$ is the absolute purity on day 0 and X is the absolute purity on the given time point Y, wherein the absolute purity $X^0$ or X' of the GLP-1/GLP-2 dual agonist in the tested composition are determined by HPLC, identifying the purity of peak corresponding to the GLP-1/GLP-2 dual agonist.

When using terms such as "about" and "approximately" in relation to numerical values, the skilled person should immediately recognise that any effect or result, which may be associated with the given values can be obtained within a certain tolerance from the particular values. The term "about" as used herein thus means in reasonable vicinity of the stated numerical value, such as plus or minus 10%.

When the term "about" is used about the chemical stability in this patent application, the reasonable vicinity will be below 2%, such as 0.5% or 0.75%, 1% or 1.5%.

The term "predominantly" as used herein in connection with the physical properties and/or form of a GLP-1/GLP-2 dual agonist means, that at least about 94% of the GLP-1/GLP-2 dual agonist is present in the formulation is in a particular form as described and no more than about 6% of the GLP-1/GLP-2 dual agonist is of another form.

The term "isotonic" as used herein, refers to the tonicity relative to body fluids at the site of injection, i.e. i.v. or s.c. Thus, the term "isotonic" is used to describe that the one or more pharmaceutical composition described herein has the same tonicity as body fluids, such as red blood cells and/or blood plasma. Compositions with an osmolality of about 300 mOsmol/kg, such as about 280-320 mOsmol/kg or about 290-320 mOsmol/kg are considered as isotonic.

Tonicity is the "effective osmolality" and is equal to the sum of the concentrations of the solutes, which have the capacity to exert an osmotic force across the membrane. Biologic systems are compatible with solutions having similar osmotic pressures, i.e., an equivalent number of dissolved species, and this is thus desired for medicinal products, which are administered parenterally.

Isotonicity is important for parenteral pharmaceutical compositions, because a "hypotonic" solution causes a cell to swell, whereas a "hypertonic" solution causes a cell to shrink. Although it is related to osmolality, tonicity also takes into consideration the ability of the solute to cross the cell membrane.

The term "tonicity agent", "isotonicity giver" or "isotonic agents" as disclosed herein refers to agents added to one or more pharmaceutical compositions disclosed herein, to achieve isotonicity relative to bodily fluids. A range of ionic and non-ionic tonicity agents are used in pharmaceutical compositions. The non-ionic tonicity agents may be selected from dextrose, propylene glycol, glyceryl, mannitol, such as D-mannitol and sorbitol. The ionic tonicity agents may include, alkali metals or earth metal halides, such as $CaCl_2$, KBr, KCl, LiCl, NaI, NaBr, NaCl, $Na_2SO_4$.

"Ionic compounds" are two or more ions held together by attraction. An example of an ionic compound is table salt. It consists of positive sodium ions and negative chloride ions. They have high melting and boiling points and are hard or brittle. They can also be dissolved in water. The definition for a "non-ionic compound" is that the chemical bonds in this compound are non-ionic. They usually have chemical bonds that share electron density.

The term "solvent" as used herein is meant to be a substance that dissolves a solute (a chemically distinct liquid, solid or gas), resulting in a solution. A solvent is usually a liquid but can also be a solid, a gas, or a supercritical fluid. Solvents are generally classified by the polarity, and considered either polar or non-polar, as indicated by the dielectric constant. Generally, solvents with dielectric constants greater than about 5 are considered "polar" and those with dielectric constants less than 5 are considered "non-polar".

A "protic solvent" is herein considered a solvent that has a hydrogen atom bound to an oxygen (as in a hydroxyl group), a nitrogen (as in an amine group) or a fluorine (as in hydrogen fluoride). In general terms, any solvent that contains a labile $H^+$ is called a protic solvent. The molecules of such solvents readily donate protons ($H^+$) to reagents. Conversely, "aprotic solvents" cannot donate hydrogen. Water, such as milliQ water is thus herein considered a polar protic solvent.

The term "salts" as used herein refers to an ionic compound that can be formed by the neutralisation reaction of an acid and a base. Salts are composed of related numbers of cations (positively charged ions) and anions (negative ions) so that the product is electrically neutral (without a net charge). These component ions can be inorganic, such as chloride ($Cl^-$), or organic, such as acetate ($CH_3CO^{2-}$); and can be monatomic, such as fluoride ($F^-$), or polyatomic, such as sulfate ($SO_4^{2-}$). The terms "pharmaceutically acceptable salt of CPD1" or "salt of CPD1" as used herein describe salts of the compound comprising SEQ ID NO: 1. "Hy-H[Aib] EGSFTSELATILD[K([17-carboxy-heptadecanoyl]-iso-Glu)]QAARDFIAWLIQHKITD-OH. [acid]" as used herein identifies a salt of Hy-H[Aib]EGSFTSELATILD[K([17-carboxy-heptadecanoyl]-isoGlu)]QAARDFIAWLIQHKITD-OH (SEQ ID NO: 1), wherein [acid]refers to the acid, which in a neutralisation reaction forms the salt of said compound, e.g. Hy-H[Aib]EGSFTSELATILD[K([17-carboxy-heptadecanoyl]-isoGlu)]QAARDFIAWLIQHKITD-OH (SEQ ID NO: 1).[HCl]will thus refer to a chloride salt. "Pharmaceutically acceptable salt" as used herein refers to salts that are safe and effective for use in mammals and that possess the desired biological activity. Pharmaceutically acceptable salts include salts of acidic or basic groups present in CPD1. For a review on pharmaceutically acceptable salts, see Berge et aL., 66 J. Pharm. Sci. 1-19 (1977), incorporated herein by reference.

General Methods Used

Methods for Preparation of GLP-1/GLP-2 Dual Agonists— Laboratory Scale & Upscaled Batches (ASSAY 1) The GLP-1/GLP-2 dual agonists were prepared according to the guidance in patent application WO2018104561, which describes the compounds, their preparation and purification as well as analysis in detail in for example Examples 1 to 4.

CPD1 was synthesised using a Solid Phase Peptide Synthesis (SPPS) approach and standard Fmoc coupling methodologies. After completed synthesis, the peptide sequence was deprotected and cleaved from the solid support, and the crude peptide was purified using preparative reverse phase HPLC. The peptide was converted to an acceptable salt form and lyophilised to provide the final CPD1 drug substance.

Method for Preparation & Analysis of Pharmaceutical Compositions (ASSAY 11)

Sample Solutions for Laboratory Scale and Upscaled Batch Compositions

The GLP-1/GLP-2 dual agonist drug substance was prepared according to ASSAY I and dissolved in MQW. pH was measured. This was followed by addition and mixing of the ingredients as illustrated in Table 10. The final concentrations were 0.2 mg/mL, 2 mg/mL or 10 mg/mL of the GLP-1/GLP-2 dual agonists as indicated in the tables and examples in this application. pH was then adjusted using 1 M NaOH/HCl as needed to reach the appropriate pH.

For a formulation of 2 mg/mL CPD1, mannitol (41.9 g), $NaH_2PO_4$ (0.16 g) and $Na_2HPO_4$ (2.65 g) were dissolved in approx. 0.7 L water for injections (WFI). A suitable amount of sodium hydroxide (1 N aqueous solution) was added to pre-adjust the pH. CPD1 peptide (2.0 g, adjusted for purity) was dissolved in approx. 0.20 L WFI. The solution of CPD1 peptide was added to the excipient solution. The solution was mixed thoroughly, pH was measured and, if necessary, pH was adjusted with 1 N NaOH and/or 1 N HCl to reach the desired pH. Water was added up to 1.0 L, the formulation was sterile filtered through a 0.22 μm filter and filled in suitable containers.

The laboratory scale compositions were prepared in volumes below and up to 0.5 mL to about 2 mL, whereas the upscaled batches were prepared in volumes of between 2 L to about 5.5 L, samples of said upscaled batches evaluated by any one of the following Assays were usually about 1.2 mL.

For stability testing, the compositions were stored as samples of the batches at the indicated temperatures (see examples) in a dark room (i.e. lights switched off).

The formulations were stored under these conditions for the duration shown in the tables (e.g. D0=day 0, D3=day 3, D7=day 7, D14=day 14, D24=day 24, 0M=0 months=day zero (D0), 1 M=1 month, 2M=2 months, 3M=3 months, 6M=6 months, 9M=9 months or 12M=12 months), and analysed by RP-HPLC according to ASSAY Ill at relevant time-points and diluted in Eluent A to a concentration of 0.5 mg/mL (addition of 750 μL) prior to analyses by RP-HPLC.

Method for Measuring GLP-1/GLP-2 Dual Agonists Purity & Determining the Normalised GLP-1/GLP-2 Dual Agonists Purity in % (ASSAY III)

The chemical stability of a GLP-1/GLP-2 dual agonist (peptide) is herein expressed as the relative purity of the peptide peak (i.e. the main peptide peak) determined by HPLC at a given time point, and normalised to the absolute purity of the peptide peak (i.e. main peptide peak) at day zero (day 0 (DO)), which is set to 100% purity and thus chemical stability in % of said dual agonist.

The chemical stability of a GLP-1/GLP-2 dual agonist (peptide) prepared according to ASSAY I comprised in a parenteral pharmaceutical composition as prepared according to ASSAY II are analysed according to the following method:

RP-HPLC General Method (ASSAY IIIa)

A Dionex Ultimate 3000 HPLC system, giving a linear gradient, at a flow rate of 0.5 mL/min was used for the analysis. The mobile phase components consisted of 0.3% TFA in 90% acetonitrile/10% MQW and 0.3% TFA in MQW. A wavelength of 215 nm was used for detection. Injection amount was 2 μg of peptide. The column used for HPLC analysis was a Phenomenex Kinetex C18, 150 by 3.0 mm, 2.6 μm particle size. Runtime was 25 minutes.

TABLE 4

| The RP-HPLC method details | |
| --- | --- |
| Method file name | LP401.073.02 |
| Column | Phenomenex Kinetex C18, 150 by 3.0 mm, 2.6 μm |
| Gradient (time; % B) | 0; 40, 20; 70, 20.01; 95, 22; 95, 22.01; 40, 25; 40 |
| Eluent A | 0.3% TFA in MQW |
| Eluent B | 0.3% TFA in MeCN |
| Flow Rate | 0.500 mL/min |
| Injection Amount | 2 μg |
| Column Temperature | 25° C. |
| Auto Sampler Temp. | 4° C. |
| UV detection | 215 nm |

The results are shown in Table 10 as the measured by RP-HPLC after incubation under stress conditions (e.g. 40° C. for 0, 3, 7, 14 or 24 days). This purity is a measure for the remaining intact compound after incubation in stress solutions, relative to the purity measured on day 0 (DO, day zero) and expressed as the normalised CPD 1 agonists purity in %.

These results do not take into account possible hidden degradation products not observed by this analytical RP-HPLC method.

Methods for Determining Physical Stability (ASSAY IV)

Physical stability was determined by visual inspection (ASSAY IVa) and detection of sub visual particles (ASSAY IVb) or by measuring aggregation tendency by ThT (ASSAY IVc).

Visual Inspection of the Solution (ASSAY IVa)

Visual inspection was performed following the standards of the USP>790<official as of 1-May-2016.

Detection of Sub Visible Particles (ASSAY IVb)

Detection of sub visual particles was performed by following the standards of: USP>788<official as of 1 May 2013.

Physical Stability Evaluation of pH Via ThT (ASSAY IVc)

Aggregation in the form of fibril formation was detected using the amyloid-specific dye Thioflavin T (ThT), which is frequently employed to demonstrate the presence of fibrils in solution (see, e.g., Groenning, M., J. Chem. Biol. 3(1) (2010), pp. 1-18; Groenning etaL. J Struct. Biol. 158 (2007) pp. 358-369; and Levine, H., Ill, Protein Sci. 2 (1993) pp. 404-410).

Samples were prepared in a total volume of 0.5 mL API (herein e.g. CPD1) stock solutions were prepared by dissolving API in demineralised water at ambient temperature (typically 25° C.) to achieve 5 and 25 mg/mL API, respectively. 8 working solutions were prepared: 1) 40 mM phosphate pH 6 and 80 µM ThT; 2) 40 mM phosphate pH 6.5 and 80 µM ThT; 3) 40 mM phosphate pH 7 and 80 µM ThT; 4) 40 mM phosphate pH 8 and 80 µM ThT; 5) 40 mM phosphate pH 6, 540 mM mannitol and 80 µM ThT; 6) 40 mM phosphate pH 6.5, 540 mM mannitol and 80 µM ThT; 7) 40 mM phosphate pH 7, 540 mM mannitol and 80 µM ThT; and 8) 40 mM phosphate pH 8, 540 mM mannitol and 80 µM ThT.

200 µL of API stock was mixed with 250 µL working solution, pH was measured and adjusted to target, followed by adding demineralised water to a final volume of 500 µL. Samples were loaded in a 96-well black fluorescence plate (clear bottom) in triplicate 3×150 µL. Data were collected at fixed intervals of 10 min, each preceded by 300 s of automixing (agitation), over a period of 96 hours at 40° C. Physical stability, expressed as lag-time of fibril formation (in hours), was defined as the intersection between two linear regressions representing the initial stable phase and the growth phase.

Method for Evaluatinq Content of Multimers Via Analytical Ultra Centrifuqation (AUC) (Assay V)

Sedimentation velocity experiments were carried out on a BeckmanCoulter Optima XL-I Analytical Ultracentrifuge using both interference and absorbance detection. Samples were filled in titanium cuvettes with optical pathlengths of 12 mm. The experiments were performed at 20° C. An angular velocity of 50 krpm was applied. Solvent density and viscosity were incrementally calculated according to the buffer composition, as given on the result plots. The solutes' partial specific volume was incrementally calculated from the amino acid/lipid composition (approximately 0.748 mL/g). Evaluation was carried out as global fitting to approximate solutions of the Lamm equation with Sedfit v. 15.01b. The frictional properties of the molecules in terms of the frictional ratio $f=f_0$ were treated as floating parameters.

Samples analysed using AUC were prepared according to ASSAY II.

Non-Limiting Aspects of the Invention

The following part of the description comprises particular, non-limiting aspects of the invention. The aspects described below may be combined with any of the aspects of the invention described above and below and herein 1. An isotonic parenteral pharmaceutical composition, comprising:
   a. at least about 1 mg/mL of one or more GLP-1/GLP-2 dual agonist comprising general formula A:

H[Aib]EG-X5-F-X7-SELATILD-[ψ]-QAARDFI-
   AWLI-X28-X29-KITD      (A) (SEQ ID NO: 2), wherein X5 is T or S; X7 is T or S; X28 is Q, E, A, H, Y, L, K, R or S; X29 is H and at least one of X5 and X7 is T, and wherein [ψ]indicates an L or D lysine residue in which an albumin binding moiety is conjugated to the GLP-1/GLP-2 dual agonist, and
   wherein said albumin binding moiety is [K([17-carboxy-heptadecanoyl]-isoGlu)]; and
   b. about 1 mM to about 200 mM, such as about 20 mM to about 200 mM, of buffer component; and
   c. about 1 mM to about 360 mM of one or more tonicity agent, preferably about 150 mM to about 250 mM of one or more tonicity agent,
   wherein said one or more tonicity agent is an ionic or a non-ionic tonicity agent,
   wherein the ionic tonicity agent is selected from the group consisting of salts, alkali metals or earth metal halides, and the non-ionic tonicity agent is mannitol, such as D-mannitol,
   wherein said composition further comprises a solvent, and
   wherein said composition has a pH of about pH 6.0 to about pH 8.2, preferably a pH of about pH 7.0 to about pH 8.0.

2. The isotonic parenteral pharmaceutical composition of aspect 1, comprising about 150 mM to about 250 mM of one or more tonicity agent, wherein said one or more tonicity agent is an ionic tonicity agent selected from the group consisting of $CaCl_2$, KBr, KCl, LiCl, NaI, NaBr, NaCl or $Na_2SO_4$, preferably wherein the ionic tonicity agent is NaCl or KCl.

3. The parenteral pharmaceutical composition of any one of the preceding aspects, wherein said one or more GLP-1/GLP-2 dual agonist comprising general formula A is of the general formula B:

H[Aib]EG-X5-FT-SELATILD-[ψ]-QAARDFIAWLI-
   X28-HKITD      (B) (SEQ ID NO: 3), wherein X5 is T or S; X28 is Q, E, A, H, Y, L, K, R or S and
   wherein [4)]indicates an L or D lysine residue in which the albumin binding moiety is conjugated to the GLP-1/GLP-2 dual agonist and
   wherein said albumin binding moiety is [K([17-carboxy-heptadecanoyl]-isoGlu)].

4. The parenteral pharmaceutical composition of any one of the preceding aspects, wherein said composition is isotonic.

5. The parenteral pharmaceutical composition of any one of the preceding aspects, wherein said one or more GLP-1/GLP-2 dual agonist comprising general formula A or B comprises the sequence:
   H[Aib]EGSFTSELATILD[ψ]QAARDFIAWLIQH-
   KITD (SEQ ID NO: 1).

6. The parenteral pharmaceutical composition of any one of the preceding aspects, wherein said one or more GLP-1/GLP-2 dual agonist comprising general formula A or B is:
   a. Hy-H[Aib]EGSFTSELATILD[K([17-carboxy-hep-
   tadecanoyl]-isoGlu)]QAARDFIAWLIQHKITD-OH
   (CPD10H) (SEQ ID NO: 1) or b. Hy-H[Aib]EGSFTSELATILD[K([17-carboxy-hep-tadecanoyl]-isoGlu)]QAARDFIAWLIQHKITD-NH$_2$ (CPD1 NH$_2$) (SEQ ID NO: 1).

7. The isotonic parenteral pharmaceutical composition according to aspect 6, wherein said one or more GLP-1/GLP-2 dual agonist comprising general formula A or B is CPD1 OH or any pharmaceutically acceptable salt thereof.

8. The isotonic parenteral pharmaceutical composition according to aspect 7, wherein said one or more GLP-1/GLP-2 dual agonist comprising general formula A or B is a pharmaceutically acceptable salt of CPD1OH, preferably a chloride salt.

9. The isotonic parenteral pharmaceutical composition according to aspect 6, wherein said one or more GLP-1/GLP-2 dual agonist comprising general formula A or B is CPD1 NH$_2$.

10. The isotonic parenteral pharmaceutical composition according to aspect 9, wherein said one or more GLP-1/GLP-2 dual agonist comprising general formula A or B is a pharmaceutically acceptable salt of CPD1 NH$_2$, preferably a chloride salt.

11. The isotonic parenteral pharmaceutical composition of any one of the preceding aspects, wherein said solvent is a polar aprotic, polar protic or nonpolar solvent.

12. The isotonic parenteral pharmaceutical composition of any one of the preceding aspects, wherein said one or more tonicity agent is a non-ionic tonicity agent and is mannitol, such as D-mannitol, or wherein said one or more tonicity agent is an ionic tonicity agent selected from NaCl or KCl.

13. The isotonic parenteral pharmaceutical composition of any one of the preceding aspects, wherein said one or more tonicity agent is a non-ionic tonicity agent and is mannitol, such as D-mannitol.

14. The isotonic parenteral pharmaceutical composition of any one of the preceding aspects, wherein said pH is adjusted with either NaOH or HCl as needed.

15. The isotonic parenteral pharmaceutical composition of any one of the preceding aspects, not comprising histidine.

16. The isotonic parenteral pharmaceutical composition of any one of the preceding aspects, not comprising L-histidine.

17. The isotonic parenteral pharmaceutical composition of any one of the preceding aspects, not comprising any of the tonicity agents selected from the group consisting of dextrose, sucrose, propylene glycol or glycerol.

18. The isotonic parenteral pharmaceutical composition of any one of the preceding aspects, not comprising any of the excipients selected from the group consisting of dextrose, sucrose, propylene glycol or glycerol.

19. The isotonic parenteral pharmaceutical composition of any one of the preceding aspects, not comprising propylene glycol.

20. The isotonic parenteral pharmaceutical composition of any one of the preceding aspects, not comprising dextrose.

21. The isotonic parenteral pharmaceutical composition of any one of the preceding aspects, not comprising sucrose.

22. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 150 mM to about 360 mM.

23. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 150 mM to about 300 mM.

24. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 150 mM to about 250 mM.

25. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 210 mM to about 240 mM.

26. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 210 mM to about 230 mM.

27. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 360 mM.

28. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 300 mM.

29. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 250 mM.

30. The isotonic parenteral pharmaceutical composition of any one of the preceding aspects, wherein said one or more tonicity agent is mannitol, such as D-mannitol, and is present in the isotonic parenteral pharmaceutical composition at a final concentration of about 230 mM.

31. The isotonic parenteral pharmaceutical composition of any one of the preceding aspects, wherein said one or more tonicity agent is a salt and is present in the isotonic parenteral pharmaceutical composition at a final concentration of about 1 mM to about 360 mM.

32. The isotonic parenteral pharmaceutical composition of any one of the preceding aspects, wherein said one or more tonicity agent is a salt and is present in the isotonic parenteral pharmaceutical composition at a final concentration of about 50 mM to about 250 mM.

33. The isotonic parenteral pharmaceutical composition of any one of the preceding aspects, wherein said one or more tonicity agent is a salt and is present in the isotonic parenteral pharmaceutical composition at a final concentration of about 150 mM to about 200 mM.

34. The isotonic parenteral pharmaceutical composition of any one of the preceding aspects, wherein said one or more tonicity agent is a salt and is present in the isotonic parenteral pharmaceutical composition at a final concentration of about 200 mM to about 230 mM.

35. The isotonic parenteral pharmaceutical composition of any one of the preceding aspects, wherein said one or more tonicity agent is NaCl or KCl and is present in the isotonic parenteral pharmaceutical composition at a final concentration of about 50 mM to about 230 mM.

36. The isotonic parenteral pharmaceutical composition of any one of the preceding aspects, wherein said one or more tonicity agent is NaCl or KCl and is present in the isotonic parenteral pharmaceutical composition at a final concentration of about 150 mM to about 200 mM.

37. The isotonic parenteral pharmaceutical composition of any one of the preceding aspects, wherein said one or more tonicity agent is NaCl or KCl and is present in the isotonic parenteral pharmaceutical composition at a final concentration of about 200 mM to about 250 mM.

38. The isotonic parenteral pharmaceutical composition of any one of the preceding aspects, wherein said buffer component is selected from the group consisting of phosphate buffer, citrate buffer, histidine buffer or tris buffer, bis tris, or a combination thereof.

39. The isotonic parenteral pharmaceutical composition of any one of the preceding aspects, wherein said buffer component is selected from the group consisting of phosphate buffer, tris buffer or a combination thereof.

40. The isotonic parenteral pharmaceutical composition of any one of the preceding aspects, wherein said buffer component is a phosphate buffer.

41. The isotonic parenteral pharmaceutical composition of any one of the preceding aspects, wherein said buffer component is a sodium phosphate buffer.

42. The isotonic parenteral pharmaceutical composition of any one of the preceding aspects, wherein said buffer component is a sodium phosphate buffer, such as $Na_2HPO_4$.

43. The isotonic parenteral pharmaceutical composition of any one of the preceding aspects, wherein said buffer component is not a tris buffer.

44. The isotonic parenteral pharmaceutical composition of any one of the preceding aspects, wherein said buffer component is not a citrate buffer.

45. The isotonic parenteral pharmaceutical composition of any one of the preceding aspects, comprising less than about 6% L-histidine.

46. The isotonic parenteral pharmaceutical composition of any one of the preceding aspects, comprising less than about 5% L-histidine, preferably less than about 3% L-histidine.

47. The isotonic parenteral pharmaceutical composition of any one of the preceding aspects, comprising less than about 1% L-histidine.

48. The isotonic parenteral pharmaceutical composition of any one of the preceding aspects, wherein said buffer component is not a histidine buffer or a buffer comprising histidine, such as L-histidine.

49. The isotonic parenteral pharmaceutical composition of any one of the preceding aspects, wherein said buffer component is not a buffer comprising histidine or L-histidine.

50. The isotonic parenteral pharmaceutical composition of any one of the preceding aspects, wherein said buffer component is a phosphate buffer, said one or more tonicity agent is mannitol, such as D-mannitol, and said one or more GLP1/GLP-2 dual agonist comprises a sequence of formula A.

51. The isotonic parenteral pharmaceutical composition of any one of the preceding aspects, wherein said buffer component is a phosphate buffer, said one or more tonicity agent is mannitol, such as D-mannitol, and said one or more GLP1/GLP-2 dual agonist comprises a sequence of formula B.

52. The isotonic parenteral pharmaceutical composition of any one of the aspects 50-51, wherein said one or more GLP1/GLP-2 dual agonist comprises a sequence of SEQ ID NO: 1.

53. The isotonic parenteral pharmaceutical composition of any one of the preceding aspects, wherein said one or more GLP1/GLP-2 dual agonist is CPD1.

54. The isotonic parenteral pharmaceutical composition of any one of the preceding aspects, wherein said one or more GLP1/GLP-2 dual agonist is pharmaceutically acceptable salt of CPD1.

55. The isotonic parenteral pharmaceutical composition of any one of the preceding aspects, wherein said one or more GLP1/GLP-2 dual agonist is CPD1OH.

56. The isotonic parenteral pharmaceutical composition of aspect 55, wherein said one or more GLP1/GLP-2 dual agonist is a pharmaceutically acceptable salt of CPD1OH.

57. The isotonic parenteral pharmaceutical composition of any one of the aspects 50 to 51, wherein said one or more GLP1/GLP-2 dual agonist is CPD1 $NH_2$.

58. The isotonic parenteral pharmaceutical composition of aspect 57, wherein said one or more GLP1/GLP-2 dual agonist is pharmaceutically acceptable salt of CPD1 $NH_2$.

59. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 1 mM to about 200 mM.

60. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 1 mM to about 100 mM.

61. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 100 mM.

62. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 1 mM to about 50 mM.

63. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 1 mM to about 20 mM.

64. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 15 mM to about 50 mM.

65. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 15 mM to about 25 mM.

66. The isotonic parenteral pharmaceutical composition of any one of the preceding aspects, wherein said buffer component is a phosphate buffer and wherein said phosphate buffer is present in the isotonic parenteral pharmaceutical composition at a final concentration of about 20 mM.

67. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of formula A, wherein the pH is between about pH 7.0 and about pH 8.0, most preferably about pH 8.0.

68. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of formula B, wherein the pH is between about pH 7.0 and about pH 8.0, most preferably about pH 8.0.

69. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of SEQ ID NO: 1, wherein the pH is between about pH 6.0 and about pH 8.0, preferably between about pH 7.0 and about pH 8.0, most preferably about pH 8.0.

70. The isotonic parenteral pharmaceutical composition of any one of the preceding aspects, wherein said buffer component is a phosphate buffer in a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of Formula A, wherein the pH is between about pH 6.0 and about pH 8.0, preferably between about pH 7.0 and about pH 8.0, most preferably about pH 8.0.

71. The isotonic parenteral pharmaceutical composition of any one of the preceding aspects, wherein said buffer component is a phosphate buffer in a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of Formula B wherein the pH is between about pH 6.0 and about pH 8.0, preferably between about pH 7.0 and about pH 8.0, most preferably about pH 8.0.

72. The isotonic parenteral pharmaceutical composition of any one of the preceding aspects, wherein said buffer component is a phosphate buffer in a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist is CPD1 OH, wherein the pH is between about pH 7.0 and about pH 8.0, most preferably about pH 8.0

73. The isotonic parenteral pharmaceutical composition of any one of the preceding aspects, wherein said buffer component is a phosphate buffer in a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist is CPD1 $NH_2$, wherein the pH is between about pH 7.0 and about pH 8.0, most preferably about pH 8.0.

74. The isotonic parenteral pharmaceutical composition of any one of the preceding aspects, wherein said pH is between about pH 7.0 and about pH 8.2, most preferably about pH 8.0.

75. The isotonic parenteral pharmaceutical composition of any one of the preceding aspects, wherein said pH is between about pH 7.0 and about pH 8.2, preferably about pH 7.5 or about pH 8.0.

76. The isotonic parenteral pharmaceutical composition of any one of the preceding aspects, wherein said pH is between about pH 7.0 and about pH 8.2, preferably about pH 7.6 or about pH 8.0.

77. The isotonic parenteral pharmaceutical composition of any one of the preceding aspects, wherein said pH is between about pH 7.0 and about pH 8.2, preferably about pH 7.6 or about pH 7.7.

78. The isotonic parenteral pharmaceutical composition of any one of the preceding aspects, wherein said pH is between about pH 7.0 and about pH 8.2, preferably about 7.6.

79. The isotonic parenteral pharmaceutical composition of any one of the preceding aspects, wherein said pH is between about pH 7.0 and about pH 8.2, preferably about pH 8.0.

80. The isotonic parenteral pharmaceutical composition of any one of the preceding aspects, wherein said pH is between about pH 7.0 and about pH 8.2, preferably about pH 7.0.

81. The isotonic parenteral pharmaceutical composition of any one of the preceding aspects, wherein said pH is about pH 8.0.

82. The isotonic parenteral pharmaceutical composition of any one of the preceding aspects, wherein said pH is about pH 7.0.

83. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 210 mM to about 240 mM, preferably about 230 mM.

84. The isotonic parenteral pharmaceutical composition of any one of the preceding aspects, wherein said buffer component is a phosphate buffer in a final concentration of about 15 mM to about 25 mM, preferably about 20 mM, said one or more tonicity agent is mannitol, such as D-mannitol in a final concentration of about 210 mM to about 240 mM.

85. The isotonic parenteral pharmaceutical composition of any one of the preceding aspects, wherein said buffer component is a phosphate buffer in a final concentration of about 15 mM to about 25 mM, preferably about 20 mM, said one or more tonicity agent is mannitol, such as D-mannitol in a final concentration of about 230 mM.

86. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol at a final concentration of about 190 mM to about 240 mM, preferably about 230 mM and said one or more GLP-1/GLP-2 dual agonist is CPD1 OH or CPD1 $NH_2$ or any pharmaceutically acceptable salt thereof.

87. The isotonic parenteral pharmaceutical composition of any one of the aspects 83-86, wherein said one or more GLP-1/GLP-2 dual agonist is CPD1OH or any pharmaceutically acceptable salt thereof.

88. The isotonic parenteral pharmaceutical composition of any one of the aspects 83-86, wherein said one or more GLP-1/GLP-2 dual agonist is CPD1 $NH_2$ or any pharmaceutically acceptable salt thereof.

89. The isotonic parenteral pharmaceutical composition of any one of the preceding aspects comprising between about 1 mg/mL to about 15 mg/mL GLP-1/GLP-2 dual agonist or any pharmaceutically acceptable salt thereof.

90. The isotonic parenteral pharmaceutical composition of any one of the preceding aspects comprising at least about 2 mg/mL GLP-1/GLP-2 dual agonist or any pharmaceutically acceptable salt thereof.

91. The isotonic parenteral pharmaceutical composition of any one of the preceding aspects comprising between about 2 mg/mL to about 10 mg/mL GLP-1/GLP-2 dual agonist or any pharmaceutically acceptable salt thereof.

92. The isotonic parenteral pharmaceutical composition of any one of the preceding aspects comprising about 2 mg/mL GLP-1/GLP-2 dual agonist or any pharmaceutically acceptable salt thereof.

93. The isotonic parenteral pharmaceutical composition of any one of the preceding aspects comprising about 10 mg/mL GLP-1/GLP-2 dual agonist or any pharmaceutically acceptable salt thereof.

94. The isotonic parenteral pharmaceutical composition of any one of the preceding aspects, wherein said pharmaceutical composition is an aqueous composition.

95. The isotonic parenteral pharmaceutical composition of any one of the preceding aspects, wherein the osmolality of the compositions as described herein is about 230 mOsmol/kg to about 370 mOsmol/kg.

96. The isotonic parenteral pharmaceutical composition of any one of the preceding aspects, wherein the osmolality of the compositions as described herein is about 280 mOsmol/kg to about 320 mOsmol/kg.

97. The isotonic parenteral pharmaceutical composition of any one of the preceding aspects, wherein the osmolality of the compositions as described herein is about 290 mOsmol/kg to about 320 mOsmol/kg.

98. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 210 mM to about 240 mM, preferably about 230 mM, comprising about 10 mg/mL of CPD1OH or any pharmaceutically acceptable salt thereof, and the pH is between about pH 7.0 to about pH 8.2, preferably about pH 8.0.

99. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 210 mM to about 240 mM, preferably about 230 mM, comprising about 10 mg/mL of CPD1 $NH_2$ or any pharmaceutically acceptable salt thereof, and the pH is between about pH 7.0 to about pH 8.2, preferably about pH 8.0.

100. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of 210 mM to about 240 mM, preferably about 230 mM, comprising about 2 mg/mL of CPD1OH or any pharmaceutically acceptable salt thereof, and the pH is between about pH 7.0 to about pH 8.2, preferably about pH 8.0.

101. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 210 mM to about 240 mM, comprising about 2 mg/mL of CPD1 $NH_2$ or any pharmaceutically acceptable salt thereof, preferably about 230 mM and the pH is between about pH 7.0 to about pH 8.2, preferably about pH 8.0.

102. The isotonic parenteral pharmaceutical composition of any one of the preceding aspects, wherein said buffer component is a phosphate buffer in a final concentration of about 15 mM to about 25 mM, preferably about 20 mM, said one or more tonicity agent is mannitol, such as D-mannitol, at a final concentration of about 210 mM to about 240 mM, preferably about 230 mM, comprising about 10 mg/mL of CPD1OH or any pharmaceutically acceptable salt thereof, and the pH is between about pH 7.0 to about pH 8.2, preferably about pH 7.0.

103. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 210 mM to about 240 mM, preferably about 230 mM, comprising about 10 mg/mL of CPD1 $NH_2$ or any pharmaceutically acceptable salt thereof, and the pH is between about pH 7.0 to about pH 8.2, preferably about pH 7.0.

104. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 210 mM to about 240 mM, preferably about 230 mM, comprising about 2 mg/mL of CPD1OH or any pharmaceutically acceptable salt thereof, and the pH is between about pH 7.0 to about pH 8.2, preferably about pH 7.0.

105. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 210 mM to about 240 mM, preferably about 230 mM, comprising about 2 mg/mL of CPD1 $NH_2$ or any pharmaceutically acceptable salt thereof, and the pH is between about pH 7.0 to about pH 8.2, preferably about pH 7.0.

106. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of formula A, wherein the pH is between about pH 7.0 and about pH 8.0, preferably about pH 8.0.

107. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of formula B, wherein the pH is between about pH 7.0 and about pH 8.0, preferably about pH 8.0.

108. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of SEQ ID NO: 1, wherein the pH is between about pH 7.0 and about pH 8.0, preferably about pH 8.0.

109. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of Formula A, wherein the pH is between about pH 7.0 and about pH 8.0, preferably about pH 8.0.

110. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist comprises an amino acid sequence of Formula B wherein the pH is between about pH 7.0 and about pH 8.0, preferably about pH 8.0.

111. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist is CPD1 OH or any pharmaceutically acceptable salt thereof, wherein the pH is between about pH 7.0 and about pH 8.0, preferably about pH 8.0.

112. The isotonic parenteral pharmaceutical composition of any one of the preceding aspects, wherein said buffer component is a phosphate buffer at a final concentration of about 15 mM to about 25 mM, preferably about 20 mM, said one or more tonicity agent is mannitol, such as D-mannitol, at a final concentration of about 190 mM to about 240 mM, preferably about 230 mM and said one or more GLP-1/GLP-2 dual agonist is CPD1 $NH_2$ or any pharmaceutically acceptable salt thereof, wherein the pH is between about pH 7.0 and about pH 8.0, preferably about pH 8.0.

113. The isotonic parenteral pharmaceutical composition of any one of the preceding aspects, wherein said composition provides a chemical stability in % of said one or more GLP-1/GLP-2 dual agonist or any pharmaceutically acceptable salt thereof, of at least 99% on day 3, and/or at least 98% on day 7, and/or at least 97% on day 14, and/or at least 95% on day 24, wherein said chemical stability is determined according to according to ASSAY Ill.

114. The isotonic parenteral pharmaceutical composition of any one of the preceding aspects, wherein said composition is selected from the list consisting of formulations of Table 5: Formulation 1, Formulation 2, Formulation 3, Formulation 4, Formulation 5, Formulation 5a, Formulation 6, Formulation 7, Formulation 8, Formulation 9, Formulation 13, Formulation 14, Formulation 15, Formulation 16, Formulation 17, Formulation 18, Formulation 19, Formulation 21.

TABLE 5

Formulation of this invention with a chemical stability in % of at least 99% on day 3, and/or at least 98% on day 7, and/or at least 97% on day 14, and/or at least 95% on day 24, wherein said chemical stability is determined according to according to ASSAY III.

| | | | Pharmaceutical composition ingredients (pH adjusted with NaOH or HCl as needed) | | |
| Formulation # | Tonicity agent | Phosphate buffer mM | Salt of CPD1 mg/mL | Concentration of tonicity agent | pH |
| --- | --- | --- | --- | --- | --- |
| 1 | mannitol | 20 | 2 | 190 | 8 |
| 2 | mannitol | 20 | 2 | 230 | 8 |
| 3 | mannitol | 20 | 0.2 | 270 | 8 |
| 4 | NaCl | 20 | 2 | 200 | 8 |
| 5 | NaCl | 20 | 2 | 140 | 8 |
| 6 | NaCl | 20 | 2 | 80 | 8 |
| 7 | KCl | 20 | 2 | 200 | 8 |
| 8 | KCl | 20 | 2 | 400 | 8 |
| 9 | KCl | 20 | 2 | 80 | 8 |
| 13 | mannitol | 20 | 2 | 230 | 7 |
| 14 | mannitol | 20 | 2 | 230 | 7.5 |
| 15 | mannitol | 20 | 2 | 230 | 8 |
| 16 | mannitol | 20 | 10 | 230 | 8 |

TABLE 5-continued

Formulation of this invention with a chemical stability in % of at least 99% on day 3, and/or at least 98% on day 7, and/or at least 97% on day 14, and/or at least 95% on day 24, wherein said chemical stability is determined according to according to ASSAY III.

Pharmaceutical composition ingredients
(pH adjusted with NaOH or HCl as needed)

| Formulation # | Tonicity agent | Phosphate buffer mM | Salt of CPD1 mg/mL | Concentration of tonicity agent | pH |
|---|---|---|---|---|---|
| 17 | mannitol | 100 | 2 | 230 | 8 |
| 18 | mannitol | 100 | 10 | 230 | 8 |
| 19 | mannitol | 20 | 0.2 | 230 | 7.5 |
| 21 | None | 20 | 1 | 230 | 7 |
| 5a | NaCl 150 | 20 | 1 | 150 | 7 |

115. The isotonic parenteral pharmaceutical composition of any one of the preceding aspects, wherein said composition is selected from the list consisting of formulations of Table 6: Formulation 1, Formulation 2, Formulation 3, Formulation 4, Formulation 5, Formulation 6, Formulation 7, Formulation 8, Formulation 9, Formulation 13, Formulation 14, Formulation 15, Formulation 16, Formulation 17, Formulation 18, Formulation 19.

116. The isotonic parenteral pharmaceutical composition of any one of the preceding aspects, wherein said composition provides a chemical stability in % of said one or more GLP-1/GLP-2 dual agonist of at least 99% on day 3, and/or at least 98% on day 7, and/or at least 97% on day 14, wherein said chemical stability is determined according to according to ASSAY Ill.

TABLE 6

Formulation of this invention- Formulation of this invention with a chemical stability in % of at least 99% on day 3, and/or at least 98% on day 7, and/or at least 97% on day 14, wherein said chemical stability is determined according to according to ASSAY III.

Pharmaceutical composition ingredients
(pH adjusted with NaOH or HCl as needed)

| Formulation # | Tonicity agent | Phosphate buffer mM | Salt of CPD1 mg/mL | Concentration of tonicity agent | pH |
|---|---|---|---|---|---|
| 1 | mannitol | 20 | 2 | 190 | 8 |
| 2 | mannitol | 20 | 2 | 230 | 8 |
| 3 | mannitol | 20 | 0.2 | 270 | 8 |
| 4 | NaCl | 20 | 2 | 200 | 8 |
| 5 | NaCl | 20 | 2 | 140 | 8 |
| 6 | NaCl | 20 | 2 | 80 | 8 |
| 7 | KCl | 20 | 2 | 200 | 8 |
| 8 | KCl | 20 | 2 | 400 | 8 |
| 9 | KCl | 20 | 2 | 80 | 8 |
| 13 | mannitol | 20 | 2 | 230 | 7 |
| 14 | mannitol | 20 | 2 | 230 | 7.5 |
| 15 | mannitol | 20 | 2 | 230 | 8 |
| 16 | mannitol | 20 | 10 | 230 | 8 |
| 17 | mannitol | 100 | 2 | 230 | 8 |
| 18 | mannitol | 100 | 10 | 230 | 8 |
| 19 | mannitol | 20 | 0.2 | 230 | 7.5 |

117. The isotonic parenteral pharmaceutical composition of any one of the preceding aspects, wherein said composition is selected from the list consisting of formulations of Table 7: Formulation 1, Formulation 2, Formulation 3, Formulation 4, Formulation 5, Formulation 6, Formulation 7, Formulation 8, Formulation 9, Formulation 13, Formulation 14, Formulation 15, Formulation 16, Formulation 17, Formulation 18, Formulation 19.

118. The isotonic parenteral pharmaceutical composition of any one of the preceding aspects, wherein said composition provides a chemical stability in % of said one or more GLP-1/GLP-2 dual agonist of at least 99% on day 3, and/or at least 98% on day 7, and/or at least 97% on day 14, wherein said chemical stability is determined according to according to ASSAY III.

TABLE 7

Formulation of this invention- Formulation of this invention with a chemical stability in % of at least 99% on day 3, and/or at least 98% on day 7, and/or at least 97% on day 14, wherein said chemical stability is determined according to according to ASSAY III.

Pharmaceutical composition ingredients
(pH adjusted with NaOH or HCl as needed)

| Formulation # | Tonicity agent | Phosphate buffer mM | Salt of CPD1 mg/mL | Concentration of tonicity agent | pH |
|---|---|---|---|---|---|
| 1 | mannitol | 20 | 2 | 190 | 8 |
| 2 | mannitol | 20 | 2 | 230 | 8 |
| 3 | mannitol | 20 | 0.2 | 270 | 8 |
| 4 | NaCl | 20 | 2 | 200 | 8 |
| 5 | NaCl | 20 | 2 | 140 | 8 |
| 6 | NaCl | 20 | 2 | 80 | 8 |
| 7 | KCl | 20 | 2 | 200 | 8 |
| 8 | KCl | 20 | 2 | 400 | 8 |
| 9 | KCl | 20 | 2 | 80 | 8 |
| 13 | mannitol | 20 | 2 | 230 | 7 |
| 14 | mannitol | 20 | 2 | 230 | 7.5 |
| 15 | mannitol | 20 | 2 | 230 | 8 |
| 16 | mannitol | 20 | 10 | 230 | 8 |
| 17 | mannitol | 100 | 2 | 230 | 8 |
| 18 | mannitol | 100 | 10 | 230 | 8 |
| 19 | mannitol | 20 | 0.2 | 230 | 7.5 |

119. The isotonic parenteral pharmaceutical composition of any one of the preceding aspects, wherein said composition is selected from the list consisting of formulations of Table 8: Formulation 1, Formulation 2, Formulation 3, Formulation 13, Formulation 14, Formulation 15, Formulation 16, Formulation 17, Formulation 18, Formulation 19.

120. The isotonic parenteral pharmaceutical composition of any one of the preceding aspects, wherein said composition provides a chemical stability in % of said one or more GLP-1/GLP-2 dual agonist of at least 99% on day 3, and/or at least 98% on day 7, and/or at least 97% on day 14, wherein said chemical stability is determined according to according to ASSAY III.

TABLE 8

Formulation of this invention- Formulation of this invention comprising mannitol as tonicity agent with a chemical stability in % of at least 99% on day 3, and/or at least 98% on day 7, and/or at least 97% on day 14, wherein said chemical stability is determined according to according to ASSAY III.

Pharmaceutical composition ingredients
(pH adjusted with NaOH or HCl as needed)

| Formulation # | Tonicity agent | Phosphate buffer mM | Salt of CPD1 mg/mL | Concentration of tonicity agent | pH |
|---|---|---|---|---|---|
| 1 | mannitol | 20 | 2 | 190 | 8 |
| 2 | mannitol | 20 | 2 | 230 | 8 |

41

TABLE 8-continued

Formulation of this invention- Formulation of this invention
comprising mannitol as tonicity agent with a chemical stability
in % of at least 99% on day 3, and/or at least 98% on day 7,
and/or at least 97% on day 14, wherein said chemical stability
is determined according to according to ASSAY III.

Pharmaceutical composition ingredients
(pH adjusted with NaOH or HCl as needed)

| Formulation # | Tonicity agent | Phosphate buffer mM | Salt of CPD1 mg/mL | Concentration of tonicity agent | pH |
|---|---|---|---|---|---|
| 3 | mannitol | 20 | 0.2 | 270 | 8 |
| 13 | mannitol | 20 | 2 | 230 | 7 |
| 14 | mannitol | 20 | 2 | 230 | 7.5 |
| 15 | mannitol | 20 | 2 | 230 | 8 |
| 16 | mannitol | 20 | 10 | 230 | 8 |
| 17 | mannitol | 100 | 2 | 230 | 8 |
| 18 | mannitol | 100 | 10 | 230 | 8 |
| 19 | mannitol | 20 | 0.2 | 230 | 7.5 |

121. The isotonic parenteral pharmaceutical composition of any one of the preceding aspects, wherein said composition comprises mannitol, such as D-mannitol and is selected from the list consisting of formulations of Table 9: Formulation 4, Formulation 5, Formulation 6, Formulation 7, Formulation 8, Formulation 9.

TABLE 9

Formulation of this invention- Formulation of this invention
comprising salt as tonicity agent, with a chemical stability
in % of at least 99% on day 3, and/or at least 98% on day
7, and/or at least 97% on day 14, wherein said chemical stability
is determined according to according to ASSAY III.

Pharmaceutical composition ingredients
(pH adjusted with NaOH or HCl as needed)

| Formulation # | Tonicity agent | Phosphate buffer mM | Salt of CPD1 mg/mL | Concentration of tonicity agent | pH |
|---|---|---|---|---|---|
| 4 | NaCl | 20 | 2 | 200 | 8 |
| 5 | NaCl | 20 | 2 | 140 | 8 |
| 6 | NaCl | 20 | 2 | 80 | 8 |
| 7 | KCl | 20 | 2 | 200 | 8 |
| 8 | KCl | 20 | 2 | 400 | 8 |
| 9 | KCl | 20 | 2 | 80 | 8 |

122. The isotonic parenteral pharmaceutical composition of any one of the preceding aspects, wherein said composition provides a chemical stability in % of said one or more GLP-1/GLP-2 dual agonist of at least 100% on day 3, and/or at least 99% on day 7, and/or at least 98% on day 14 and/or optionally at least 96% at day 24, wherein said chemical stability is determined according to according to ASSAY Ill.

123. The isotonic parenteral pharmaceutical composition of any one of the preceding aspects, wherein said composition comprises mannitol, such as D-mannitol and is selected from the list consisting of formulations of Formulation 13, Formulation 15 and Formulation 16 as disclosed in Table 8.

124. The isotonic parenteral pharmaceutical composition of any one of the preceding aspects, wherein said composition is Formulation 1 as in Table 7 or 8.

125. The isotonic parenteral pharmaceutical composition of any one of the preceding aspects, wherein said composition is Formulation 2 as disclosed in Table 7 or 8.

126. The isotonic parenteral pharmaceutical composition of any one of the preceding aspects, wherein said composition is Formulation 3 as disclosed in Table 7 or 8.

127. The isotonic parenteral pharmaceutical composition of any one of the preceding aspects, wherein said composition is Formulation 4 as disclosed in Table 7.

128. The isotonic parenteral pharmaceutical composition of any one of the preceding aspects, wherein said composition is Formulation 5 as disclosed in Table 7.

129. The isotonic parenteral pharmaceutical composition of any one of the preceding aspects, wherein said composition is Formulation 6 as disclosed in Table 7.

130. The isotonic parenteral pharmaceutical composition of any one of the preceding aspects, wherein said composition is Formulation 7 as disclosed in Table 7.

131. The isotonic parenteral pharmaceutical composition of any one of the preceding aspects, wherein said composition is Formulation 8 as disclosed in Table 7.

132. The isotonic parenteral pharmaceutical composition of any one of the preceding aspects, wherein said composition is Formulation 9 as disclosed in Table 7.

133. The isotonic parenteral pharmaceutical composition of any one of the preceding aspects, wherein said composition is Formulation 13 as disclosed in Table 7 or 8.

134. The isotonic parenteral pharmaceutical composition of any one of the preceding aspects, wherein said composition is Formulation 14 as disclosed in Table 7 or 8.

135. The isotonic parenteral pharmaceutical composition of any one of the preceding aspects, wherein said composition is Formulation 14 as disclosed in Table 7 or 8, wherein said GLP-1/GLP-2 dual agonist is CPD1OH.

136. The isotonic parenteral pharmaceutical composition of any one of the preceding aspects, wherein said composition is Formulation 14 as disclosed in Table 7 or 8, wherein said GLP-1/GLP-2 dual agonist is CPD1NH$_2$.

137. The isotonic parenteral pharmaceutical composition of any one of the preceding aspects, wherein said composition is Formulation 15 as disclosed in Table 7 or 8.

138. The isotonic parenteral pharmaceutical composition of any one of the preceding aspects, wherein said composition is Formulation 15 as disclosed in Table 7 or 8, wherein said GLP-1/GLP-2 dual agonist is CPD1OH.

139. The isotonic parenteral pharmaceutical composition of any one of the preceding aspects, wherein said composition is Formulation 15 as disclosed in Table 7 or 8, wherein said GLP-1/GLP-2 dual agonist is CPD1NH$_2$.

140. The isotonic parenteral pharmaceutical composition of any one of the preceding aspects, wherein said composition is Formulation 16 as disclosed in Table 7.

141. The isotonic parenteral pharmaceutical composition of any one of the preceding aspects, wherein said composition is Formulation 17 as disclosed in Table 7 or 8.

142. The isotonic parenteral pharmaceutical composition of any one of the preceding aspects, wherein said composition is Formulation 18 as disclosed in Table 7 or 8.

143. The isotonic parenteral pharmaceutical composition of any one of the preceding aspects, wherein said composition is Formulation 19 as disclosed in Table 7 or 8.

144. The isotonic parenteral pharmaceutical composition of any one of the preceding aspects, optionally further comprising a preservative.

145. The isotonic parenteral pharmaceutical composition of any one of the preceding aspects, wherein said preservative is present in a concentration of about 0.1 to about 10 mg/mL.

146. The isotonic parenteral pharmaceutical composition of any one of the preceding aspects, wherein said preservative is present in a concentration of about 1 to about 5 mg/mL.

147. The isotonic parenteral pharmaceutical composition of any one of the preceding aspects, wherein said preservative is present in a concentration of about 2.5 to about 4 mg/mL.

148. The isotonic parenteral pharmaceutical composition of any one of the preceding aspects, not comprising a preservative.

149. The isotonic parenteral pharmaceutical composition of any one of the preceding aspects, wherein said pH is between about pH 7.0 and about pH 8.0, and wherein said one or more GLP-1/GLP-2 agonist is predominantly present in its trimeric form.

150. The isotonic parenteral pharmaceutical composition of any one of the preceding aspects, wherein said pH is between about pH 7.0 and about pH 8.0, and wherein about 94% or more of said one or more GLP-1/GLP-2 agonist is in a trimeric form.

151. The isotonic parenteral pharmaceutical composition of any one of the preceding aspects, wherein said pH is between about pH 7.0 and about pH 8.0 and wherein about 94% or more of said one or more GLP-1/GLP-2 agonist is in a trimeric form and less than about 6% or less of said one or more GLP-1/GLP-2 dual agonist is in a tetrameric, octameric, 18-meric or 27-meric form.

152. The isotonic parenteral pharmaceutical composition of any one of the preceding aspects, wherein said composition comprises the ingredients:

| Component | Amount per mL (CPD1) | Function |
|---|---|---|
| CPD1 | 0-5 mg | Drug Substance |
| Na$_2$HPO$_4$ (anhydrous) Disodium phosphate, anhydrous/ Dibasic sodium phosphate, anhydrous | 1-5 mg | Buffer component |
| NaH$_2$PO$_4$ (anhydrous) Sodium dihydrogen phosphate, anhydrous/Monobasic sodium phosphate, anhydrous | 0-1 mg | Buffer component |
| Mannitol (D-mannitol) | 35-50 mg | Tonicity agent |
| Hydrochloric acid | pH adjustment | to about pH 8 |
| Sodium Hydroxide | pH adjustment | to about pH 8 |
| Water for Injections | To make 1 mL | Solvent |

153. The isotonic parentera pharmaceutical composition o any one o the preceding aspects, wherein said composition comprises the ingredients:

| Component | Amount per mL (CPD1) | Function |
|---|---|---|
| CPD1 | 5-10 mg | Drug Substance |
| Na$_2$HPO$_4$ (anhydrous) Disodium phosphate, anhydrous/ Dibasic sodium phosphate, anhydrous | 1-5 mg | Buffer component |
| NaH$_2$PO$_4$ (anhydrous) Sodium dihydrogen phosphate, anhydrous/Monobasic sodium phosphate, anhydrous | 0-1 mg | Buffer component |
| Mannitol (D-mannitol) | 35-50 mg | Tonicity agent |
| Hydrochloric acid | pH adjustment | to about pH 8 |
| Sodium Hydroxide | pH adjustment | to about pH 8 |
| Water for Injections | To make 1 mL | Solvent |

154. The isotonic parenteral pharmaceutical composition of any one of the preceding aspects, wherein said composition comprises the ingredients:

| Component | Amount per mL (CPD1OH) | Function |
|---|---|---|
| CPD1OH | About 2 mg | Drug Substance |
| Na$_2$HPO$_4$ (anhydrous) Disodium phosphate, anhydrous/ Dibasic sodium phosphate, anhydrous | About 2-3 mg | Buffer component |
| NaH$_2$PO$_4$ (anhydrous) Sodium dihydrogen phosphate, anhydrous/Monobasic sodium phosphate, anhydrous | About 0-0.5 mg | Buffer component |
| Mannitol (D-mannitol) | About 40-42 mg | Tonicity agent |
| Hydrochloric acid | pH adjustment | to about pH 8 |
| Sodium Hydroxide | pH adjustment | to about pH 8 |
| Water for Injections | To make 1 mL | Solvent |

155. The isotonic parenteral pharmaceutical composition of any one of the preceding aspects, wherein said composition comprises the ingredients:

| Component | Amount per mL (CPD1OH) | Function |
|---|---|---|
| CPD1OH | About 2 mg | Drug Substance |
| Na$_2$HPO$_4$ (anhydrous) Disodium phosphate, anhydrous/ Dibasic sodium phosphate, anhydrous | About 2-3 mg | Buffer component |
| NaH$_2$PO$_4$ (anhydrous) Sodium dihydrogen phosphate, anhydrous/Monobasic sodium phosphate, anhydrous | About 0-0.5 mg | Buffer component |
| Mannitol (D-mannitol) | About 40-42 mg | Tonicity agent |
| Hydrochloric acid | pH adjustment | to about pH 8 |
| Sodium Hydroxide | pH adjustment | to about pH 8 |
| Water for Injections | To make 1 mL | Solvent |

156. The isotonic parenteral pharmaceutical composition of any one of the preceding aspects, wherein said composition comprises the ingredients:

| Component | Amount per mL (CPD1NH$_2$ or CPD1OH) | Function |
|---|---|---|
| CPD1NH$_2$ or CPD1OH | 2 mg | Drug Substance |
| Na$_2$HPO$_4$ (anhydrous) Disodium phosphate, anhydrous/ Dibasic sodium phosphate, anhydrous | 2.65 mg | Buffer component |
| NaH$_2$PO$_4$ (anhydrous) Sodium dihydrogen phosphate, anhydrous/Monobasic sodium phosphate, anhydrous | 0.16 mg | Buffer component |

-continued

| Component | Amount per mL (CPD1NH$_2$ or CPD1OH) | Function |
|---|---|---|
| Mannitol (D-mannitol) | 41.90 mg | Tonicity agent |
| Hydrochloric acid | pH adjustment to about pH 8 | |
| Sodium Hydroxide | pH adjustment to about pH 8 | |
| Water for Injections | To make 1 mL | Solvent |

157. The isotonic parenteral pharmaceutical composition of any one of the preceding aspects, wherein said composition comprises the ingredients:

| Component | Amount per mL (CPD1NH$_2$ or CPD1OH) | Function |
|---|---|---|
| CPD1NH$_2$ or CPD1OH | 10 mg | Drug Substance |
| Na$_2$HPO$_4$ (anhydrous) Disodium phosphate, anhydrous/ Dibasic sodium phosphate, anhydrous | 2.65 mg | Buffer component |
| NaH$_2$PO$_4$ (anhydrous) Sodium dihydrogen phosphate, anhydrous/Monobasic sodium phosphate, anhydrous | 0.16 mg | Buffer component |
| Mannitol (D-mannitol) | 41.90 mg | Tonicity agent |
| Hydrochloric acid | pH adjustment to about pH 8 | |
| Sodium Hydroxide | pH adjustment to about pH 8 | |
| Water for Injections | To make 1 mL | Solvent |

158. The isotonic parenteral pharmaceutical composition of any one of the preceding aspects, suitable for injection in a single use device.

159. The isotonic parenteral pharmaceutical composition of any one of the preceding aspects, suitable for parenteral administration performed by subcutaneous, intramuscular or intravenous injection by means of a syringe, optionally a pen-like syringe.

160. The isotonic parenteral pharmaceutical composition of any one of the preceding aspects, which is suitable for s.c. or i.v. injection into human subjects.

161. The isotonic parenteral pharmaceutical composition of any one of the preceding aspects administered by s.c. injection into human subjects.

162. The isotonic parenteral pharmaceutical composition of any one of the preceding aspects administered by i.v. injection into human subjects.

163. The isotonic parenteral pharmaceutical composition of any one of the preceding aspects, delivered in a single use injection device, wherein said single use device is selected from an injector pen or single use syringe.

164. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 100% at day 3 (D3), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

165. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 99% or higher at day 3 (D3), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

166. The pharmaceutical compositions of any one of the preceding aspects, comprising about 1 mg/mL to about 15 mg/mL, preferable about 1 mg/mL to about 10 mg/mL of one or more GLP-1/GLP-2 dual agonist, having a chemical stability in %, in compositions stored at 40° C., of said one or more GLP-1/GLP-2 dual agonist of about 99% at day 3 (D3), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

167. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 99% at day 7 (D7), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

168. The pharmaceutical compositions of any one of the preceding aspects, comprising about 1 mg/mL to about 15 mg/mL, preferable about 1 mg/mL to about 10 mg/mL of one or more GLP-1/GLP-2 dual agonist, having a chemical stability in %, in compositions stored at 40° C., of said one or more GLP-1/GLP-2 dual agonist of about 98% or higher at day 7 (D7), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

169. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 98% at day 7 (D7), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

170. The pharmaceutical compositions of any one of the preceding aspects, comprising about 1 mg/mL to about 15 mg/mL of one or more GLP-1/GLP-2 dual agonist, having a chemical stability in %, in compositions stored at 40° C., of said one or more GLP-1/GLP-2 dual agonist of about 97.5% at day 7 (D7), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

171. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 98% at day 14 (D14), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

172. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 97% or higher at day 14 (D14), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

173. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 96% at day 14 (D14), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

174. The pharmaceutical compositions of any one of the preceding aspects, comprising about 1 mg/mL to about 15 mg/mL, preferably about 1 mg/mL to about 10 mg/mL, having a chemical stability in %, in compositions stored at 40° C., of said one or more GLP-1/GLP-2 dual agonist of about 96.5% at day 14 (D14), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

175. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 96% at day 24 (D24), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

176. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 96% or higher at day 24 (D24), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

177. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of about 95.5% at day 24 (D24), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

178. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of at least about 94.5% on day 24 (D24), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

179. The pharmaceutical compositions of any one of the preceding aspects, comprising about 1 mg/mL to about 15 mg/mL, preferably about 1 mg/mL to about 10 mg/mL of one or more GLP-1/GLP-2 dual agonist, having a chemical stability in %, in compositions stored at 40° C., of said one or more GLP-1/GLP-2 dual agonist of at least about 85% measured 3 months after day 0 (3M), wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 40° C.

180. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 97%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

181. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 97%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

182. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 97%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

183. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 98%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

184. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 98%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

185. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 98%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

186. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 99%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

187. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 99%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

188. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 99%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

189. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 100%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

190. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 100%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 5° C.

191. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

192. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured at 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

193. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 100%, measured at 9 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

194. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 100%, measured at 9 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

195. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured at 9 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

196. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 100%, measured at 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

197. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 100%, measured at 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

198. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured at 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

199. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

200. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

201. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

202. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 100%, measured at 1 month after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

203. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 100%, measured at 1 month after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

204. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured at 1 month after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

205. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 100%, measured at 2 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

206. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 100%, measured at 2 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

207. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured at 2 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

208. The pharmaceutical compositions of any one of the preceding aspects comprising about 1 mg/mL to about 15 mg/mL of one or more GLP-1/GLP-2 dual agonist, having a chemical stability in %, in compositions stored at 5° C., of at least about 100%, measured at 10 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

209. The pharmaceutical compositions of any one of the preceding aspects comprising about 2 mg/mL to about 10 mg/mL of one or more GLP-1/GLP-2 dual agonist, having a chemical stability in %, in compositions stored at 5° C., of at least about 100%, measured at 10 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

210. The pharmaceutical compositions of any one of the preceding aspects comprising about 2 mg/mL or about 10 mg/mL of one or more GLP-1/GLP-2 dual agonist, having a chemical stability in %, in compositions stored at 5° C., of at least about 100%, measured at 10 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 5° C.

211. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of at least about 91%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

212. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of at least about 91%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

213. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of at least about 91%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 25° C.

214. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of at least about 94%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 25° C.

215. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of at least about 94%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 25° C.

216. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of at least about 94%, measured over 1 to 12 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 25° C.

217. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of at least about 94%, measured at 9 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

218. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of at least about 94%, measured at 9 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

219. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of at least about 94%, measured at 9 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

220. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of at least about 96%, measured at 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

221. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of at least about 96%, measured at 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

222. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of at least about 96%, measured at 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

223. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of at least about 96%, measured over 1 to 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 25° C.

224. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of at least about 96%, measured over 1 to 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/ GLP-2 dual agonist purity on day 0 at 25° C.

225. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of at least about 96%, measured over 1 to 6 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

226. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of at least about 98-100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

227. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of at least about 98-100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

228. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of at least about 98-100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

229. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of at least about 99-100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

230. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of at least about 99-100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

231. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of at least about 99-100%, measured over 1 to 3 months after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

232. The pharmaceutical compositions of any one of the preceding aspects comprising about 1 mg/mL to about 15 mg/mL of one or more GLP-1/GLP-2 dual agonist, having a chemical stability in %, in compositions stored at 25° C., of about 100%, measured at 1 month after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

233. The pharmaceutical compositions of any one of the preceding aspects comprising about 2 mg/mL to about 10 mg/mL of one or more GLP-1/GLP-2 dual agonist, having a chemical stability in %, in compositions stored at 25° C., of about 100%, measured at 1 month after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

234. The pharmaceutical compositions of any one of the preceding aspects comprising about 2 mg/mL or about 10 mg/mL of one or more GLP-1/GLP-2 dual agonist, having a chemical stability in %, in compositions stored at 25° C., of about 100%, measured at 1 month after day 0, wherein said chemical stability is determined by HPLC, such as RP-HPLC according to ASSAY Ill as disclosed herein, or equivalent methods, and wherein said chemical stability is expressed as the relative GLP-1/GLP-2 dual agonist purity expressed in % relative to the absolute GLP-1/GLP-2 dual agonist purity on day 0 at 25° C.

235. The isotonic parenteral pharmaceutical composition of any one of the preceding aspects, having a retained chemical and/or physical stability of said one or more GLP-1/GLP-2 dual agonist.

236. The isotonic parenteral pharmaceutical composition of any one of the preceding aspects, administered by s.c. injection into human subjects, in a volume allowing for a total amount of about 0.1 mg or more of GLP-1/GLP-2 dual agonist to be delivered to said subject.

237. The isotonic parenteral pharmaceutical composition of any one of the preceding aspects, administered by s.c. injection into human subjects, in a volume allowing for a total amount of about 0.3 mg or more of said one or more GLP-1/GLP-2 dual agonist to be delivered to said subject.

238. The isotonic parenteral pharmaceutical composition of any one of the preceding aspects, administered by s.c. injection into human subjects, in a volume allowing for a total amount of about 1 mg or more of said one or more GLP-1/GLP-2 dual agonist to be delivered to said subject.

239. The isotonic parenteral pharmaceutical composition of any one of the preceding aspects, administered by s.c. injection into human subjects, in a volume allowing for a total amount of about 3 mg or more of said one or more GLP-1/GLP-2 dual agonist to be delivered to said subject.

240. The isotonic parenteral pharmaceutical composition of any one of the preceding aspects, administered by s.c. injection into human subjects, in a volume allowing for a total amount of about 6 mg or more of said one or more GLP-1/GLP-2 dual agonist to be delivered to said subject.

241. The isotonic parenteral pharmaceutical composition of any one of the preceding aspects, administered by s.c. injection into human subjects, in a volume allowing for a total amount of about 10 mg or more of said one or more GLP-1/GLP-2 dual agonist to be delivered to said subject.

242. The isotonic parenteral pharmaceutical composition of any one of the preceding aspects, administered by s.c. injection into human subjects, in a volume allowing for a total amount of about 0.1 mg to about 10 mg GLP-1/GLP-2 dual agonist to be delivered to said subject.

243. The isotonic parenteral pharmaceutical composition of any one of the preceding aspects, administered by s.c. injection into human subjects, in a volume allowing for a total amount of about 0.1 mg GLP-1/GLP-2 dual agonist to be delivered to said subject.

244. The isotonic parenteral pharmaceutical composition of any one of the preceding aspects, administered by s.c. injection into human subjects, in a volume allowing for a total amount of about 0.3 mg GLP-1/GLP-2 dual agonist to be delivered to said subject.

245. The isotonic parenteral pharmaceutical composition of any one of the preceding aspects, administered by s.c. injection into human subjects, in a volume allowing for a total amount of about 1 mg GLP-1/GLP-2 dual agonist to be delivered to said subject.

246. The isotonic parenteral pharmaceutical composition of any one of the preceding aspects, administered by s.c. injection into human subjects, in a volume allowing for a total amount of about 3 mg GLP-1/GLP-2 dual agonist to be delivered to said subject.

247. The isotonic parenteral pharmaceutical composition of any one of the preceding aspects, administered by s.c. injection into human subjects, in a volume allowing for a total amount of about 6 mg GLP-1/GLP-2 dual agonist to be delivered to said subject.

248. The isotonic parenteral pharmaceutical composition of any one of the preceding aspects, administered by s.c. injection into human subjects, in a volume allowing for a total amount of about 9 mg GLP-1/GLP-2 dual agonist to be delivered to said subject.

249. The isotonic parenteral pharmaceutical composition of any one of the preceding aspects, administered by s.c. injection into human subjects, in a volume allowing for a total amount of about 10 mg GLP-1/GLP-2 dual agonist to be delivered to said subject.

250. The isotonic parenteral pharmaceutical composition of any one of the preceding aspects, for use in a human subject in the need of prophylaxis or treatment of intestinal damage and dysfunction, regulation of body weight, and prophylaxis or treatment of metabolic dysfunction.

251. The isotonic parenteral pharmaceutical composition of any one of the preceding aspects, for use in a human subject in the need of prophylaxis or treatment of malabsorption, ulcers (e.g. peptic ulcers, Zollinger-Ellison Syndrome, drug-induced ulcers, and ulcers related to infections or other pathogens), short-bowel syndrome, cul-de-sac syndrome, inflammatory bowel disease (Crohns disease and ulcerative colitis), irritable bowel syndrome (IBS), pouchitis, celiac sprue (for example arising from gluten induced enteropathy or celiac disease), tropical sprue, hypogammaglobuline-mic sprue, mucositis induced by chemotherapy or radiation therapy, diarrhoea induced by chemotherapy or radiation therapy, low grade inflammation, meta-bolic endotoxemia, necrotising enterocolitis, primary biliary cirrhosis, hepatitis, fatty liver disease (including parental nutrition associated gut atrophy, PNALD (Par-enteral Nutrition-Associated Liver Disease), NAFLD (Non-Alcoholic Fatty Liver Disease) and NASH (Non-Alcoholic Steatohepatitis)), or gastrointestinal side-effects of inflammatory conditions such as pancreatitis or graft versus host disease (GVHD).

252. The isotonic parenteral pharmaceutical composition of any one of the preceding aspects, for use in a human subject in the need of prophylaxis or treatment of obesity, morbid obesity, obesity-linked gallbladder dis-ease, obesity-induced sleep apnoea, inadequate glucose control, glucose tolerance, dyslipidaemia (e.g. elevated LDL levels or reduced HDL/LDL ratio), diabetes (e.g. Type 2 diabetes, gestational diabetes), pre-diabetes, metabolic syndrome or hypertension.

253. The isotonic parenteral pharmaceutical composition of any one of the preceding aspects, for use in a human subject in the need of prophylaxis or treatment of intestinal dysfunction or damage caused by or associ-ated with GVHD, as well as prophylaxis or treatment of side effects such as diarrhoea caused by or associated with GVHD.

254. The isotonic parenteral pharmaceutical composition of any one of the preceding aspects, for use in a human subject in the need of prophylaxis or treatment of obesity, morbid obesity, obesity-linked gallbladder dis-ease and obesity-induced sleep apnoea.

255. The isotonic parenteral pharmaceutical composition of any one of the preceding aspects, for use in a human subject in the need of prophylaxis or treatment need of improving glucose tolerance and/or glucose control. In some aspects, a pharmaceutical composition of this invention is administered to human subjects in the need of modulating (e.g. improving) circulating cholesterol levels, being capable of lowering circulating triglycer-ide or LDL levels, and increasing HDL/LDL ratio.

256. The isotonic parenteral pharmaceutical composition of any one of the preceding aspects, administered to a human subject to facilitate the biological effects selected from the group consisting of: increasing intes-tinal mass, improving intestinal function (especially intestinal barrier function), increasing intestinal blood flow, repairing intestinal damage or dysfunction in a subject in need thereof.

The invention is also described in the following aspects:

1. An isotonic parenteral pharmaceutical composition, comprising:
   a. at least about 1 mg/mL of one or more GLP-1/GLP-2 dual agonist comprising general formula A:

H[Aib]EG-X5-F-X7-SELATILD-[ψ]-QAARDFI-
   AWLI-X28-X29-KITD    (A) (SEQ ID NO: 2), wherein X5 is T or S; X7 is T or S; X28 is Q, E, A, H, Y, L, K, R or S; X29 is H and at least one of X5 and X7 is T, and wherein [ψ]indicates an L or D lysine residue in which an albumin binding moiety is conjugated to the GLP-1/GLP-2 dual agonist, and wherein said albumin binding moiety is [K([17-carboxy-heptadecanoyl]-isoGlu)]; and
   b. about 20 mM to about 200 mM of buffer component; and
   c. about 1 mM to about 360 mM of one or more tonicity agent, preferably about 150 mM to about 250 mM of one or more tonicity agent, wherein said one or more tonicity agent is an ionic or a non-ionic tonicity agent, wherein the ionic tonicity agent is selected from the group consisting of salts, alkali metals or earth metal halides, and the non-ionic tonicity agent is mannitol, such as D-mannitol, wherein said composition further comprises a solvent, and wherein said composition has a pH of about pH 6.0 to about pH 8.2, preferably a pH of about pH 7.0 to about pH 8.0.

2. The isotonic parenteral pharmaceutical composition of aspect 1, comprising about 150 mM to about 250 mM of one or more tonicity agent, wherein said one or more tonicity agent is an ionic tonicity agent, selected from the group consisting of $CaCl_2$, KBr, KCl, LiCl, NaI, NaBr, NaCl or $Na_2SO_4$, preferably wherein the ionic tonicity agent is NaCl or KCl.

3. The parenteral pharmaceutical composition of any one of the preceding aspects wherein said one or more GLP-1/GLP-2 dual agonist comprising general formula A is of the general formula B:

H[Aib]EG-X5-FT-SELATILD-[ψ]-QAARDFIAWLI-
   X28-HKITD    (B)(SEQ ID NO: 3), wherein X5 is T or S; X28 is Q, E, A, H, Y, L, K, R or S and wherein [ψ]indicates an L or D lysine residue in which the albumin binding moiety is conjugated to the GLP-1/GLP-2 dual agonist and wherein said albumin binding moiety is [K([17-carboxy-heptadecanoyl]-isoGlu)].

4. The isotonic parenteral pharmaceutical composition of any one of the preceding aspects, wherein said one or more GLP-1/GLP-2 dual agonist comprising general formula A or B comprises the sequence: H[Aib] EGSFTSELATILD[ψ]QAARDFIAWLIQHKITD (SEQ ID NO: 1).

5. The isotonic parenteral pharmaceutical composition according to any one of the preceding aspects, wherein said one or more GLP-1/GLP-2 dual agonist comprising general formula A or B is:
   a. Hy-H[Aib]EGSFTSELATILD[K([17-carboxy-hep-tadecanoyl]-isoGlu)]QAARDFIAWLIQHKITD-OH (CPD10H) (SEQ ID NO: 1); or
   b. Hy-H[Aib]EGSFTSELATILD[K([17-carboxy-hep-tadecanoyl]-isoGlu)]QAARDFIAWLIQHKITD-$NH_2$ (CPD1 $NH_2$) (SEQ ID NO: 1).

6. The isotonic parenteral pharmaceutical composition according to any one of the preceding aspects, wherein said buffer component is selected from the group consisting of phosphate buffer, citrate buffer, histidine buffer, tris buffer or bis tris, or a combination thereof, preferably selected from the group consisting of phosphate buffer, citrate buffer, tris buffer or bis tris, or a combination thereof.

7. The isotonic parenteral pharmaceutical composition of any one of the preceding aspects, wherein said buffer component is a sodium phosphate buffer.

8. The isotonic parenteral pharmaceutical composition of any one of the preceding aspects, wherein the osmolality of the composition is about 230 mOsmol/kg to about 370 mOsmol/kg.

9. The isotonic parenteral pharmaceutical composition of any one of the preceding aspects, wherein said buffer component is a phosphate buffer at a final concentration of about 15 mM to about 200 mM, preferably about 20 mM, said one or more tonicity agent is mannitol, preferably D-mannitol at a final concentration of about 190 mM to about 240 mM, preferably about 230 mM, and said one or more GLP-1/GLP-2 dual agonist comprises SEQ ID NO: 1 or any pharmaceutically acceptable salt thereof, wherein the pH is between about 7.0 and about 8.0, preferably about 8.0.

10. The isotonic parenteral pharmaceutical composition of any one of the preceding aspects, wherein said buffer component is a phosphate buffer at a final concentration of about 15 mM to about 30 mM, said one or more tonicity agent is mannitol, preferably D-mannitol at a final concentration of about 230 mM and said one or more GLP-1/GLP-2 dual agonist comprises SEQ ID NO: 1 or any pharmaceutically acceptable salt thereof, wherein the pH is between about 7.0 and about 8.0, preferably about 8.0.

11. The isotonic parenteral pharmaceutical composition of any one of the preceding aspects, wherein said one or more GLP-1/GLP-2 dual agonist is present at a concentration of about 1 mg/mL to about 15 mg/mL.

12. The isotonic parenteral pharmaceutical composition of any one of the preceding aspects, comprising SEQ ID NO: 1 or a chloride salt thereof, a phosphate buffer at a concentration of about 15 mM to about 30 mM, preferably about 20 mM, mannitol preferably D-mannitol at a concentration of about 230 mM, water for injection and sodium hydroxide and/or hydrochloric acid for pH adjustment to a pH of about pH 8.0, wherein said one or more GLP-1/GLP-2 dual agonist is CPD1OH or CPD1 $NH_2$, preferably Hy-H[Aib] EGSFTSELATILD[K([17-carboxy-heptadecanoyl]-isoGlu)]QAARDFIAWLIQHKITD-OH (CPD1OH) (SEQ ID NO: 1) and is present at about 2 mg/mL.

13. The isotonic parenteral pharmaceutical composition of any one of the preceding aspects, comprising SEQ ID NO: 1 or a chloride salt thereof, a phosphate buffer at a concentration of about 15 mM to about 30 mM, preferably about 20 mM, mannitol preferably D-mannitol at a concentration of about 230 mM, water for injection and sodium hydroxide and/or hydrochloric acid for pH adjustment to a pH of about pH 8.0, wherein said one or more GLP-1/GLP-2 dual agonist is CPD1 OH or CPD1 $NH_2$, preferably Hy-H[Aib] EGSFTSELATILD[K([17-carboxy-heptadecanoyl]-isoGlu)]QAARDFIAWLIQHKITD-OH (CPD1OH) (SEQ ID NO: 1) and is present at about 10 mg/mL.

14. The isotonic parenteral pharmaceutical composition of aspects 12 or 13, wherein said one or more GLP-1/GLP-2 dual agonist is Hy-H[Aib]EGSFTSELATILD[K([17-carboxy-heptadecanoyl]-isoGlu)]QAARDFI-AWLIQHKITD-OH (CPD10H) (SEQ ID NO: 1).

15. The isotonic parenteral pharmaceutical composition of any one of the preceding aspects, which is suitable for s.c. or i.v. injection into human subjects.

16. The isotonic parenteral pharmaceutical composition of any one of the preceding aspects, for use in:

(i) increasing intestinal mass, improving intestinal function, increasing intestinal blood flow, or repairing intestinal damage or dysfunction, in a subject in need thereof; or (ii) the prophylaxis or treatment of malabsorption, ulcers, short-bowel syndrome, cul-de-sac syndrome, inflammatory bowel disease, irritable bowel syndrome, pouchitis, celiac sprue, tropical sprue, hypogammaglobulinemic sprue, mucositis induced by chemotherapy or radiation therapy, diarrhoea induced by chemotherapy or radiation therapy, low grade inflammation, metabolic endotoxemia, necrotising enterocolitis, primary biliary cirrhosis, hepatitis, fatty liver disease, or gastrointestinal side-effects of inflammatory conditions, in a subject in need thereof; or (iii) reducing or inhibiting weight gain, reducing gastric emptying or intestinal transit, reducing food intake, reducing appetite, or promoting weight loss, in a subject in need thereof; or (iv) the prophylaxis or treatment of obesity, morbid obesity, obesity-linked gallbladder disease, obesity-induced sleep apnoea, inadequate glucose control, glucose tolerance, dyslipidaemia, diabetes, pre-diabetes, metabolic syndrome or hypertension, in a subject in need thereof.

EXAMPLES

Example 1: Chemical Stability of Laboratory Scale Isotonic Compositions of this Invention Comprising CPD1

This example investigates the chemical stability of CPD1 expressed as the relative purity of the peptide peak (i.e. the main CPD1 peak) determined by HPLC at a given time point, and normalised to the absolute purity of the peptide peak (i.e. main CPD1 peak) at day zero (day 0 (DO)), which is set to 100% purity and thus chemical stability in % of said dual agonist.

CPD1 was produced according to ASSAY I, the pharmaceutical compositions (i.e. Formulations) where prepared and stored according to ASSAY II and the absolute CPD1 purity was measured by a HPLC, such as RP-HPLC according to ASSAY Ill at each time point (DX, wherein X is 0, 3, 7, 14 or 24 days). The chemical stability, i.e. the normalised CPD1 purity expressed in %, was determined according to the calculations described in ASSAY Ill. The Formulations, 1-24 comprise CPD1 OH, which is comprised of the amino acid sequence of formula A. CPD1 OH may be interchangeable with CPD1 NH$_2$.

The results show that formulations comprising mannitol, such as D-mannitol, as tonicity agent have a higher chemical stability (e.g. a high GLP-1/GLP-2 dual agonist purity, exemplified by CPD1) compared to all other tested formulations, including the formulation comprising no tonicity agent. Thus, mannitol, such as D-mannitol seems to be stabilising the chemical stability of the GLP-1/GLP-2 dual agonist. L-histidine, seems to counteract the stabilising effect of mannitol, such as D-mannitol to some extent. On the other hand, pH ranging from about 7.0 to about 8.0 does not seem affect the GLP-1/GLP-2 dual agonist's chemical stability much, when the isotonic parenteral pharmaceutical composition comprises mannitol, such as D-mannitol. The chemical stability does also seem to be relatively stable when changing the phosphate buffer concentration from about 20 mM to about 100 mM.

The results further show, that pharmaceutical compositions comprising salts, such as sodium chloride or potassium chloride as tonicity agents, have a high chemical stability, which is comparable to the stability of formulations without tonicity agent, and which are much better than the chemical stability of the GLP-1/GLP-2 dual agonist in pharmaceutical compositions comprising a tonicity agent selected from sucrose, dextrose, glycerol and propylene glycol.

Table 10 further illustrates that sucrose, dextrose, glycerol and propylene glycol reduce chemical stability, and thus are not an optimal choice for isotonic pharmaceutical compositions with compounds comprising formula A and certainly not if they comprise CPD1.

TABLE 10

Chemical stability of CPD1 in different isotonic formulation, wherein chemical stability is expressed normalised CPD1 purity in % as described in ASSAY III.

| Formulation | | Phosphate buffer | Chloride salt of CPD1OH | Concentration of tonicity | | Normalised CPD1 agonists purity in % | | | | |
|---|---|---|---|---|---|---|---|---|---|---|
| # | Comprises | mM | mg/mL | agent | pH | D0 | D3 | D7 | D14 | D24 |
| 5a | NaCl | 20 | 1 | 150 | 7 | 100 | ND | ND | ND | 95 |
| 21 | None | 20 | 1 | 230 | 7 | 100 | ND | ND | ND | 95 |
| 22 | Sucrose | 20 | 1 | 230 | 7 | 100 | ND | ND | ND | 51 |
| 23 | Dextrose | 20 | 1 | 230 | 7 | 100 | ND | ND | ND | 0 |
| 24 | Glycerol | 20 | 2 | 230 | 7 | 100 | ND | ND | ND | 88 |
| 1 | mannitol | 20 | 2 | 190 | 8 | 100 | 100 | 99 | 97 | ND |
| 2 | mannitol | 20 | 2 | 230 | 8 | 100 | 99 | 99 | 97 | ND |
| 3 | mannitol | 20 | 0.2 | 270 | 8 | 100 | 99 | 98 | 97 | ND |
| 4 | NaCl | 20 | 2 | 200 | 8 | 100 | 100 | 98 | 97 | ND |
| 6 | NaCl | 20 | 2 | 80 | 8 | 100 | 99 | 98 | 97 | ND |
| 7 | KCl | 20 | 2 | 200 | 8 | 100 | 99 | 98 | 97 | ND |

TABLE 10-continued

Chemical stability of CPD1 in different isotonic formulation, wherein chemical stability is expressed normalised CPD1 purity in % as described in ASSAY III.

| Formulation | | Phosphate buffer | Chloride salt of CPD1OH | Concentration of tonicity | | Normalised CPD1 agonists purity in % | | | | |
|---|---|---|---|---|---|---|---|---|---|---|
| # | Comprises | mM | mg/mL | agent | pH | D0 | D3 | D7 | D14 | D24 |
| 8 | KCl | 20 | 2 | 400 | 8 | 100 | 99 | 99 | 97 | ND |
| 9 | KCl | 20 | 2 | 80 | 8 | 100 | 100 | 98 | 97 | ND |
| 10 | prop glycol | 20 | 2 | 50 | 8 | 100 | 98 | 97 | 95 | ND |
| 11 | prop glycol | 20 | 2 | 100 | 8 | 100 | 98 | 97 | 95 | ND |
| 12 | prop glycol | 20 | 2 | 200 | 8 | 100 | 97 | 95 | 93 | ND |
| 14 | mannitol | 20 | 2 | 230 | 7.5 | 100 | 100 | 99 | 97 | ND |
| 15 | mannitol | 20 | 2 | 230 | 8 | 100 | 100 | 99 | 98 | ND |
| 16 | mannitol | 20 | 10 | 230 | 8 | 100 | 99 | 99 | 98 | ND |
| 17 | mannitol 230 | 100 | 2 | 230 | 8 | 100 | 100 | 98 | 97 | ND |
| 18 | mannitol 230 | 100 | 10 | 230 | 8 | 100 | 99 | 99 | 97 | ND |
| 19 | mannitol 230 | 20 | 0.2 | 230 | 7.5 | 100 | 100 | 98 | 97 | ND |
| 20 | mannitol + L-His 230 | 20 | 2 | 230 | 7.5 | 100 | 99 | 97 | | ND |
| 5 | NaCl 140 | 20 | 2 | 140 | 8 | 100 | 99 | 98 | 97 | ND |
| 13 | mannitol 230 | 20 | 2 | 230 | 7 | 100 | 99 | 99 | 98 | 97 |

ND = not determined.

Example 2: Long Term Stability at 5° C. Of Samples from 2 mq/mL Upscaled Batches (2.5 L) Comprising CPD1

CPD1 was produced according to ASSAY I, the pharmaceutical compositions (i.e. Formulations) were prepared and stored according to ASSAY II and the absolute CPD1 purity was measured by a HPLC, such as RP-HPLC according to ASSAY Ill at each time point as indicated in Tables 11-14, i.e. after 1 month (1M), 2 months (2M), 3 months (3M), 6 months (6M), 9 months (9M), 12 months (12M) and 24 months (24M) of storage at 5° C.±3

TABLE 11

Long term chemical stability at 5° C. of upscaled batch (2.5 L) comprising 2 mg/mL CPD1, wherein the chemical stability is expressed normalised CPD1 purity in %, as described in. ASSAY III

| Formulation 15 Upscaled batch 2 | | | Normalised CPD1 agonists purity in % | | | | | |
|---|---|---|---|---|---|---|---|---|
| mg/mL | D0 | 1M | 2M | 3M | 6M | 9M | 12M | 24M |
| Relative purity in % | 100 | 100 | 100 | 100 | 100 | 99 | 99 | 98 |

TABLE 12

Visual inspection solution, long term physical stability at 5° C. of upscaled batch (2.5 L) comprising 2 mg/mL CPD1. Visual inspection was performed according to ASSAY IVa.

| Formulation 15 | D0 | 1M | 2M | 3M | 6M | 9M | 12M | 24M |
|---|---|---|---|---|---|---|---|---|
| Upscaled batch 2 mg/mL | Vial containing a clear, colorless solution. | | | | | | | |

TABLE 13

Visual inspection for particles, long term physical stability at 5° C. of upscaled batch (2.5 L) comprising 2 mg/mL CPD1. Visual inspection was performed according to ASSAY IVa.

| Formulation 15 | D0 | 1M | 2M | 3M | 6M | 9M | 12M | 24M |
|---|---|---|---|---|---|---|---|---|
| Upscaled batch 2 mg/mL | Free from visible foreign particles | | | | | | | |

TABLE 14

Sub visual particles, long term physical stability at 5° C. of upscaled batch (2.5 L) comprising 2 mg/mL CPD1, Formulation 15 (N.P. = no particulates, and part/cont = particles per container). Detection of sub visible particles was performed according to ASSAY IVb.

| Timepoint | D0 | 1M | 2M | 3M | 6M | 9M | 12M | 24M |
|---|---|---|---|---|---|---|---|---|
| Subvisible particulate | N.P. | | N.P. | N.P. | | N.P. | | |
| ≥10 μm | | 9 part/ cont | | | 7 part/ cont | | 9 part/ cont | 10 part/ cont |
| ≥25 μm | | 1 part/ cont | | | 1 part/ cont | | 1 part/ cont | 0 part/ cont |

Example 3: Long Term Stability at 5° C. Of Samples from 10 mq/mL Upscaled Batches (2.5 L) Comprising CPD1

CPD1 was produced according to ASSAY I, the pharmaceutical compositions (i.e. Formulations) were prepared and stored according to ASSAY II and the absolute CPD1 purity was measured by a HPLC, such as RP-HPLC according to ASSAY Ill at each time point as indicated in Tables 15-18, i.e. after 1 month (1M), 2 months (2M), 3 months (3M), 6 months (6M), 9 months (9M), 12 months (12M) and 24 months (24M) of storage at 5° C.±3

TABLE 15

Long term chemical stability at 5° C. of upscaled batch (2.5 L) comprising 10 mg/mL CPD1, wherein the chemical stability is expressed normalised CPD1 purity in %, as described in ASSAY III.

| Formulation 16 Upscaled batch 2 | Normalised CPD1 agonists purity in % | | | | | | |
|---|---|---|---|---|---|---|---|
| mg/mL | D0 | 1M | 2M | 3M | 6M 9M | 12M | 24M |
| Relative purity in % | 100 | 100 | 100 | 100 | 100 100 | 98 | 99 |

TABLE 16

Visual inspection solution, long term physical stability at 5° C. of upscaled batch (2.5 L) comprising 10 mg/mL CPD1. Visual inspection was performed according to ASSAY IVa.

| Formulation 16 | D0 | 1M | 2M 3M 6M 9M 12M | 24M |
|---|---|---|---|---|
| Upscaled batch 10 mg/mL | Vial containing a clear, colorless solution. | | | |

TABLE 17

Visual inspection for particles, long term physical stability at 5° C. of upscaled batch (2.5 L) comprising 10 mg/mL CPD1. Visual inspection was performed according to ASSAY IVa.

| Formulation 16 | D0 1M 2M 3M 6M 9M 12M | 24M |
|---|---|---|
| Upscaled batch 10 mg/mL | Free from visible foreign particles. | |

TABLE 18

Sub visual particles, long term physical stability at 5° C. of upscaled batch (2.5 L) comprising 10 mg/mL CPD1, Formulation 16 (N.P. = no particulates, and part/cont = particles per container). Detection of sub visible particles was performed according to ASSAY IVb.

| Timepoint | D0 | 1M | 2M | 3M | 6M | 9M | 12M | 24M |
|---|---|---|---|---|---|---|---|---|
| Subvisible particulate | N.P. | | N.P. | N.P. | N.P. | N.P. | | |
| ≥10 µm | | 8 part/ cont | | | | | 9 part/ cont | 1 part/ cont |
| ≥25 µm | | 0 part/ cont | | | | | 0 part/ cont | 0 part/ cont |

TABLE 19

Long term chemical stability at 25° C. of upscaled batch (2.5 L) comprising 2 mg/mL CPD1, wherein the chemical stability is expressed normalised CPD1 purity in %, as described in ASSAY III.

| Formulation 15 | Normalised CPD1 agonists purity in % | | | | | | |
|---|---|---|---|---|---|---|---|
| Upscaled batch 2 mg/mL | D0 | 1M | 2M | 3M | 6M | 9M | 12M |
| Relative purity in % | 100 | 99 | 99 | 99 | 96 | 94 | 91 |

TABLE 20

Visual inspection solution, long term physical stability at 25° C. of upscaled batch(2.5 L) comprising 2 mg/mL CPD1. Visual inspection was performed according to ASSAY IVa.

| Formulation 15 | D0 | 1M | 2M | 3M | 6M | 9M | 12M |
|---|---|---|---|---|---|---|---|
| Unscaled batch 2 mg/mL | Vial containing a clear, colorless solution. | | | | | | |

TABLE 21

Visual inspection for particles, long term physical stability at 25° C. of upscaled batch (2.5 L) comprising 2 mg/mL CPD1. Visual inspection was performed according to ASSAY IVa.

| Formulation 15 | D0 | 1M | 2M | 3M | 6M | 9M | 12M |
|---|---|---|---|---|---|---|---|
| Unscaled batch 2 mg/mL | Free from visible foreign particles | | | | | | |

TABLE 22

Sub visual particles, long term physical stability at 25° C. of upscaled batch (2.5 L) comprising 2 mg/mL CPD1, Formulation 15 (N.P. = no particulates, and part/cont = particles per container). Detection of sub visible particles was performed according to ASSAY IVb.

| Timepoint | D0 | 1M | 2M | 3M | 6M | 9M | 12M |
|---|---|---|---|---|---|---|---|
| Subvisible particulate | N.P. | | N.P. | N.P. | | N.P. | |
| ≥10 µm | | 7 part/ cont | | | 8 part/ cont | | 9 part/ cont |
| ≥25 µm | | 1 part/ cont | | | 0 part/ cont | | 1 part/ cont |

Example 4: Long Term Chemical Stability at 25° C. Of Samples from 2 mq/mL Upscaled Batches (2.5 L) Comprising CPD1

CPD1 was produced according to ASSAY I, the pharmaceutical compositions (i.e. Formulations) were prepared and stored according to ASSAY II and the absolute CPD1 purity was measured by a HPLC, such as RP-HPLC according to ASSAY Ill at each time point as indicated in Tables 19-22, i.e. after 1 month (1M), 2 months (2M), 3 months (3M), 6 months (6M), 9 months (9M) and 12 months (12M) of storage at 25° C.±5° C./60% RH±5% RH in vials sealed with rubber stoppers.

Example 5: Long Term Chemical Stability at 25° C. Of Samples from 10 mq/mL Upscaled Batches (2.5 L) Comprising CPD1

CPD1 was produced according to ASSAY I, the pharmaceutical compositions (i.e. Formulations) were prepared and stored according to ASSAY II and the absolute CPD1 purity was measured by a HPLC, such as RP-HPLC according to ASSAY Ill at each time point as indicated in Tables 23-26, i.e. after 1 month (1M), 2 months (2M), 3 months (3M), 6 months (6M), 9 months (9M) and 12 months (12M) of storage at 25° C.±5° C./60% RH±5% RH in vials sealed with rubber stoppers.

TABLE 23

Long term chemical stability at 25° C. of upscaled batch (2.5 L) comprising 10 mg/mL CPD1, wherein the chemical stability is expressed normalised CPD1 purity in %, as described in ASSAY III.

| Formulation 16 Upscaled batch 10 | Normalised CPD1 agonists purity in % | | | | | | |
|---|---|---|---|---|---|---|---|
| mg/mL | D0 | 1M | 2M | 3M | 6M | 9M | 12M |
| Relative purity in % | 100 | 100 | 99 | 98 | 96 | 94 | 94 |

TABLE 24

Visual inspection solution, long term physical stability at 25° C. of upscaled batch (2.5 L) comprising 10 mg/mL CPD1. Visual inspection was performed according to ASSAY IVa.

| Formulation 16 | D0 | 1M | 2M | 3M | 6M | 9M | 12M |
|---|---|---|---|---|---|---|---|
| Upscaled batch 10 mg/mL | Vial containing a clear, colorless solution. | | | | | | |

TABLE 25

Visual inspection for particles, long term physical stability at 25° C. of upscaled batch (2.5 L) comprising 10 mg/mL CPD1. Visual inspection was performed according to ASSAY IVa.

| Formulation 16 | D0 | 1M | 2M | 3M | 6M | 9M | 12M |
|---|---|---|---|---|---|---|---|
| Upscaled batch 10 mg/mL | Free from visible foreign particles. | | | | | | |

TABLE 26

Sub visual particles, long term physical stability at 25° C. of upscaled batch (2.5 L) comprising 2 mg/mL CPD1, Formulation 15 (N.P. = no particulates, and part/cont = particles per container). Detection of sub visibleparticles was performed according to ASSAY IVb.

| Timepoint | D0 | 1M | 2M | 3M | 6M | 9M | 12M |
|---|---|---|---|---|---|---|---|
| Subvisible particulate | N.P. | | N.P. | N.P. | | N.P. | |
| ≥10 μm | | 7 part/ cont | | | 8 part/ cont | | 9 part/ cont |
| ≥25 μm | | 1 part/ cont | | | 0 part/ cont | | 1 part/ cont |

TABLE 27

Accelerated long term chemical stability at 40° C. of upscaled batch (2.5 L) comprising 2 mg/mL CPD1, wherein the chemical stability is expressed normalised CPD1 purity in %, as described in ASSAY III.

| | Formulation 15 | | | |
|---|---|---|---|---|
| Upscaled batch 2 mg/mL | D 0 | 1 M | 2 M | 3 M |
| Relative purity in % | 100 | 94 | 90 | 85 |

TABLE 28

Visual inspection solution, accelerated long term chemical stability at 40° C. of upscaled batch (2.5 L) comprising 2 mg/mL CPD1. Visual inspection was performed according to ASSAY IVa.

| Formulation 15 | D0 | 1M | 2M | 3M | 6M | 9M | 12M |
|---|---|---|---|---|---|---|---|
| Upscaled batch 2 mg/mL | Vial containing a clear, colorless solution. | | | | | | |

TABLE 29

Visual inspection for particles, accelerated long term chemical stability at 40° C. of upscaled batch (2.5 L) comprising 2 mg/mL CPD1. Visual inspection was performed according to ASSAY IVa.

| Formulation 15 | D0 | 1M | 2M | 3M | 6M | 9M | 12M |
|---|---|---|---|---|---|---|---|
| Upscaled batch 2 mg/mL | Free from visible foreign particles | | | | | | |

TABLE 30

Sub visual particles, accelerated long term physical stability at 40° C. of upscaled batch (2.5 L) comprising 2 mg/mL CPD1, Formulation 15 (N.P. = no particulates, and part/cont = particles per container). Detection of sub visible particles was performed according to ASSAY IVb.

| Timepoint | D 0 | 1 M | 2 M | 3 M |
|---|---|---|---|---|
| Subvisible particulate | N.P. | | | |
| ≥10 μm | | 4 part/cont | 9 part/cont | 16 part/cont |
| ≥25 μm | | 1 part/cont | 1 part/cont | 1 part/cont |

Example 6: Accelerated Long Term Stability at 40° C. Of Samples from 2 mq/mL Upscaled Batches (2.5 L) Comprising CPD1

CPD1 was produced according to ASSAY I, the pharmaceutical compositions (i.e. Formulations) where prepared and stored according to ASSAY II and the absolute CPD1 purity was measured by a HPLC, such as RP-HPLC according to ASSAY Ill at each time point as indicated in Tables 27-30, i.e. after 1 month (1M), 2 months (2M), 3 months (3M) of storage at 40° C.±5° C./75% RH±5% RH in vials sealed with rubber stoppers.

Example 7: Accelerated Long Term Stability at 40° C. Of Samples from 10 mq/mL Upscaled Batches (2.5 L) Comprising CPD1

CPD1 was produced according to ASSAY I, the pharmaceutical compositions (i.e. Formulations) where prepared and stored according to ASSAY II and the absolute CPD1 purity was measured by a HPLC, such as RP-HPLC according to ASSAY Ill at each time point as indicated in Tables 31-34, i.e. after 1 month (1M), 2 months (2M), 3 months (3M), 6 months (6M), 9 months (9M) and 12 months (12M) of storage at 40° C.±5° C./75% RH±5% RH in vials sealed with rubber stoppers.

TABLE 31

Accelerated long term chemical stability at 40°
C. of upscaled batch (2.5 L) comprising 10 mg/mL CPD1,
wherein the chemical stability is expressed normalised
CPD1 purity in %, as described in ASSAY III.

|  | Formulation 16 | | | |
| --- | --- | --- | --- | --- |
|  | D 0 | 1 M | 2 M | 3 M |
| Upscaled batch 10 mg/mL |  |  |  |  |
| Relative purity in % | 100 | 96 | 89 | 86 |

TABLE 32

Visual inspection solution, accelerated long term physical stability
at 40° C. of upscaled batch (2.5 L) comprising 10 mg/mL
CPD1. Visual inspection was performed according to ASSAY IVa.

|  | Formulation 16 | | | |
| --- | --- | --- | --- | --- |
|  | D 0 | 1 M | 2 M | 3 M |
| Upscaled batch 10 mg/mL | Vial containing a clear, colorless solution. | | | |

TABLE 33

Visual inspection for particles, accelerated long
term physical stability at 40° C. of upscaled
batch (2.5 L) comprising 10 mg/mL CPD1. Visual inspection
was performed according to ASSAY IVa.

|  | Formulation 16 | | | |
| --- | --- | --- | --- | --- |
|  | D 0 | 1 M | 2 M | 3 M |
| Upscaled batch 10 mg/mL | Free from visible foreign particles. | | | |

TABLE 34

Sub visual particles, accelerated long term physical stability
at 40° C. of upscaled batch (2.5 L) comprising 2 mg/mL
CPD1, Formulation 16 (N.P. = no particulates, and
part/cont = particles per container). Detection of
sub visible particles was performed according to ASSAY IVb.

| Timepoint | D 0 | 1 M | 2 M | 3 M |
| --- | --- | --- | --- | --- |
| Subvisible particulate | N.P. |  |  |  |
| ≥10 μm |  | 10 part/cont | 10 part/cont | 13 part/cont |
| ≥25 μm |  | 0 part/cont | 0 part/cont | 1 part/cont |

Example 8: Accelerated Chemical Stability at 40° C. 14 Days of Formulations with Different Buffer Systems, Laboratory Scale CPD1 was produced according to ASSAY I, the pharmaceutical compositions (i.e. Formulations) where prepared and stored according to ASSAY II and the absolute CPD1 purity was measured by a HPLC, such as RP-HPLC according to ASSAY Ill at each time point as indicated in Table 35 i.e. after 14 days (14D) of storage at 40° C.±5° C./60% RH±5% RH in vials sealed with rubber stoppers.

TABLE 35

Accelerated long term chemical stability at 40°
C. of laboratory scale compositions comprising 0.2
mg/mL CPD1, wherein the chemical stability is expressed
normalised CPD1 purity in %, as described in ASSAY III.

| Formulation # | CPD1 [mg/mL] | pH | Histidine [mM] | Phosphate [mM] | Relative purity CPD1 |
| --- | --- | --- | --- | --- | --- |
| A | 0.2 | 6 | 20 |  | 94 |
| D | 0.2 | 6 | 50 |  | 94 |
| G | 0.2 | 6 |  | 20 | 94 |
| J | 0.2 | 6 |  | 50 | 94 |
| B | 0.2 | 7 | 20 |  | 93 |
| E | 0.2 | 7 | 50 |  | 91 |
| H | 0.2 | 7 |  | 20 | 94 |
| K | 0.2 | 7 |  | 50 | 94 |
| C | 0.2 | 8 | 20 |  | 86 |
| F | 0.2 | 8 | 50 |  | 85 |
| I | 0.2 | 8 |  | 20 | 95 |
| L | 0.2 | 8 |  | 50 | 94 |

Example 9: Accelerated Physical Stability at 40° C. 4 Days of Formulations in the pH Range 6-8 Laboratory Scale pH determines the aggregation propensity of CPD1. No difference between having mannitol as tonicity agent compared to control (no tonicity agent) was detected. At 2 and 10 mg/mL CPD1 amyloid formation was observed at pH 6 and no fibrillation was observed at pH 7 or 8.

TABLE 36

Aggregation of 2 mg/mL CPD1 according to
ASSAY IVc (FD = Fibrillation Detected
and FND = Fibrillation Not Detected)

| pH and buffer concentration of formulation | No added tonicity agent | 270 mM mannitol |
| --- | --- | --- |
| 20 mM phosphate pH 6 | FD | FD |
| 20 mM phosphate pH 6.5 | FND | FND |
| 20 mM phosphate pH 7 | FND | FND |
| 20 mM phosphate pH 8 | FND | FND |

TABLE 37

Aggregation of 10 mg/mL CPD1 according to
ASSAY IVc (FD = Fibrillation Detected
and FND = Fibrillation Not Detected)

| pH and buffer concentration of formulation | No added tonicity agent | 270 mM mannitol |
| --- | --- | --- |
| 20 mM phosphate pH 6 | FD | FD |
| 20 mM phosphate pH 6.5 | FND | FND |
| 20 mM phosphate pH 7 | FND | FND |
| 20 mM phosphate pH 8 | FND | FND |

Example 10: Structural Properties of CPD1 in Regards to pH 6-8, Laboratory Scale The structural properties were evaluated using AUC at pH 6, 7 and 8 in 20 mM phosphate buffer, 230 mM mannitol 2 mg/ml CPD1. Results are shown in Tables 38 and 39.

TABLE 38

Formulation composition of samples analysed by AUC.

| Formulation # | Composition |
|---|---|
| 1 | 20 mM phosphate pH 8, 230 mM mannitol, 2 mg/mL CPD1 |
| 2 | 20 mM phosphate pH 7, 230 mM mannitol, 2 mg/mL CPD1 |
| 3 | 20 mM phosphate pH 6, 230 mM mannitol, 2 mg/mL CPD1 |

TABLE 39

Sedimentation coefficients of formulations from Table 38.

| Formulation # | f/f0 | S1 [S] | $s_{20,w}$/[s] | [%] | S2 [S] | [%] | >S2 [%] |
|---|---|---|---|---|---|---|---|
| 1 | 1.37 | 1.03 | 1.23 | 98.8 | 3.91 | 0.7 | 0.5 |
| 2 | 1.33 | 1.18 | 1.40 | 98.4 | 3.67 | 0.9 | 0.7 |
| 3 | 1.13 | 1.67 | 1.98 | 43.0 | 2.42 | 55.2 | 1.8 |

Formulation 1 (2 mg/mL; 20 mM phosphate (pH 8), 230 mM mannitol): The sedimentation coefficient distributions (SCD) exhibit a predominant population ($s_{20;w}$=1.23 S) with a relative content of 98.8% and an apparent mass of 11.5 kDa. Accordingly, the predominant population is tentatively assigned as trimeric peptide. The remaining material represents more rapidly sedimenting oligomers/aggregates with sedimentation coefficients up to approximately 10 S.

Formulation 2 (2 mg/mL; 20 mM phosphate (pH 7), 230 mM mannitol): The relative content of putative trimers (s20;w=1.40 S) with an apparent mass of 11.2 kDa is nearly identical to that in Formulation 1.

Formulation 3 (2 mg/mL; 20 mM phosphate (pH 6), 230 mM mannitol) exhibits the highest self-association degree of all samples. Two major populations (s20;w=1.98 S and 2.78 S) with a comparable relative content of 43.0% and 55.2%, respectively, were detected, whereas trimers are absent. The slightly less abundant population with an apparent mass of 17 kDa represents putative tetrameric peptides and the more rapidly sedimenting population with a mean molar mass of 30 kDa contains putative heptamers or octamers. The broad shape of the second population indicates the presence of additional size- and conformation-variants, e.g. hexamers and nonamers. The remaining material is distributed among larger oligomers up to 10 S.

Example 11: Long Term Stability of 2 and 10 mg/mL CPD1 in 20 mM Phosphate Buffer pH 8 115 mM NaCl at 5° C. In Laboratory Scale CPD1 was produced according to ASSAY I, the pharmaceutical compositions (i.e. Formulations) were prepared and stored according to ASSAY II in laboratory scale having a final concentration of 115 mM NaCl instead of 230 mM Mannitol. The absolute CPD1 purity was measured by a HPLC, such as RP-HPLC according to ASSAY Ill at each time point as indicated in Tables 40-41, i.e. after 1 month (1M), 3 months (3M), 6 months (6M),12 months (12M) and 24 months (24) of storage at 5° C.±3° C. in vials sealed with rubber stoppers.

TABLE 40

Long term stability of 2 and 10 mg/mL CPD1 in 20 mM phosphate buffer pH 8 115 mM NaCl at 5° C. in laboratory scale wherein the chemical stability is expressed normalised CPD1 purity in %, as described in ASSAY III.

| Time | Normalised CPD1 agonists purity in % D0 | 1M | 3M | 6M | 12M | 24M |
|---|---|---|---|---|---|---|
| 2 mg/mL CPD1, 20 mM Phosphate, pH 8, 115 mM NaCl | 100.0 | 99.9 | 100.1 | 99.8 | 99.8 | 99.4 |
| 10 mg/mL CPD1, 20 mM Phosphate, pH 8, 115 mM NaCl | 100.0 | 99.8 | 99.9 | 99.8 | 99.6 | 99.2 |

TABLE 41

Visual inspection solution, long term stability of 2 and 10 mg/mL CPD1 in 20 mM phosphate buffer pH 8 115 mM NaCl at 5° C. in laboratory scale. Visual inspection was performed according to ASSAY IVa.

| Time | D0 | 1M | 3M | 6M | 12M | 24M |
|---|---|---|---|---|---|---|
| 2 mg/mL CPD1, 20 mM Phosphate, pH 8, 115 mM NaCl | Vial containing a clear, colorless solution. | | | | | |
| 10 mg/mL CPD1, 20 mM Phosphate, pH 8, 115 mM NaCl | Vial containing a clear, colorless solution. | | | | | |

---

The invention claimed is:

1. An isotonic parenteral pharmaceutical composition, comprising:
   a. at least about 1 mg/mL of one or more GLP-1/GLP-2 dual agonist, wherein the one or more GLP-1/GLP-2 dual agonist is Hy-H[Aib]EGSFTSELATILD[K([17-carboxy-heptadecanoyl]-isoGlu)QAARDFIAWLIQH-KITD-OH (CPD10H) (SEQ ID NO: 1) or any pharmaceutically acceptable salt thereof
   b. about 5 mM to about 50 mM of phosphate buffer component; and
   c. about 190 mM to about 240 mM of one or more tonicity agent,
   wherein said one or more tonicity agent comprises or consists of mannitol, wherein said composition further comprises a solvent, and
   wherein said composition has a pH of about pH 6.0 to about pH 8.2.

2. The isotonic parenteral pharmaceutical composition of claim 1, wherein the mannitol is D-mannitol.

3. The isotonic parenteral pharmaceutical composition according to claim 1, wherein said buffer component is a sodium phosphate buffer.

4. The isotonic parenteral pharmaceutical composition of claim 3,
   wherein said sodium phosphate buffer is
       disodium phosphate,
       sodium dihydrogen phosphate, or
       a combination thereof.

5. The isotonic parenteral pharmaceutical composition of claim 1, wherein the osmolality of the composition is about 230 mOsmol/kg to about 370 mOsmol/kg.

6. The isotonic parenteral pharmaceutical composition of claim 1, wherein said buffer component is at a final concentration of about 20 mM, said one or more tonicity agent is mannitol at a final concentration of about 190 mM to about 240 mM and wherein the pH is between about pH 7.0 and about pH 8.0.

7. The isotonic parenteral pharmaceutical composition of claim 1, wherein said buffer component is at a final concentration of about 15 mM to about 30 mM, said one or more tonicity agent is mannitol at a final concentration of about 230 mM and wherein the pH is between about pH 7.0 and about pH 8.0.

8. The isotonic parenteral pharmaceutical composition of claim 1, wherein said one or more GLP-1/GLP-2 dual agonist, or any pharmaceutically acceptable salt thereof, is present at a concentration of about 1 mg/mL to about 15 mg/mL.

9. The isotonic parenteral pharmaceutical composition of claim 1, comprising a phosphate buffer at a concentration of about 15 mM to about 30 mM mannitol at a concentration of about 230 mM, water for injection and sodium hydroxide and/or hydrochloric acid for pH adjustment to a pH of about pH 8.0, wherein said one or more GLP-1/GLP-2 dual agonist is CPD1 OH or a chloride salt thereof and is present at about 2 mg/mL.

10. The isotonic parenteral pharmaceutical composition of claim 1, comprising a phosphate buffer at a concentration of about 15 mM to about 30 mM mannitol at a concentration of about 230 mM, water for injection and sodium hydroxide and/or hydrochloric acid for pH adjustment to a pH of about pH 8.0, wherein said one or more GLP-1/GLP-2 dual agonist is CPD1 OH or a chloride salt thereof and is present at about 10 mg/mL.

11. The isotonic parenteral pharmaceutical composition of claim 1,
    wherein said composition comprises 2 mg of CPD1 OH, 2.65 mg of $Na_2HPO_4$ (anhydrous), 0.16 mg of $NaH_2PO_4$, 41.90 ma of D-mannitol, water for injection to make 1 mL, and sodium hydroxide and/or hydrochloric acid for pH adjustment to a pH of about pH 8.0.

12. The isotonic parenteral pharmaceutical composition of claim 1, wherein said composition comprises 10 ma of CPD1 OH, 2.65 ma of $Na_2HPO_4$ (anhydrous), 0.16 ma of $NaH_2PO_4$ (anhydrous), 41.90 ma of D-mannitol, water for injection to make 1 mL, and sodium hydroxide and/or hydrochloric acid for pH adjustment to a pH of about pH 8.0.

13. The isotonic parenteral pharmaceutical composition of claim 1 wherein said composition has a shelf-life of at least 24 months at 5° C.

14. The isotonic parenteral pharmaceutical composition of claim 1 wherein said composition has a chemical stability of at least about 90% after 12 months storage at 25° C.

15. The isotonic parenteral pharmaceutical composition of claim 1 wherein said composition has a chemical stability of at least about 97% after 12 months storage at about 5° C.

16. The isotonic parenteral pharmaceutical composition of claim 1 wherein said composition has a chemical stability of at least about 97% after 24 months storage at about 5° C.

17. A method for improving the chemical stability of an isotonic parenteral pharmaceutical composition comprising at least about 1 mg/mL of one or more GLP-1/GLP-2 dual agonist, wherein the one or more GLP-1/GLP-2 dual agonist is Hy-H[Aib]EGSFTSELATILD[K([17-carboxy-heptade-canoyll-isoGlu)1QAARDFIAWLIQHKITD-OH (CPD10H) (SEQ ID NO: 1) or any Pharmaceutically acceptable salt thereof;
    wherein said method comprises adding mannitol to said composition.

18. A method for:
    increasing intestinal mass, improving intestinal function, increasing intestinal blood flow, or repairing intestinal damage or dysfunction, in a subject in need thereof,
    the method comprising administering to the subject the isotonic parenteral pharmaceutical composition of claim 1.

19. The isotonic parenteral pharmaceutical composition of claim 1, wherein the phosphate buffer component is at a concentration from about 10 mM to about 40 mM.

20. The isotonic parenteral pharmaceutical composition of claim 1, wherein the composition has a pH from about pH 7.0 to about pH 8.0.

21. The isotonic parenteral pharmaceutical composition of claim 1, wherein the one or more tonicity agent is at a final concentration of about 230 mM.

22. The method of claim 17, wherein the mannitol is D-mannitol.

23. A method for the prophylaxis or treatment of malabsorption, ulcers, short-bowel syndrome, cul-de-sac syndrome, inflammatory bowel disease, irritable bowel syndrome, pouchitis, celiac sprue, tropical sprue, hypogammaglobulinemic sprue, mucositis induced by chemotherapy or radiation therapy, diarrhoea induced by chemotherapy or radiation therapy, low grade inflammation, metabolic endotoxemia, necrotising enterocolitis, primary biliary cirrhosis, hepatitis, fatty liver disease, or gastrointestinal side-effects of inflammatory conditions, in a subject in need thereof, the method comprising administering to the subject the isotonic parenteral pharmaceutical composition of claim 1.

24. A method for reducing or inhibiting weight gain, reducing gastric emptying or intestinal transit, reducing food intake, reducing appetite, or promoting weight loss, in a subject in need thereof, the method comprising administering to the subject the isotonic parenteral pharmaceutical composition of claim 1.

25. A method for the prophylaxis or treatment of obesity, morbid obesity, obesity-linked gallbladder disease, obesity-induced sleep apnoea, inadequate glucose control, glucose tolerance, dyslipidaemia, diabetes, pre-diabetes, metabolic syndrome or hypertension, in a subject in need thereof, the method comprising administering to the subject the isotonic parenteral pharmaceutical composition of claim 1.

\* \* \* \* \*

SEQUENCE LISTING

```
<160> NUMBER OF SEQ ID NOS: 3

<210> SEQ ID NO 1
<211> LENGTH: 33
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa is [Aib]
<220> FEATURE:
<221> NAME/KEY: MISC_FEATURE
<222> LOCATION: (16)..(16)
<223> OTHER INFORMATION: Xaa is an L or D lysine residue in which the
        side chain is conjugated to the GLP-1/GLP-2 dual agonist and
        wherein said side chain is [K([17-carboxy-heptadecanoyl]-isoGlu)]
```

```
<400> SEQUENCE: 1

His Xaa Glu Gly Ser Phe Thr Ser Glu Leu Ala Thr Ile Leu Asp Xaa
1               5                   10                  15

Gln Ala Ala Arg Asp Phe Ile Ala Trp Leu Ile Gln His Lys Ile Thr
                20                  25                  30

Asp

<210> SEQ ID NO 2
<211> LENGTH: 33
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa is [Aib]
<220> FEATURE:
<221> NAME/KEY: MISC_FEATURE
<222> LOCATION: (5)..(5)
<223> OTHER INFORMATION: Xaa is T or S (wherein at least one of X5 and
      X7 is T)
<220> FEATURE:
<221> NAME/KEY: MISC_FEATURE
<222> LOCATION: (7)..(7)
<223> OTHER INFORMATION: Xaa is T or S (wherein at least one of X5 and
      X7 is T)
<220> FEATURE:
<221> NAME/KEY: MISC_FEATURE
<222> LOCATION: (16)..(16)
<223> OTHER INFORMATION: Xaa is an L or D lysine residue in which the
      side chain is conjugated to the GLP-1/GLP-2 agonist
<220> FEATURE:
<221> NAME/KEY: MISC_FEATURE
<222> LOCATION: (28)..(28)
<223> OTHER INFORMATION: Xaa is Q, E, A, H, Y, L, K, R or S
<220> FEATURE:
<221> NAME/KEY: MISC_FEATURE
<222> LOCATION: (29)..(29)
<223> OTHER INFORMATION: Xaa is H, Y or Q

<400> SEQUENCE: 2

His Xaa Glu Gly Xaa Phe Xaa Ser Glu Leu Ala Thr Ile Leu Asp Xaa
1               5                   10                  15

Gln Ala Ala Arg Asp Phe Ile Ala Trp Leu Ile Xaa Xaa Lys Ile Thr
                20                  25                  30

Asp

<210> SEQ ID NO 3
<211> LENGTH: 33
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa is [Aib]
<220> FEATURE:
<221> NAME/KEY: MISC_FEATURE
<222> LOCATION: (5)..(5)
<223> OTHER INFORMATION: Xaa is T or S
<220> FEATURE:
<221> NAME/KEY: MISC_FEATURE
<222> LOCATION: (16)..(16)
<223> OTHER INFORMATION: Xaa is an L or D lysine residue in which the
      side chain is conjugated to the GLP-1/GLP-2 dual agonist and
      wherein said side chain is [K([17-carboxy-heptadecanoyl]-isoGlu)]
<220> FEATURE:
<221> NAME/KEY: MISC_FEATURE
<222> LOCATION: (28)..(28)
```

-continued

---

```
<223> OTHER INFORMATION: Xaa is Q, E, A, H, Y, L, K, R or S

<400> SEQUENCE: 3

His Xaa Glu Gly Xaa Phe Thr Ser Glu Leu Ala Thr Ile Leu Asp Xaa
1               5                   10                  15

Gln Ala Ala Arg Asp Phe Ile Ala Trp Leu Ile Xaa His Lys Ile Thr
            20                  25                  30

Asp
```